US012606856B2

(12) United States Patent
Horgan et al.

(10) Patent No.: US 12,606,856 B2
(45) Date of Patent: Apr. 21, 2026

(54) INCREASING LONG-SEQUENCE YIELDS IN TEMPLATE-FREE ENZYMATIC SYNTHESIS OF POLYNUCLEOTIDES

(71) Applicant: DNA Script, Le Kremlin-Bicêtre (FR)

(72) Inventors: Adrian Horgan, Paris (FR); Stephen C. Macevicz, Cupertino, CA (US)

(73) Assignee: DNA SCRIPT, Le Kremlin-Bicêtre (FR)

( * ) Notice: Subject to any disclaimer, the term of this patent is extended or adjusted under 35 U.S.C. 154(b) by 1065 days.

(21) Appl. No.: 17/636,256

(22) PCT Filed: Sep. 21, 2020

(86) PCT No.: PCT/EP2020/076315
§ 371 (c)(1),
(2) Date: Feb. 17, 2022

(87) PCT Pub. No.: WO2021/058438
PCT Pub. Date: Apr. 1, 2021

(65) Prior Publication Data
US 2022/0403436 A1 Dec. 22, 2022

(30) Foreign Application Priority Data

Sep. 23, 2019 (EP) .................................... 19199022

(51) Int. Cl.
*C12Q 1/68* (2018.01)
*C12P 19/34* (2006.01)
*C12Q 1/6869* (2018.01)

(52) U.S. Cl.
CPC ............ *C12P 19/34* (2013.01); *C12Q 1/6869* (2013.01)

(58) Field of Classification Search
CPC ............................... C12P 19/34; C12Q 1/6869
See application file for complete search history.

(56) References Cited

U.S. PATENT DOCUMENTS

| | | | |
|---|---|---|---|
| 5,047,524 A | 9/1991 | Andrus et al. | |
| 5,367,066 A | 11/1994 | Urdea et al. | |
| 5,436,143 A | 7/1995 | Hyman | |
| 5,474,796 A | 12/1995 | Brennan | |
| 5,667,667 A | 9/1997 | Southern | |
| 5,700,642 A | 12/1997 | Monforte et al. | |
| 5,739,386 A | 4/1998 | Holmes | |
| 5,744,595 A | 4/1998 | Srivastava et al. | |
| 5,763,594 A | 6/1998 | Hiatt et al. | |
| 5,808,045 A | 9/1998 | Hiatt et al. | |

(Continued)

FOREIGN PATENT DOCUMENTS

| | | |
|---|---|---|
| CN | 101547928 A | 9/2009 |
| CN | 106459135 | 2/2017 |

(Continued)

OTHER PUBLICATIONS

Altschul et al., "Protein Database Searches Using Compositionally Adjusted" FEBS J., 272: 5101-5109 (2005).

(Continued)

*Primary Examiner* — Jezia Riley
(74) *Attorney, Agent, or Firm* — MORRISON & FOERSTER LLP

(57) ABSTRACT

The present invention is directed to methods and kits for template-free enzymatic synthesis of polynucleotides employing hybridization stringency and/or nuclease digestion for removing failure sequences.

11 Claims, 15 Drawing Sheets
Specification includes a Sequence Listing.

(56) References Cited

U.S. PATENT DOCUMENTS

| | | | |
|---|---|---|---|
| 5,830,655 A | 11/1998 | Monforte et al. |
| 6,093,302 A | 7/2000 | Montgomery |
| 6,251,595 B1 | 6/2001 | Gordon et al. |
| 6,280,595 B1 | 8/2001 | Montgomery |
| 6,306,599 B1 | 10/2001 | Perbost |
| 6,323,043 B1 | 11/2001 | Caren et al. |
| 6,426,184 B1 | 7/2002 | Gao et al. |
| 6,444,111 B1 | 9/2002 | Montgomery |
| 6,664,097 B2 | 12/2003 | Russell et al. |
| 6,921,636 B1 | 7/2005 | Brennan |
| 7,057,026 B2 | 6/2006 | Bames et al. |
| 7,276,336 B1 | 10/2007 | Webb et al. |
| 7,345,159 B2 | 3/2008 | Ju et al. |
| 7,491,680 B2 | 2/2009 | Gao et al. |
| 7,534,561 B2 | 5/2009 | Sana et al. |
| 7,544,794 B1 | 6/2009 | Benner |
| 7,566,537 B2 | 7/2009 | Balasubramanian et al. |
| 7,713,698 B2 | 5/2010 | Ju et al. |
| 7,790,869 B2 | 9/2010 | Ju et al. |
| 7,838,466 B2 | 11/2010 | Gao et al. |
| 8,034,923 B1 | 10/2011 | Benner et al. |
| 8,212,020 B2 | 7/2012 | Benner et al. |
| 8,394,586 B2 | 3/2013 | Balasubramanian et al. |
| 8,623,628 B2 | 1/2014 | Ost et al. |
| 8,808,988 B2 | 8/2014 | Zhao et al. |
| 8,852,910 B2 | 10/2014 | Smith et al. |
| 9,075,041 B2 | 7/2015 | Kavusi et al. |
| 9,121,062 B2 | 9/2015 | Balasubramanian et al. |
| 9,267,213 B1 | 2/2016 | Maurer et al. |
| 9,339,782 B1 | 5/2016 | Gindilis |
| 9,410,197 B2 | 8/2016 | Bergmann et al. |
| 9,765,309 B2 | 9/2017 | Chen et al. |
| 9,874,538 B2 | 1/2018 | Johnson et al. |
| 9,910,008 B2 | 3/2018 | Johnson et al. |
| 10,150,954 B2 | 12/2018 | Bomati et al. |
| 10,435,676 B2 | 10/2019 | Champion et al. |
| 10,472,383 B2 | 11/2019 | Benner |
| 10,752,887 B2 | 8/2020 | Champion et al. |
| 10,837,040 B2 | 11/2020 | Ybert et al. |
| 10,913,964 B2 | 2/2021 | Ybert et al. |
| 11,059,849 B2 | 7/2021 | Ybert et al. |
| 11,208,637 B2 | 12/2021 | Champion et al. |
| 11,390,856 B2 | 7/2022 | Ybert et al. |
| 11,685,941 B2 | 6/2023 | Ybert et al. |
| 11,859,217 B2 | 1/2024 | Champion et al. |
| 12,065,461 B2 | 8/2024 | Sarac et al. |
| 12,071,638 B2 | 8/2024 | Champion et al. |
| 12,173,333 B2 | 12/2024 | Ybert et al. |
| 12,286,652 B2 | 4/2025 | Champion et al. |
| 12,371,680 B2 | 7/2025 | Champion et al. |
| 12,377,397 B2 | 8/2025 | Martin et al. |
| 12,421,628 B2 | 9/2025 | Horgan et al. |
| 12,428,668 B2 | 9/2025 | Godron et al. |
| 2003/0170698 A1 | 9/2003 | Gascoyne et al. |
| 2003/0186226 A1 | 10/2003 | Brennan et al. |
| 2004/0106728 A1 | 6/2004 | McGall et al. |
| 2004/0238369 A1 | 12/2004 | Southern et al. |
| 2005/0037991 A1 | 2/2005 | Bodepudi et al. |
| 2006/0234264 A1 | 10/2006 | Hardenbol |
| 2007/0087417 A1 | 4/2007 | Namsaraev |
| 2012/0129770 A1 | 5/2012 | Ramakrishna et al. |
| 2015/0315541 A1 | 11/2015 | Bancel et al. |
| 2016/0046974 A1 | 2/2016 | Efeavitch et al. |
| 2016/0108382 A1 | 4/2016 | Efeavitch et al. |
| 2019/0078065 A1 | 3/2019 | Baiga et al. |
| 2019/0078126 A1 | 3/2019 | Baiga et al. |
| 2019/0211315 A1 | 7/2019 | Champion et al. |
| 2019/0264248 A1 | 8/2019 | Ybert et al. |
| 2019/0300923 A1 | 10/2019 | Ybert et al. |
| 2019/0390178 A1 | 12/2019 | Champion et al. |
| 2020/0002690 A1 | 1/2020 | Ybert et al. |
| 2020/0231619 A1 | 7/2020 | Ybert et al. |
| 2020/0370027 A1 | 11/2020 | Ybert et al. |
| 2021/0009970 A1 | 1/2021 | Champion et al. |
| 2021/0130863 A1 | 5/2021 | Ybert et al. |
| 2021/0214382 A1 | 7/2021 | Sarac et al. |
| 2021/0332351 A1 | 10/2021 | Horgan et al. |
| 2022/0002687 A1 | 1/2022 | Champion et al. |
| 2022/0315970 A1 | 10/2022 | Horgan |
| 2022/0356510 A1 | 11/2022 | Godron et al. |
| 2022/0403354 A1 | 12/2022 | Champion et al. |
| 2022/0403434 A1 | 12/2022 | Heinisch et al. |
| 2022/0403435 A1 | 12/2022 | Horgan et al. |
| 2022/0411840 A1 | 12/2022 | Champion et al. |
| 2023/0062303 A1 | 3/2023 | Champion et al. |
| 2023/0089448 A1 | 3/2023 | Horgan et al. |
| 2023/0159903 A1 | 5/2023 | Soskine et al. |
| 2023/0167421 A1 | 6/2023 | Ybert et al. |
| 2023/0193222 A1 | 6/2023 | Ybert et al. |
| 2023/0203553 A1 | 6/2023 | Thomas |
| 2023/0241571 A1 | 8/2023 | Martin et al. |
| 2023/0313255 A1 | 10/2023 | Horgan et al. |
| 2023/0416708 A1 | 12/2023 | Loftie-Eaton et al. |
| 2024/0052391 A1 | 2/2024 | Godron et al. |
| 2024/0093165 A1 | 3/2024 | Champion et al. |
| 2024/0093256 A1 | 3/2024 | Soskine et al. |
| 2024/0124855 A1 | 4/2024 | Ybert et al. |
| 2024/0254459 A1 | 8/2024 | Champion et al. |
| 2024/0279700 A1 | 8/2024 | Horgan |
| 2024/0352443 A1 | 10/2024 | Creton et al. |
| 2025/0002879 A1 | 1/2025 | Mchale et al. |
| 2025/0034532 A1 | 1/2025 | Mchale et al. |
| 2025/0205700 A1 | 6/2025 | Lachaize et al. |
| 2025/0215617 A1 | 7/2025 | Horgan et al. |
| 2025/0223575 A1 | 7/2025 | Champion et al. |
| 2025/0283132 A1 | 9/2025 | De et al. |

FOREIGN PATENT DOCUMENTS

| | | |
|---|---|---|
| CN | 107074903 A | 8/2017 |
| WO | WO1991/006678 | 5/1991 |
| WO | 01/94546 A2 | 12/2001 |
| WO | WO2004/005667 | 1/2004 |
| WO | WO2015/159023 | 10/2015 |
| WO | WO2017/216472 | 12/2017 |
| WO | WO2019/135007 | 7/2019 |
| WO | WO2020/099451 | 1/2020 |
| WO | WO2020/141143 | 7/2022 |

OTHER PUBLICATIONS

Altschul et al., "Gapped BLAST and PSI-BLAST: a new generation of protein database search programs" Nucleic Acids Research, 25(17): 3389-3402 (1997).

Beaucage et al., "Advances in the Synthesis of Oligonucleotides by the Phosphoramidite Approach" Tetrahedron etters, 48(12): 2223-2311 (1992).

Becker et al., "The Enzymatic Cleavage of Phosphate Termini from Polynucleotides" J. Biol. Chem., 242(5): 936-950 (1967).

Bentolila et al., "The Two Isoforms of Mouse Terminal Deoxynucleotidyl Transferase Differ in both the Ability to add N Regions and Subcellular Localization" EMBO J., 14: 4221-4229 (1995).

Boule et al., "High-level expression of murine terminal deoxynucleotidyl transferase in Escherichia coli grown at low temperature and overexpressing argU tRNA" Mol. Biotechnology, 10: 199-208 (1998).

Cameron et al., "3'-Phosphatase activity in T4 polynucleotide kinase" Biochemistry, 16(23): 5120-5126 (1977).

Canard et al., "Catalytic editing properties of DNA polymerases" Proc. Natl. Acad. Sci., 92:10859-10863 (1995).

Delarue et al., "Crystal structures of a template-independent DNA polymerase: Murine terminal deoxynucleotidyltransferase" EMBO J., 21: 427-439 (2002).

Egeland et al., "Electrochemically directed synthesis of oligonucleotides for DNA microarray fabrication" Nucleic Acids Research, 33(14): el25 (2005).

Ferrero et al., "Chemoenzymatic Transformationsin Nucleoside Chemistry" Monatshefte fur Chemie, 131: 585-616 (2000).

Fomina et al., "An electrochemical platform for localized pH control on demand" LabChip, 16: 2236-2244 (2016).

(56) References Cited

OTHER PUBLICATIONS

Grantham, "Amino Acid Difference Formula to Help Explain Protein Evolution" Science, 185: 862-864 (1974).

Guo et al., "Four-color DNA sequencing with 3'-O-modified nucleotide reversible terminators and chemically cleavable fluorescent dideoxynucleotides" Proc. Natl. Acad. Sci., 105(27): 9145-9150 (2008).

Levine et al., "Active CMOS Sensor Array for Electrochemical Biomolecular Detection" IEEE J. Solid State Circuits, 43: 1859-1871 (2008).

Jensen et al., "Template-Independent Enzymatic 11 Oligonucleotide Synthesis (TiEOS): Its History, Prospects, and Challenges" Biochemistry, 57: 1821-1832 (2018).

Kodumal et al., "Total synthesis of long DNA sequences: Synthesis of a contiguous 32-kb polyketide synthase gene cluster" Proc. Natl. Acad. Sci., 101: 15573-15578 (2004).

Mathews et al., "Photo-cleavable nucleotides for primer free enzyme mediated DNA synthesis" Organic & Biomolecular Chemistry, 14: 8278-8288 (2016).

Meng et al., "Design and Synthesis of a Photocleavable Fluorescent Nucleotide 3'-O-Allyl-dGTP-PC-Bodipy-FL-510 as a Reversible Terminator for DNA Sequencing by Synthesis" J. Org. Chem., 14: 3248-3252 (2006).

Metzker et al., "Termination of DNA synthesis by novel 3'-modified-deoxyribonucleoside 5'-triphosphates" Nucleic Acids Research, 22: 4259-4267 (1994).

Morimoto et al., "Automatic Electrochemical Micro-pH-Stat for Biomicrosystems" Anal. Chem. 80: 905-914 (2008).

Motea et al., "Terminal Deoxynucleotidyl Transferase: The Story of a Misguided DNA Polymerase" Biochim. Biophys. Acta, 1804(5): 1151-1166 (2010).

Needleman et al., "A General Metho Applicable to the Search for Similarities in the Amino Acid Sequence of Two Proteins" J. Mol. Biol., 48: 443-453 (1970).

Rasolonjatovo et al., "Development of a New DNA Sequencing Method: 3'-Ester Cleavage Catalyzed by Taq DNA Polymerase" Nucleosides & Nucleotides, 18(4&5): 1021-1022 (1999).

Schmitz et al., OrganicLett., "Solid-Phase Enzymatic Synthesis of Oligonucleotides" 1(11): 1729-1731 (1999).

Stemmer et al., "Single-step assembly of a gene and entire plasmid from large numbers of oligodeoxyribonucleotides" Gene, 164: 49-53 (1995).

Taunton-Rigby et al., "Oligonucleotide synthesis. III. Enzymically removable acyl protecting groups" J. Org. Chem., 38 (5): 977-985 (1973).

Uemura et al., " Regioselective deprotection of 3',5'-O-acylated pyrimidine nucleosides by lipase and esterase" Tetrahedron Lett., 30(29): 3819-3820 (1989).

Yang et al., "Mutational Analysis of Residues in the Nucleotide Binding Domain of Human Terminal Deoxynucleotidyl Transferase" J. Biol. Chem., 269(16): 11859-11868 (1994).

Leproust, E M, et al. (May 1, 2010). "Synthesis of High-Quality Libraries of Long (150mer) Oligonucleotides by a Novel Depurination Controlled Process," Nucleic Acids Research 38(8):2522-2540.

Xian-Chinese Journal. (2025). "Synthesis of Polynucleotides," Chemical Bulletin, No. 2, p. 79, 4 pages. (Translation of English Abstract Only).

Smith, T.F. et al. (1981). "Identification of Common Molecular Subsequences," J. Mol. Biol. 147:195-197, 4 pages.

U.S. Appl. No. 18/993,240, Title: Method of Purifying Solution Comprising Polynucleotide, filed Jan. 10, 2025, by Mouaadh Kellal (U.S. Patent Application is not submitted herewith pursuant to the waiver of 37 C.F.R. § 1.98(a)(2)(iii) issued by the Office on Sep. 21, 2004.).

U.S. Appl. No. 19/122,511, Title: Methods and Products for Removal of Uracil Containing Polynucleotides, filed Apr. 18, 2025, by Mikhael Soskine (U.S. Patent Application is not submitted herewith pursuant to the waiver of 37 C.F.R. § 1.98(a)(2)(iii) issued by the Office on Sep. 21, 2004.).

U.S. Appl. No. 19/132,344, Title: Variants of Poly(A) Polymerase and Uses Thereof, filed May 22, 2025, by Tillmann Heinisch (U.S. Patent Application is not submitted herewith pursuant to the waiver of 37 C.F.R. § 1.98(a)(2)(iii) issued by the Office on Sep. 21, 2004.).

U.S. Appl. No. 19/136,668, Title: In Vitro Enzymatical RNA Synthesis, filed Jun. 6, 2025, by Tillmann Heinisch (U.S. Patent Application is not submitted herewith pursuant to the waiver of 37 C.F.R. § 1.98(a)(2)(iii) issued by the Office on Sep. 21, 2004.).

U.S. Appl. No. 19/143,773, Title: Variable Viscosity Inks for Inkjet Delivery of Enzyme Reagents, filed Jun. 26, 2025, by Adrian Horgan (U.S. Patent Application is not submitted herewith pursuant to the waiver of 37 C.F.R. § 1.98(a)(2)(iii) issued by the Office on Sep. 21, 2004.).

U.S. Appl. No. 19/144,006, Title: Heat Treatment Means for Printing Device of an Enzymatic Synthesis Apparatus, filed Jun. 27, 2025, by Adrian Horgan (U.S. Patent Application is not submitted herewith pursuant to the waiver of 37 C.F.R. § 1.98(a)(2)(iii) issued by the Office on Sep. 21, 2004.).

U.S. Appl. No. 19/144,778, Title: Methods for Obtaining Correctly Assembled Nucleic Acids, filed Jun. 30, 2025, by Jeffrey Jeddeloh (U.S. Patent Application is not submitted herewith pursuant to the waiver of 37 C.F.R. § 1.98(a)(2)(iii) issued by the Office on Sep. 21, 2004.).

U.S. Appl. No. 19/148,244, Title: Scarless Template-Free Enzymatic Synthesis of Polynucleotides, filed Jul. 15, 2025, by Adrian Horgan (U.S. Patent Application is not submitted herewith pursuant to the waiver of 37 C.F.R. § 1.98(a)(2)(iii) issued by the Office on Sep. 21, 2004.).

U.S. Appl. No. 19/148,524, Title: Inkjet-Assisted Enzymatic Nucleic Acid Synthesis, filed Jul. 16, 2025, by Nicolas Moghaddam (U.S. Patent Application is not submitted herewith pursuant to the waiver of 37 C.F.R. § 1.98(a)(2)(iii) issued by the Office on Sep. 21, 2004.).

U.S. Appl. No. 19/150,746, Title: Enzymatic Synthesis of Polynucleotide Probes, filed Jul. 24, 2025, by Thomas Ybert (U.S. Patent Application is not submitted herewith pursuant to the waiver of 37 C. F.R. § 1.98(a)(2)(iii) issued by the Office on Sep. 21, 2004.).

U.S. Appl. No. 19/241,170, Title: Systems, Apparatus and Kits for Enzymatic Polynucleotide Synthesis, filed Jun. 17, 2025, by Carl Martin (U.S. Patent Application is not submitted herewith pursuant to the waiver of 37 C.F.R. § 1.98(a)(2)(iii) issued by the Office on Sep. 21, 2004.).

INCREASING LONG-SEQUENCE YIELDS IN TEMPLATE-FREE ENZYMATIC SYNTHESIS OF POLYNUCLEOTIDES

CROSS-REFERENCE TO RELATED APPLICATIONS

This application is a 371 of International Application Serial No. PCT/EP2020/076315, filed on Sep. 21, 2020, which application claims priority to EP19199022.5, filed on Sep. 23, 2019, the disclosures of which are incorporated herein by reference in their entirety.

INCORPORATION BY REFERENCE OF SEQUENCE LISTING PROVIDED AS A TEXT FILE

A Sequence Listing is provided herewith in a text file "DNAS-014_SEQ_LIST_revJun2022_ST25" created on Jun. 21, 2022 and having a size of 105,357 bytes. The contents of the text file are incorporated herein by reference in their entirety.

BACKGROUND

Interest in enzymatic approaches to polynucleotide synthesis has recently increased not only because of increased demand for synthetic polynucleotides in many areas, such as synthetic biology, CRISPR-Cas9 applications, and high-throughput sequencing, but also because of the limitations of chemical approaches to polynucleotide synthesis, such as upper limits on product length and the use and needed disposal of organic solvents, Jensen et al, Biochemistry, 57: 1821-1832 (2018). Enzymatic synthesis is attractive because its specificity and efficiency and its requirement of mild aqueous reaction conditions.

Currently, most enzymatic approaches employ a template-free polymerase to repeatedly add 3'-O-blocked nucleoside triphosphates to a single stranded initiator or an elongated strand attached to a support followed by deblocking until a polynucleotide of the desired sequence is obtained. A capping step may also be included. Because these steps—monomer coupling, deblocking and capping—often do not proceed to completion, failure sequences may be generated. Thus, a challenge for most template-free enzymatic synthesis approaches is separating full length final product from the failure sequences.

In view of the above, enzymatic synthesis of polynucleotides would be advanced if improved methods were available for separating full length final product from failure sequences.

SUMMARY OF THE INVENTION

The present invention is directed to methods and kits for template-free enzymatic synthesis of polynucleotides that include steps for reducing or eliminating failure sequences from a final polynucleotide product. In various embodiments, such steps include one or more hybridization-based, nuclease digestion-base, and capture-based sub-steps.

In some embodiments, the invention is directed to methods of synthesizing a polynucleotide having a predetermined sequence comprising the following steps: (a) providing an initiator attached by a 5' end to a solid support and having a 3'-terminal nucleotide with a free 3-hydroxyl; (b) repeating cycles of (i) contacting under elongation conditions the initiator or elongated fragments having free 3'-O-hydroxyls with a 3'-O-blocked nucleoside triphosphate and a template-independent DNA polymerase so that the initiator or elongated fragments are elongated by incorporation of a 3'-O-blocked nucleoside triphosphate to form 3'-O-blocked elongated fragments, and (ii) deblocking the elongated fragments to form elongated fragments having free 3-hydroxyls, until polynucleotides having the predetermined sequences are formed; (c) generating double stranded polynucleotides by annealing primers to the 3'-ends of at least one polynucleotide and extending the primer to create a reverse complement of the polynucleotide; (d) providing reaction conditions with a hybridization stringency that dissociate failure sequences among the double stranded polynucleotides; and (e) digesting strands of the dissociated double stranded polynucleotides.

In some embodiments, the invention is directed to methods of synthesizing a polynucleotide having a predetermined sequence comprising the following steps: a) providing an initiator attached by a 5' end to a solid support and having a 3-terminal nucleotide with a free 3-hydroxyl; b) repeating cycles of (i) contacting under elongation conditions the initiator or elongated fragments having free 3'-O-hydroxyls with a 3'-O-blocked nucleoside triphosphate and a template-independent DNA polymerase so that the initiator or elongated fragments are elongated by incorporation of a 3'-O-blocked nucleoside triphosphate to form 3'-O-blocked elongated fragments, and (ii) deblocking the elongated fragments to form elongated fragments having free 3-hydroxyls, until augmented polynucleotides are formed each comprising a polynucleotide with a common primer binding site at its 3' end; c) generating double stranded augmented polynucleotides by annealing a primer to the common primer binding sites of each augmented polynucleotide and extending the primer to create a reverse complement of the polynucleotide; d) providing reaction conditions with a hybridization stringency so that failure sequences among the double stranded augmented polynucleotides dissociate; and e) digesting strands of the dissociated double stranded augmented polynucleotides.

In some embodiments, the invention is directed to methods of synthesizing a polynucleotide having a predetermined sequence, the method comprising the steps of: a) providing an initiator attached by a 5' end to a solid support and having a 3'-terminal nucleotide with a free 3'-hydroxyl; b) repeating cycles of (i) contacting under elongation conditions the initiator or elongated fragments having free 3'-O-hydroxyls with a 3'-O-blocked nucleoside triphosphate and a template-independent DNA polymerase so that the initiator or elongated fragments are elongated by incorporation of a 3'-O-blocked nucleoside triphosphate to form 3'-O-blocked elongated fragments, and (ii) deblocking the elongated fragments to form elongated fragments having free 3-hydroxyls, until augmented polynucleotides or failure sequences thereof are formed each comprising a polynucleotide with a primer binding site at its 3' end; c) annealing primers to the primer binding sites of the augmented polynucleotides or failure sequences thereof; d) repeating cycles of (i) contacting under primer extension conditions the primers or extended primers having free 3'-O-hydroxyls with a 3'-O-blocked nucleoside triphosphate and a template-dependent DNA polymerase so that the primers or extended primers are extended by incorporation of a 3'-O-blocked nucleoside triphosphate to form a double stranded fragments comprising 3'-O-blocked extended primers, and (ii) deblocking the extended primers to form extended primers having free 3-hydroxyls, until reverse complements of augmented polynucleotides are formed, wherein in said step (i) of contacting, the primers or extended primers are contacted with 3'-0-blocked nucleoside triphosphates in an order identical to that of the reverse complement of the predetermined sequence, thereby forming truncated reverse complements on failure sequences; and e) removing failure sequences by their truncated reverse complements.

In some embodiments, the invention is directed to methods of synthesizing a polynucleotide having a predetermined sequence, the method comprising the steps of: a) providing an initiator attached by a 5' end to a solid support and having a 3'-terminal nucleotide with a free 3'-hydroxyl; b) repeating cycles of (i) contacting under elongation conditions the initiator or elongated fragments having free 3'-O-hydroxyls with a 3'-O-amino nucleoside triphosphate and a template-independent DNA polymerase so that the initiator or elongated fragments are elongated by incorporation of a 3'-O-amino nucleoside triphosphate to form 3'-O-amino elongated fragments, (ii) converting the 3'-O-amino elongated fragments to 3'-oxime-elongated fragments, (iii) treating the elongated fragments with a 3'-exonuclease; (iv) converting 3'-oxime elongated fragments to 3'-O-amino elongated fragments; and (v) deblocking the elongated fragments to form elongated fragments having free 3'-hydroxyls, until polynucleotides having the predetermined sequences are formed.

It is a further purpose of the present invention to provide a kit for enhancing full length polynucleotides synthesized with a template-independent DNA polymerase, the kit comprising: (a) one or more TdT variant for template-independent synthesis of polynucleotides having predetermined sequences, (b) one or more primers to anneal to common primer binding sites of the polynucleotides, (c) a template-dependent polymerase for extending the one or more primers annealed to the common primer binding sites, and (c) one or more single stranded nucleases to digest failure sequences.

DETAILED DESCRIPTION OF THE INVENTION

Figure 1A:
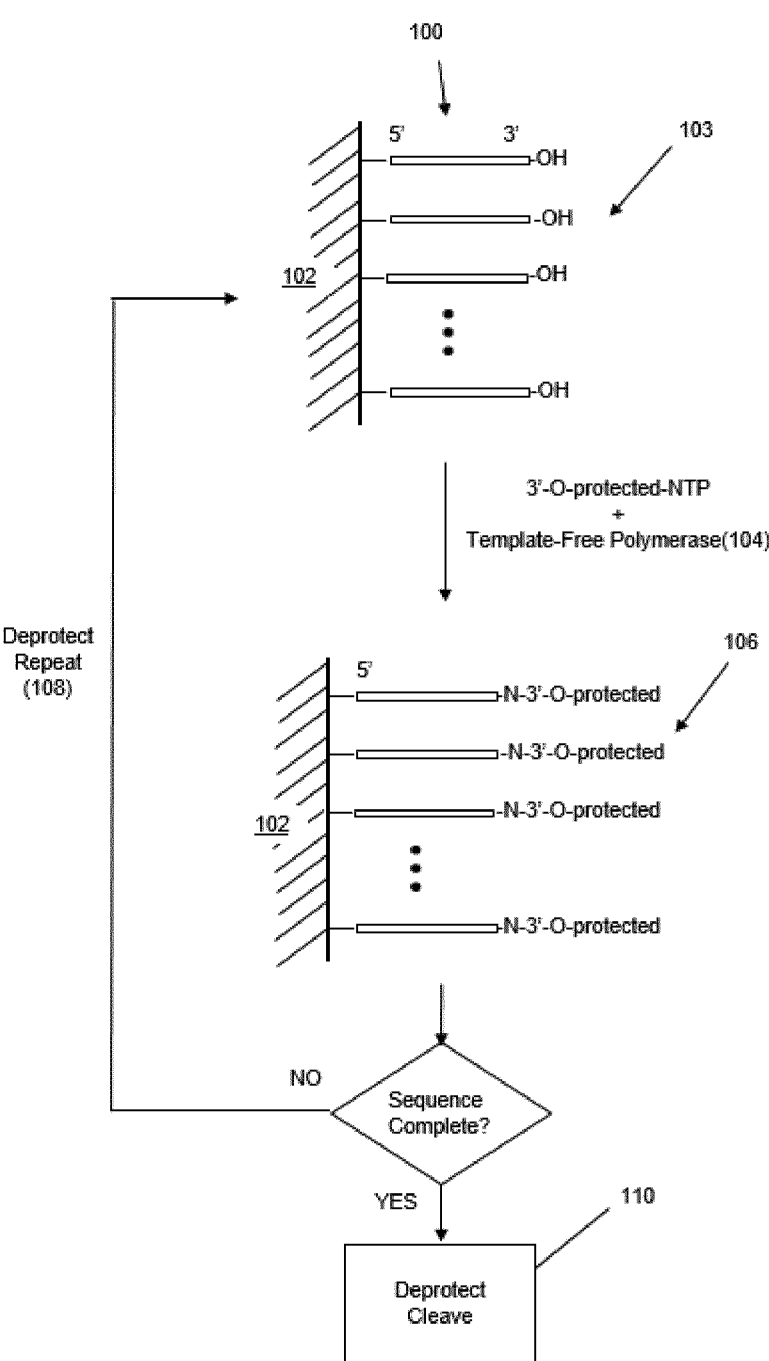
FIGS. 1A and 1B diagrammatically illustrate a method of template-free enzymatic synthesis of a polynucleotide that may be employed as part of the invention.

The general principles of the invention are disclosed in more detail herein particularly by way of examples, such as those shown in the drawings and described in detail. It should be understood, however, that the intention is not to limit the invention to the particular embodiments described. The invention is amenable to various modifications and alternative forms, specifics of which are shown for several embodiments. The intention is to cover all modifications, equivalents, and alternatives falling within the principles and scope of the invention.

The practice of the present invention may employ, unless otherwise indicated, conventional techniques and descriptions of organic chemistry, molecular biology (including recombinant techniques), cell biology, and biochemistry, which are within the skill of the art. Such conventional techniques may include, but are not limited to, preparation and use of synthetic peptides, synthetic polynucleotides, monoclonal antibodies, nucleic acid cloning, amplification, sequencing and analysis, and related techniques. Protocols for such conventional techniques can be found in product literature from manufacturers and in standard laboratory manuals, such as Genome Analysis: A Laboratory Manual Series (Vols. I-IV); PCR Primer: A Laboratory Manual; and Molecular Cloning: A Laboratory Manual (all from Cold Spring Harbor Laboratory Press); Lutz and Bornscheuer, Editors, Protein Engineering Handbook (Wiley-VCH, 2009); Hermanson, Bioconjugate Techniques, Second Edition (Academic Press, 2008); and like references.

Figure 2A:
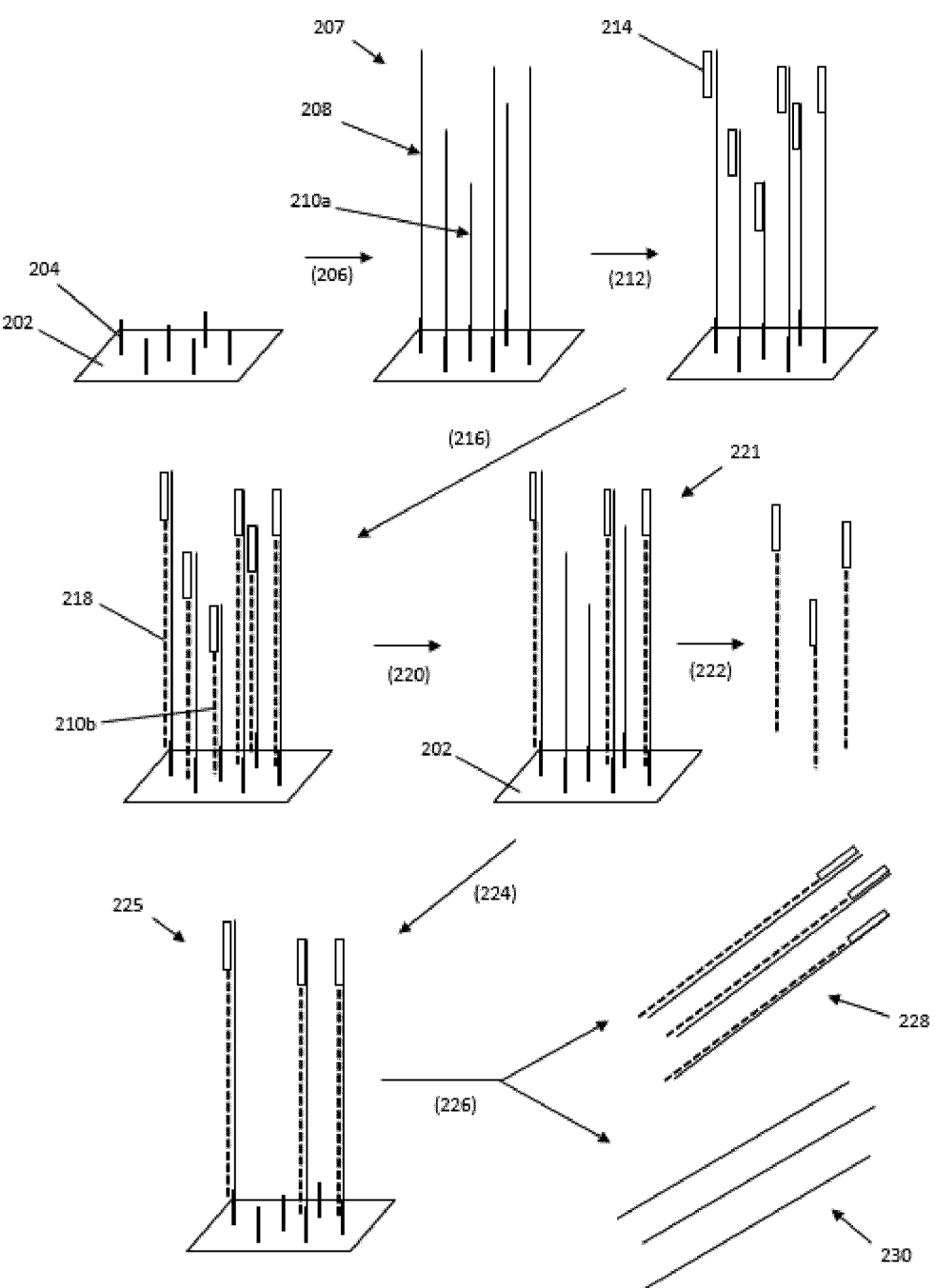
FIG. 2A diagrammatically illustrates an embodiment of the method of invention using hybridization stringency to remove failure sequences.

The invention is directed to methods of template-free enzymatic synthesis of polynucleotides which include steps for reducing the number of failure sequences in a final product. Such steps include, but are not limited to, steps depending on hybridization stringency and nuclease treatments to improve the yield of full length polynucleotides. FIG. 2A illustrates the steps of one embodiment of the invention. Solid support (202) is provided having initiators (204) for carrying out template-free enzymatic polynucleotide synthesis (described more fully below). After synthesis (206), that is, after carrying out a predetermined number of cycles to sequentially incorporate a predetermined sequence of nucleotides, an initial product (207) contains a mixture of polynucleotides comprising full length sequences (208) and failure sequences (210a) that are missing one or more nucleotides because of the failures of incorporation (including incorporation of unblocked dNTP contaminants), deblocking, and/or capping, and the like. While not wishing to be bound by theory, it is believed that another significant source of sequence failures are due to steric hindrance from enzyme denaturation and/or adhesion to the solid supports and/or growing polynucleotide strands, with the consequence that most failure sequences are 3' truncations of the desired sequences; thus, most failure sequences do not have a 3'-end sequence that can serve as a primer binding site and can be distinguished from full length polynucleotides by this property.

To full length polynucleotides, primers (214) may be annealed (212) to their 3'-ends and extended (216) by a template-dependent polymerase in the presence of the four dNTPs to synthesized a reverse complementary strand of the initial products giving double stranded polynucleotide products (218), which may include some failure sequences (210*b*) in double stranded form. The stringency of the reaction mixture is increased (220) until the reverse complements of the failure sequences begin to melt (222) from the initially synthesized strands. The stringency is increased until only full length double stranded polynucleotide product (221) remains on solid support (202). The remaining full length sequences may then be treated (224) with a nuclease that preferentially destroys single stranded DNA (such as the 3' truncated failure sequences), e.g. 3'→5' exonuclease, such as, *E. coli* exonuclease I. Full length strands (225) may then be released from solid support (202) as either double stranded (228) or single stranded (230) product. In some embodiments, primer (214) and its primer binding site may include a type ITs restriction endonuclease site or a nickase site in order to remove the terminal primer binding site from the strand attached to solid support (202). In another embodiment, the primer may be extended with a template-dependent polymerase wherein only single dNTPs is included in each reaction step and the sequence of such dNTPs is determined by the desired predetermined sequence of the full length polynucleotide (e.g. as described for the embodiment of FIG. 3A). Thus, to the extent that the polynucleotide serving as a template contains any deletions or other anomalies, the double stranded portion of the template/extended primer complex will be reduced, thereby permitting failure sequences to be more readily separated from full length sequences by hybridization stringency.

In some embodiments, during synthesis polynucleotides of the desired predetermined sequences may be augmented by synthesizing a common primer binding site to their 3'-ends. For example, such embodiments may be carried out in the following steps: (a) providing an initiator attached by a 5' end to a solid support and having a 3'-terminal nucleotide with a free 3'-hydroxyl; (b) repeating cycles of (i) contacting under elongation conditions the initiator or elongated fragments having free 3'-O-hydroxyls with a 3'-O-blocked nucleoside triphosphate and a template-independent DNA polymerase so that the initiator or elongated fragments are elongated by incorporation of a 3'-O-blocked nucleoside triphosphate to form 3'-O-blocked elongated fragments, and (ii) deblocking the elongated fragments to form elongated fragments having free 3'-hydroxyls, until augmented polynucleotides are formed each comprising a polynucleotide with a common primer binding site at its 3' end; (c) generating double stranded augmented polynucleotides by annealing a primer to the common primer binding sites of each augmented polynucleotide and extending the primer to create a reverse complement of the polynucleotide; (d) providing reaction conditions with a hybridization stringency so that dissociate failure sequences among the double stranded augmented polynucleotides dissociate; and (e) digesting strands of the dissociated double stranded augmented polynucleotides. In further embodiments, the method may include a step of cleaving the common primer binding site from undigested double stranded augmented polynucleotides to produce said polynucleotides of the predetermined sequence. Such cleaving, for example, may be accomplished by designing the common primer binding site to comprise a type IIs restriction endonuclease recognition site in its double stranded form. The primer binding site may be cleaved and the solid support washed to remove the double stranded fragment and endonuclease before releasing the desired polynucleotides from the support.

Figure 2B:
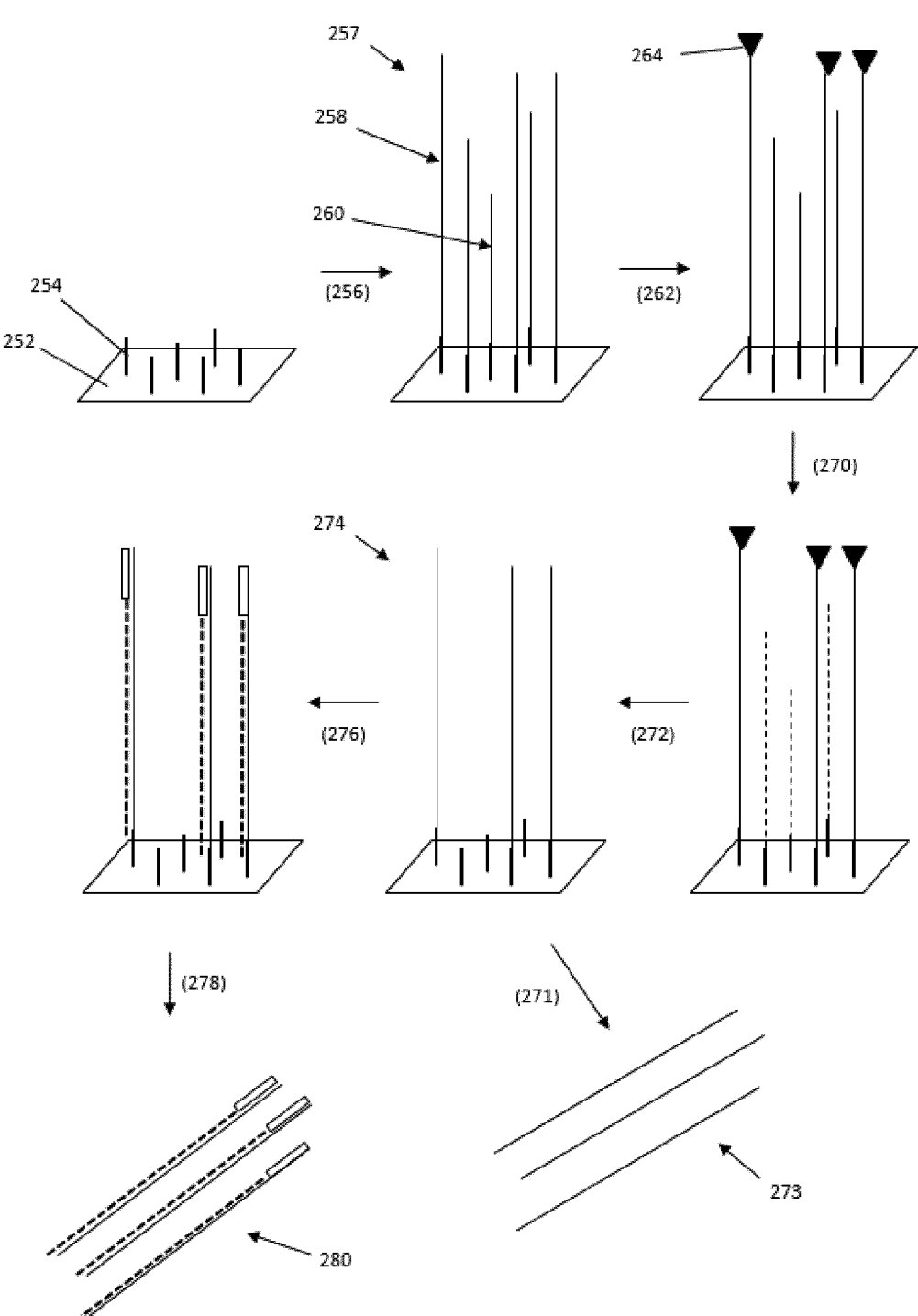
FIG. 2B diagrammatically illustrates methods of the invention using capping and exonuclease treatment to remove failure sequences.
Figure 6:
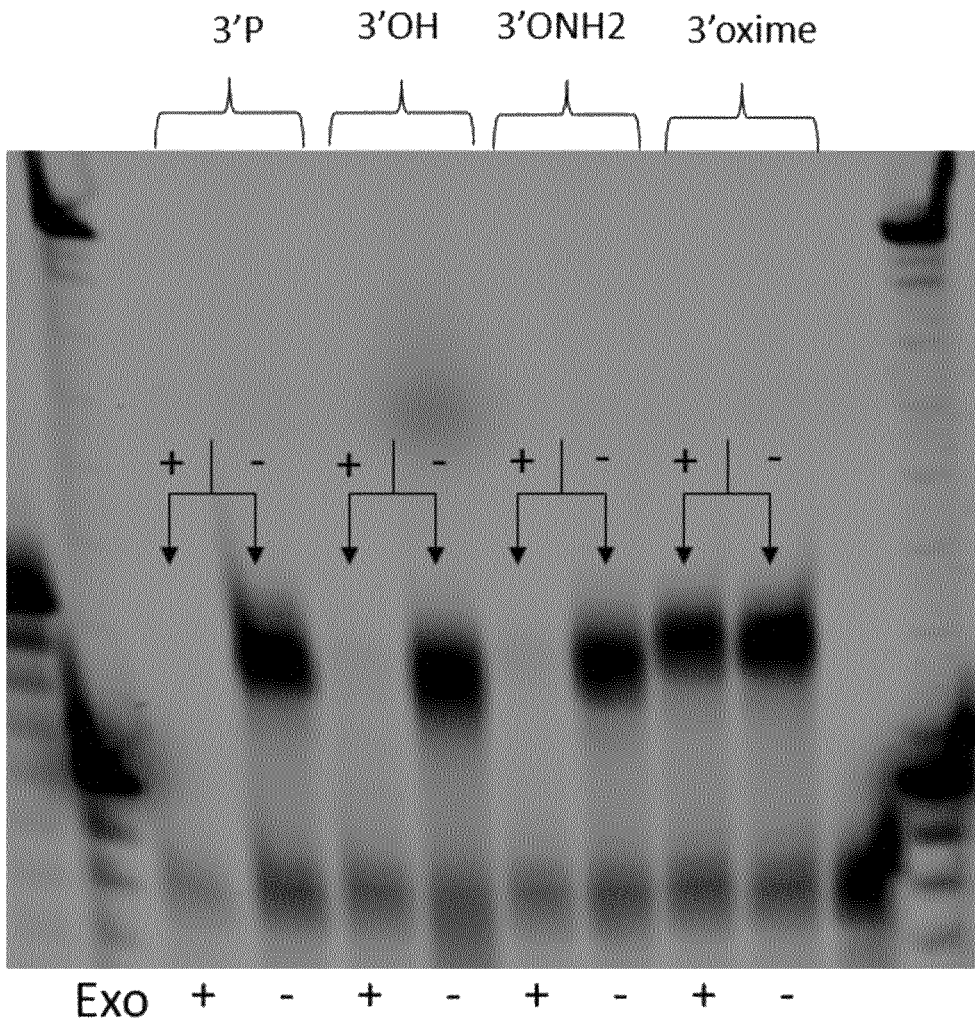
FIG. 6 shows data demonstrating that 3'-oxime groups confer exonuclease resistance.

FIG. 2B illustrates steps of another embodiment of the invention in which full length strands are capped in a final cycle to protect from nuclease digestion after which failure sequences are digested by nuclease treatment, thereby leaving only full length strands. After such digestion, capping moiety (264) may be removed. As above, initiators (254) on solid support (252) are extended (256) by template-free enzymatic synthesis giving product (257) comprising full length polynucleotides (258) and failure sequences as described above (260), which are dominated by 3'-truncations. After a predetermined number of deblocking-incorporation cycles, a final capping step (262) is carried out to add capping moiety (264) to full lengths strands that renders them resistant to 3'→5' exonuclease digestion. In some embodiments, the reaction adding capping moiety (264) is reversible, so that after digestion of failure sequences, capping moiety (264) may be removed to restore a 3'-hydroxyl end. In one aspect of the invention, in embodiments employing 3'-O-amino-dNTP monomers, it has been discovered that the 3'-O-amine moiety may be readily converted into a 3'-oxime moiety (e.g. 50 mM acetone in 50 mM acetate, pH 5) and that the 3'-oxime is resistant to exonuclease treatment (e.g. Thermostable exonuclease I, NEB), as shown by the data in FIG. 6. Moreover, the 3'-O-oxime may be converted back to 3'-O-amine by treatment with methoxylamine or equivalent reagent. The 3'-O-amine may be converted to a 3'-hydroxyl by de-blocking, which in some embodiments, may be carried out in the same reaction mixture by methoxylamine treatment. In other embodiments, a polyA tail may be added as a capping moiety to protect against 3'→5' exonuclease digestion.

Returning to FIG. 2B, after capping (262) non-capped sequences are digested (270) (shown as dashed lines) with a 3'→5' exonuclease after which capping moiety (264) is removed. Full length strands (274) may be released or cleaved (271) from solid support (252) to give single stranded product (273) or they may be converted (276) to double stranded form and released or cleaved (278) to give double stranded product (280). As in the embodiment of FIG. 2A, polynucleotides of this embodiment also may be augmented by synthesizing a common primer binding site to the 3'-ends of the polynucleotides, which may be removed after synthesis is complete, a primer annealed and a complementary strand is produced.

Figure 3A:
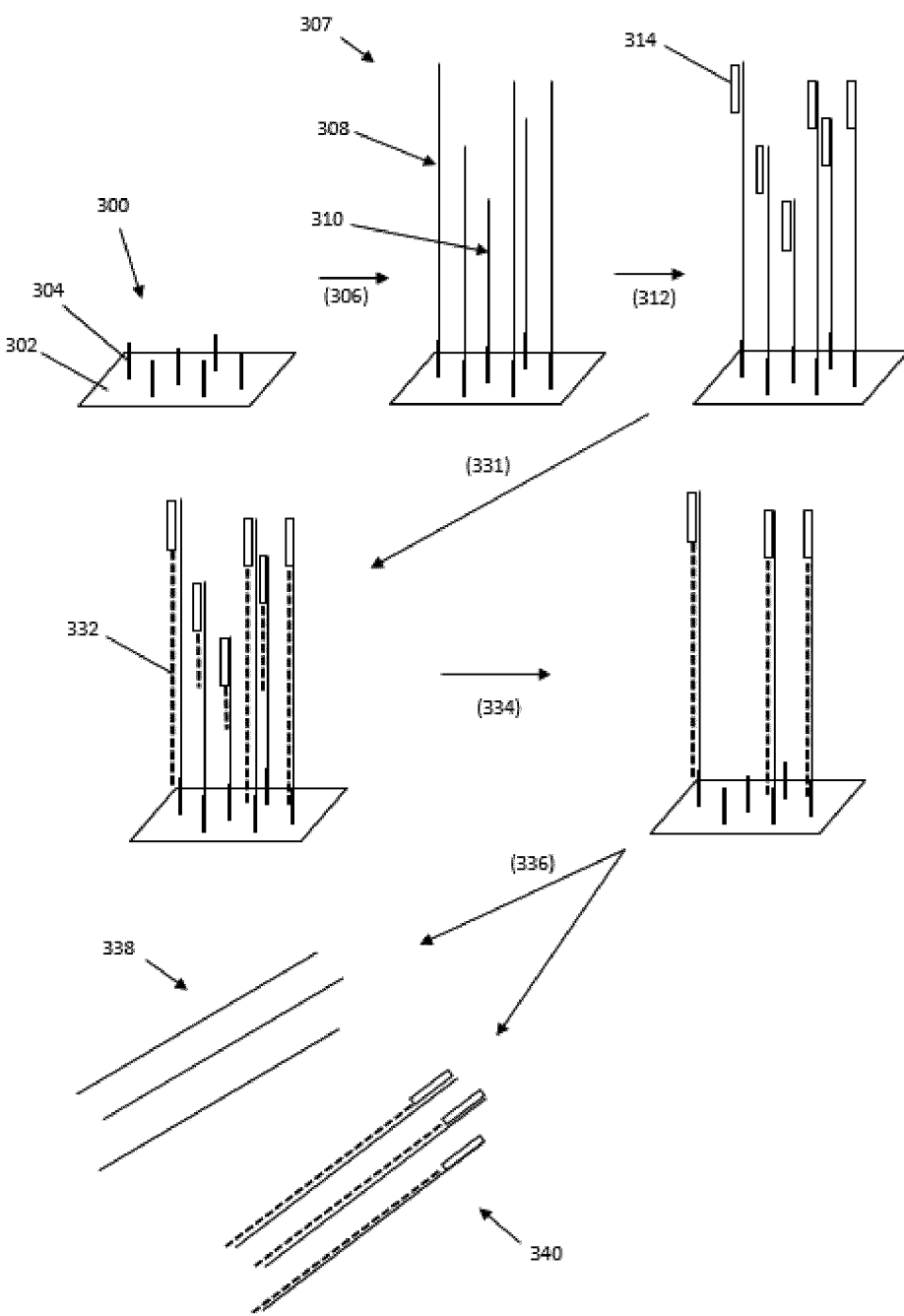
FIGS. 3A-3C diagrammatically illustrate embodiments employing of template-independent synthesis followed by template-dependent re-synthesis of the synthesized strand followed by nuclease digestion of non-fully double stranded product.
Figure 3B:
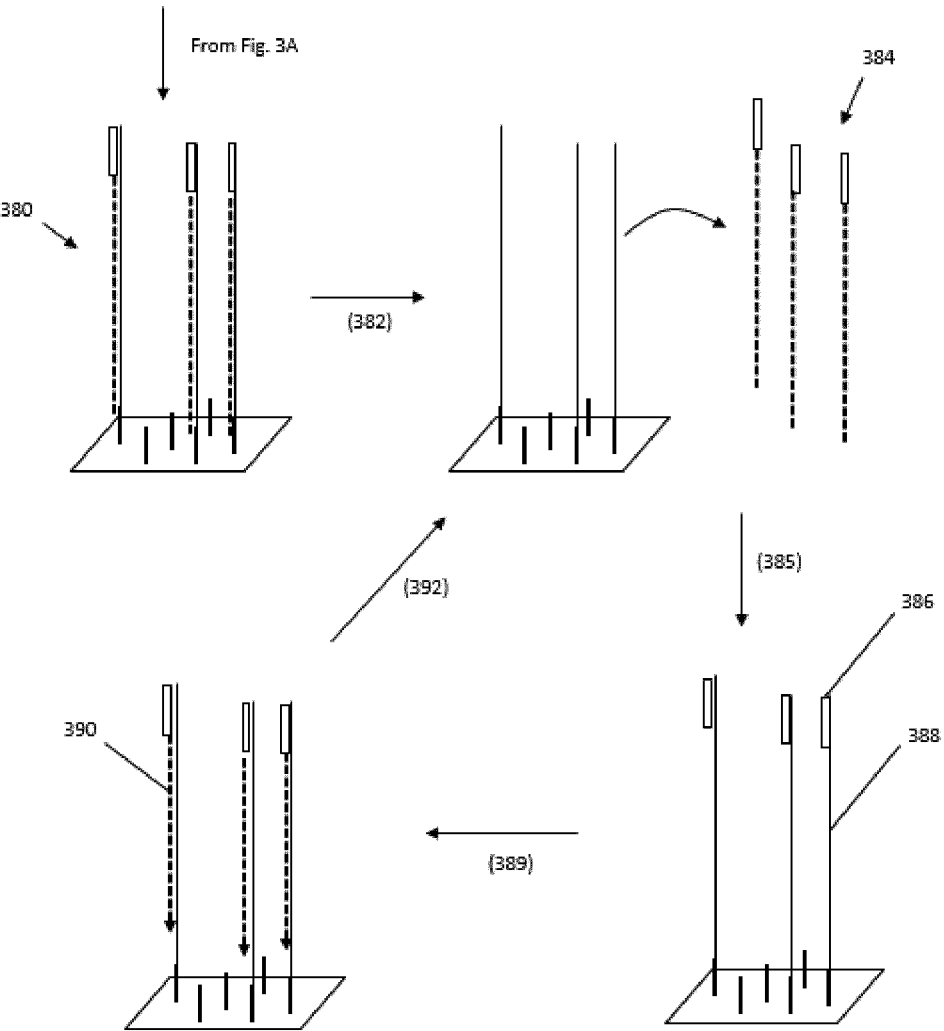

Another embodiment of the invention is illustrated in FIG. 3A. Polynucleotide product (307) is synthesized as described above and primers (314) are anneal to the 3' ends of the newly synthesized strands. Primers (314) are then extended (331) using a template-dependent polymerase with 3'-blocked dNTPs delivered to the extending primers (314) in the reverse complement sequence of the desired sequence of the strands synthesized by template-free synthesis. Since the sequence of 3'-blocked dNTPs exposed to the growing complementary strands is the reverse complement of the desired sequence, as soon as a failure location is reached, the failure sequence acting as a template will become out of phase with the presented 3'-blocked dNTPs, and the reverse complement strand of the failure sequence with truncate, or stop being extended. That is, on a full length polynucleotide serving as a template, the next base may be "A" whereas a failure sequence may be missing the "A" so that no 3'-reversibly protected dTTP will be incorporated. Although the failure sequence may re-start extensions by a fortuitous occurrence of sequence, it will lead to a final extension product that is shorter than that of a full length polynucleotide serving as a template. Only full length sequences (332) with result in full double stranded product. Failure sequences and their truncated complements may be removed (334) from solid support (302) either by melting and/or exonuclease digestion (e.g. exo I, exo T, exo VII) or by treatment with a nonspecific single stranded endonuclease (mung bean, nuclease P1). As above, full length strands (335) may be released (336) as either single stranded (338) or double stranded (340) product. As illustrated in FIG. 3B, full length stands (380) may be used to generate complementary strands by linear amplification. That is, non-covalently attached strands of full length double stranded product (380) may be melted (382) to release complementary strands (384) after which primers (386) may be annealed (385) to covalently attached strands (388) and extended (389) in a conventional template-dependent polymerase extension reaction to form new non-covalently attached product (390). Product (390) may be melted from the covalently attached full length strand and the cycle repeated (392). In some embodiments, a capping step may be implemented in each nucleotide addition cycle. In other embodiments, full length strands may be amplified by solid phase amplification methods, such as bridge PCR, RPA, template walking, or the like. In some such amplifications, solid support (302) may be provided with a population of primers as well as initiators (304). As in the embodiment of FIG. 2A, polynucleotides of this embodiment also may be augmented by synthesizing a common primer binding site to the 3'-ends of the polynucleotides, which may be removed after synthesis is complete, a primer annealed and a complementary strand is produced.

Figure 3C:
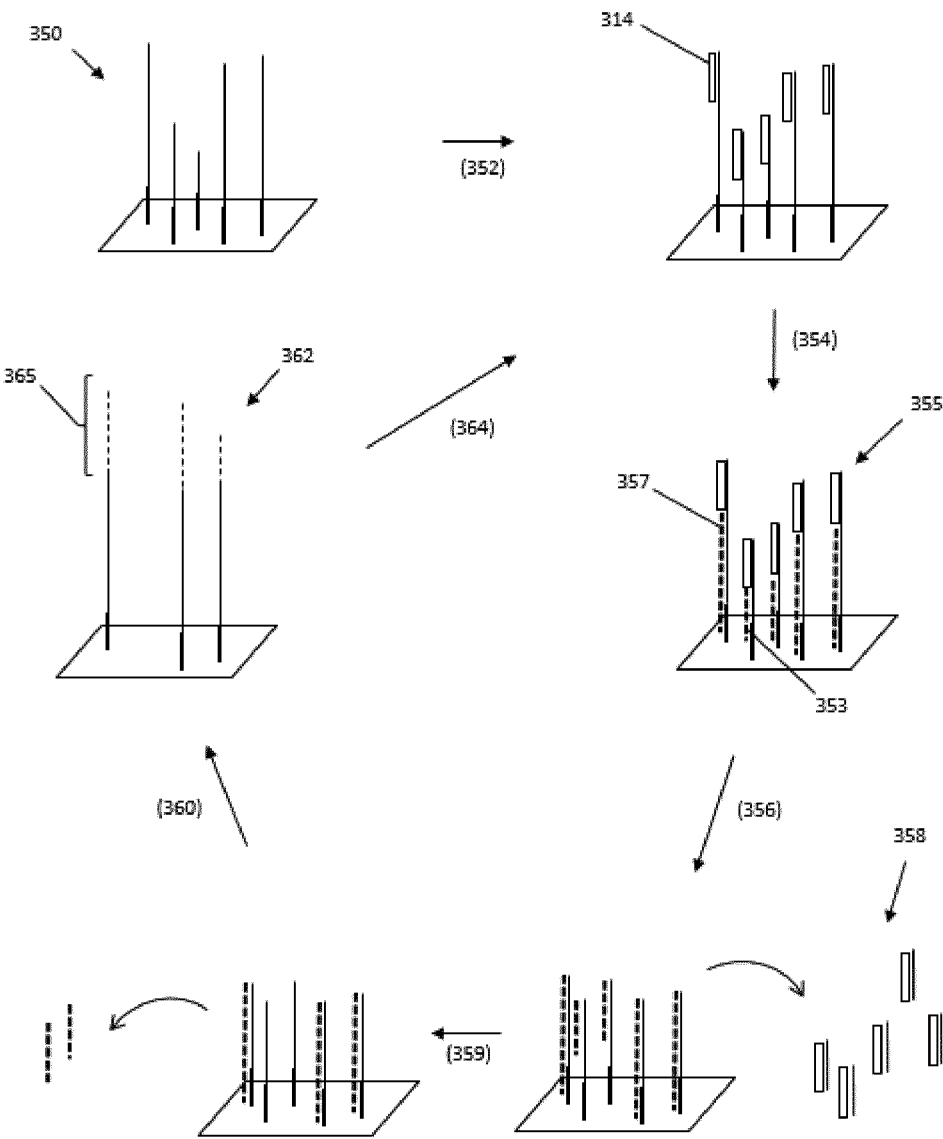

As illustrated in FIG. 3C, the embodiment of FIG. 3A may be carried out by a series of alternating steps of template-free synthesis and template-dependent synthesis. By employing such alternating steps, synthesized strands may be kept relatively short so that differences in melting temperature between full length sequences and failure sequences are maximized. For example, steps of template-free synthesis include up to 10, or up to 20, or up to 30, or up to 40, or up to 50 coupling cycles. In some embodiments, steps of template-free synthesis may include a number of incorporation cycles in the range of from 10 to 50; in other embodiments, the range may be from 10 to 30; in other embodiments, the range may be from 10 to 20. As described above, an initial product (350) is made by template-free enzymatic synthesis after which primers (314) are annealed to the synthesized strands and are extended (354) by a template-dependent polymerase in the presence of 3'-blocked dNTPs to give double stranded products (355). Double stranded products (355) include full length sequences (357) that are completely double stranded and failure sequences (353) that are partially double stranded and partially single stranded. As mentioned above, double stranded products (355) may be processed (356) by preferentially melting complements of the shorter failure sequences followed by single stranded exonuclease treatment, or (as shown) by cleaving primers (314) and its primer binding site (shown as double stranded segments (358) followed by preferential melting (359) and exonuclease treatment to give full length sequences which may be extended by another round of template-free enzymatic synthesis (360) to give, in turn, extended products (362) each comprising new segments (365), which may include new failure sequences. Extended product (362) is then subjected to another cycle (364) of primer annealing, extension, and removal of failure sequences.

In some embodiments, primers employed in the embodiments described in FIGS. 2A-2B, 3A-3C, and related embodiments, may be synthesized on the same arrays as the desired polynucleotides by using orthogonal protection groups on their respective initiators, e.g. using techniques disclosed by Godron et al, International patent publication WO2020/141143. Thus, in some embodiments, primers with sequences tailored for specific polynucleotides may be synthesized in the same reaction mixture. In other embodiments, desired polynucleotides may have their 3'-ends extended by a common primer binding site.

Figure 4A:
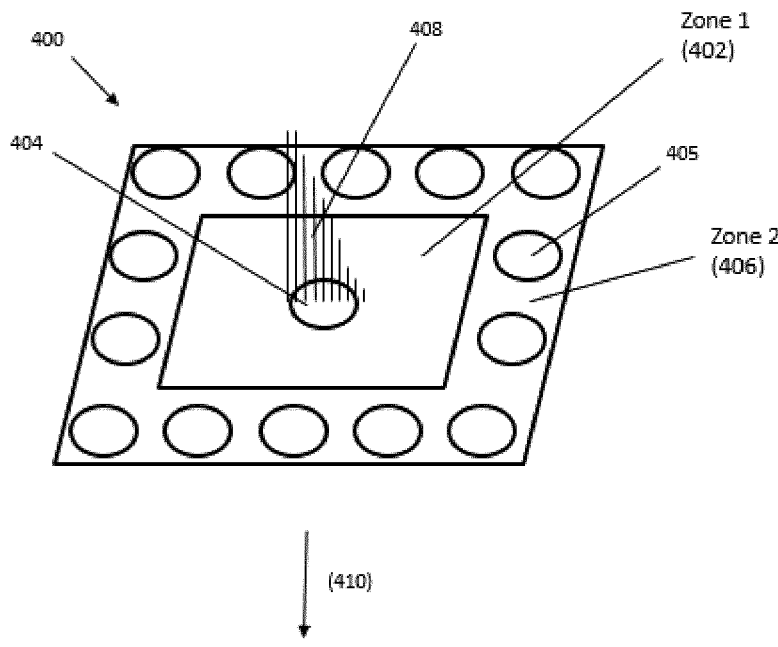
FIGS. 4A-4C illustrate embodiments of the invention employing hybridization capture of full length polynucleotides on arrays.
Figure 4B:
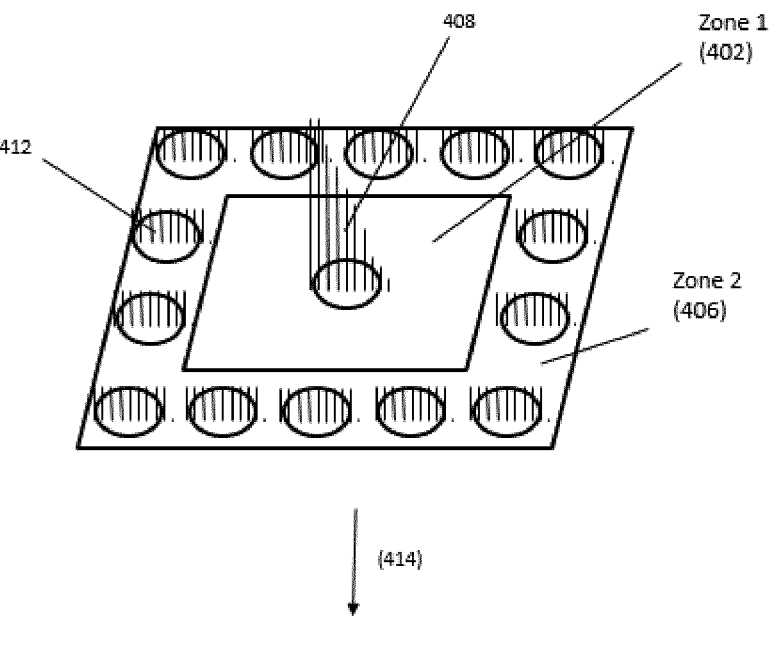
Figure 4C:
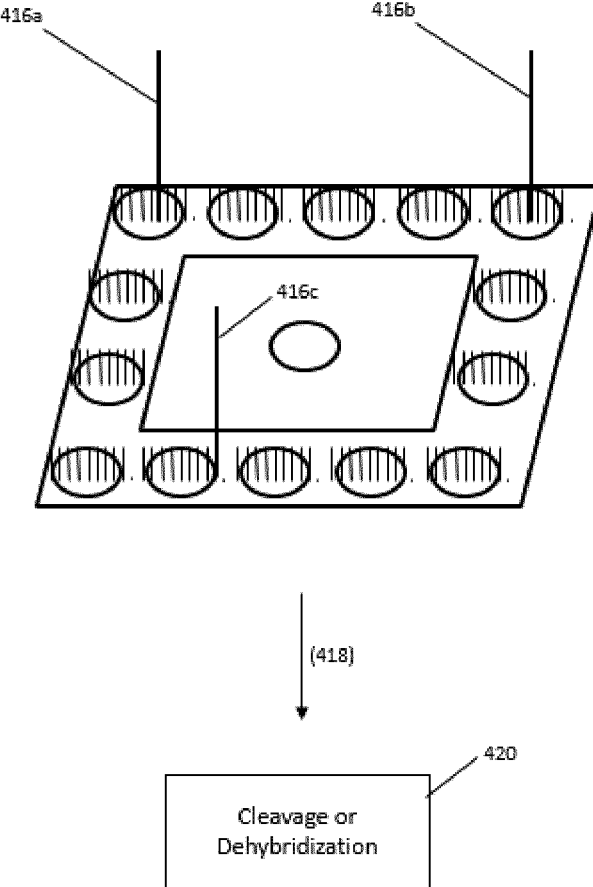

Further embodiments of the invention may be implemented using parallel synthesis on solid supports, such as planar array containing spatially distinct synthesis zones within which different polynucleotides may synthesized, as described more fully below. Such arrays may be used for synthesis and enrichment of full length polynucleotides, as illustrated in FIGS. 4A-4C. FIG. 4A illustrates a subsection of an exemplary planar array (400) comprising central zone 1 (402) with a discrete synthesis site (404) and peripheral zone 2 (406) which comprises one or more distinct synthesis sites (405) from that of zone 1 (402). In accordance with the invention, in other planar arrays discrete synthesis site (404) of zone 1 (402) may cover a different portion of zone 1 (402) than shown (or all of zone 1 (402)) and, likewise, discrete synthesis site(s) (405) may cover different portions of zone 2 (406) than shown (or all of zone 2 (406). The configuration employed is a design choice for the skilled practitioner which depends on the approach to parallel synthesis selected, which, for example, may be based on electrochemistry, photochemistry, or both, for local control of synthesis reactions. In the embodiment of FIGS. 4A-4C, the basic concept is that two regions or zones are formed, a zone 1, which is central, and a zone 2, which surrounds zone 1. With such a configuration, sequences synthesized in and released from zone 1 will diffuse through zone 2, so that polynucleotides of zone 1 may be designed and synthesized to contain a segment of complementary nucleotides to polynucleotides designed and synthesized in zone 2. Thus, after synthesis of polynucleotides in both zones, after release of polynucleotides of zone 1, such released zone 1 polynucleotides may be captured by hybridizing to their complementary sequences in zone 2. By carrying out such operations in parallel on arrays, one may obtain large numbers of different polynucleotides enriched for full length sequences.

Returning to FIG. 4A, as an example of such operation, zone 1 polynucleotide is synthesized to give a product (408), comprising a combination of full length sequences and failure sequences. For example, in a first step, a 300-mer sequence may be synthesized to give a product (408) containing 20% full length sequences and 80% failure sequences. In a second step, a 30-mer sequence (412) complementary to a portion of the sequence of product (408) is synthesized at reaction sites (405) of zone 2 (406). For example, 30-mer product (412) may be 90% pure full length sequence and 10% failure sequences. In some embodiments, the 3' end of polynucleotide (408) is the portion that is complementary to 30-mer product (412). Upon cleavage (414) of product (408) of zone 1 (402) (under condition permitting hybrization), polynucleotides of the product diffuse across zone 2 (406) where a portion of the full length sequences (416a, b, c) are captured by hybridizing to their complementary sequences in zone 2 (406), as shown in FIG. 4C. Alternatively, a similar result may be accomplished by using members of a binding pair attached to molecules of zone 1 and zone 2, such as, biotin and streptavidin, in place of hybridization based selection. For example, in such an alternative, in a final synthesis step the polynucleotides (408) of zone 1 (402) a dNTP derivatized with a biotin may be incorporated, and instead of synthesizing 30-mer complementary polynucleotides (412) in zone 2 (406), a coating of streptavidin may be applied to zone 2 (406). In either case, full length polynucleotides (416*a-c*) may be released (418) by cleavage or dehybridization (420).

Figures 5A, 5B:
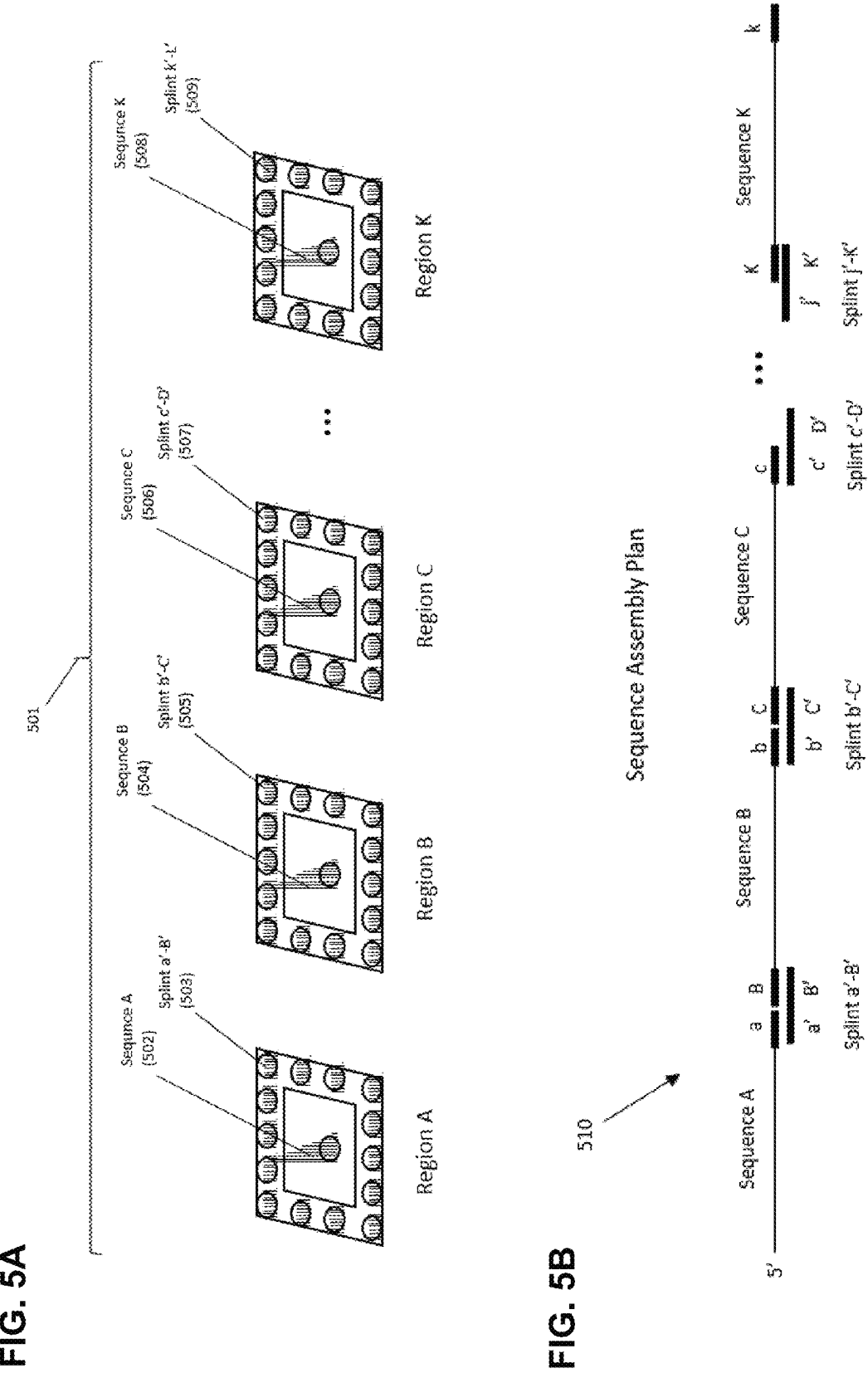
FIGS. 5A-5C illustrate embodiments for producing long fragments by assembling full length polynucleotides on arrays.
Figure 5C:
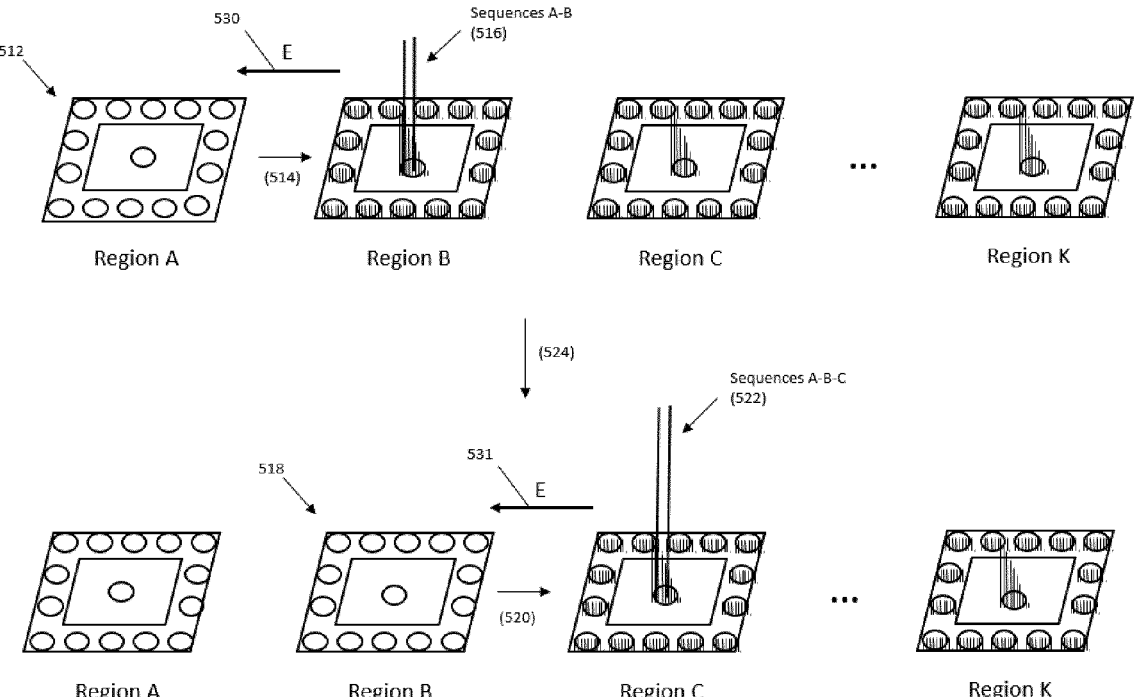

As shown in FIGS. 5A-5C, arrays of FIGS. 4A-4C may be applied to the assembly of a larger polynucleotide ("assembled polynucleotide") from components comprising full length polynucleotides from individual regions. A series of synthesis regions (501) comprising (for example) Region A, Region B, Region C to Region K, may be arranged linearly on an array. In each region, polynucleotide components having Sequence A, Sequence B, Sequence C . . . Sequence K are synthesized at the central synthesis sites (502, 504, 506, . . . 508, respectively) and splint oligonucleotides a'-B', b'-C', c'-D' . . . j'-K' are synthesized at peripheral synthesis sites (503, 505, 507, . . . 509, respectively). Splint oligonucleotides comprise complementary regions to the ends of full length polynucleotides of adjacent regions so that (for example) upon hybridization of polynucleotides of Region A and B to splint oligonucleotide a'-B' in the presence of a ligase, polynucleotides of Region A and B form an intermediate assembled polynucleotide in accordance with a design (510) shown in FIG. 5B. As shown in FIG. 5C, such assembly may be conducted in a stepwise manner after polynucleotides at central synthesis sites are enriched for full length sequences (which may be carried out simultaneously or stepwise prior to each ligation step). A step of such stepwise assembly proceeds as follows: (i) under hybridization conditions and ligation conditions full length polynucleotides of the central synthesis site of a first Region (e.g. Region A) are cleaved and splint oligonucleotides at peripheral synthesis sites of the first Region are cleaved (512), so that both full length sequences and splint oligonucleotides may diffuse (514) to a second Region (e.g. Region B) and form a 3-way complex (516) forms comprising a full length sequence from the first Region, a full length sequence of the second Region (which is still attached to its synthesis site) and a splint oligonucleotide, which (ii) permits ligation of full length sequence of Region A to the 3' end of full length sequences of Region B to form assembly intermediate of Sequence A-B. Diffusion of cleaved sequences may be biased by applying electrical field E (530 and 531) to drive negatively charged polynucleotides and oligonucleotides in the direction of the attached polynucleotides with which they will form complexes. After an assembly intermediate is ligated at a second Region (and optional amplification, e.g. by template walking, or other solid phase amplification method), the above steps are repeated (524) for the next Region, until an assembled polynucleotide is completed.

Template-Free Enzymatic Synthesis

Generally, methods of template-free (or equivalently, "template-independent") enzymatic DNA synthesis comprise repeated cycles of steps, such as are illustrated in FIG. 2, in which a predetermined nucleotide is coupled to an initiator or growing chain in each cycle. The general elements of template-free enzymatic synthesis is described in the following references: Ybert et al, International patent publication WO/2015/159023; Ybert et al, International patent publication WO/2017/216472; Hyman, U.S. Pat. No. 5,436,143; Hiatt et al, U.S. Pat. No. 5,763,594; Jensen et al, Biochemistry, 57: 1821-1832 (2018); Mathews et al, Organic & Biomolecular Chemistry, DOI: 0.1039/ c6ob01371f (2016); Schmitz et al, Organic Lett., 1(11): 1729-1731 (1999).

Initiator polynucleotides (100) are provided, for example, attached to solid support (102), which have free 3'-hydroxyl groups (103). To the initiator polynucleotides (100) (or elongated initiator polynucleotides in subsequent cycles) are added a 3'-O-protected-dNTP and a template-free polymerase, such as a TdT or variant thereof (e.g. Ybert et al, WO/2017/216472; Champion et al, WO2019/135007) under conditions (104) effective for the enzymatic incorporation of the 3'-O-protected-dNTP onto the 3' end of the initiator polynucleotides (100) (or elongated initiator polynucleotides). This reaction produces elongated initiator polynucleotides whose 3'-hydroxyls are protected (106). If the elongated initiator polynucleotide contains a competed sequence, then the 3'-O-protection group may be removed, or deprotected, and the desired sequence may be cleaved from the original initiator polynucleotide. Such cleavage may be carried out using any of a variety of single strand cleavage techniques, for example, by inserting a cleavable nucleotide at a predetermined location within the original initiator polynucleotide. An exemplary cleavable nucleotide may be a uracil nucleotide which is cleaved by uracil DNA glycosylase. If the elongated initiator polynucleotide does not contain a completed sequence, then the 3'-O-protection groups are removed to expose free 3'-hydroxyls (103) and the elongated initiator polynucleotides are subjected to another cycle of nucleotide addition and deprotection.

As used herein, the terms "protected" and "blocked" in reference to specified groups, such as, a 3'-hydroxyls of a nucleotide or a nucleoside, are used interchangeably and are intended to mean a moiety is attached covalently to the specified group that prevents a chemical change to the group during a chemical or enzymatic process. Whenever the specified group is a 3'-hydroxyl of a nucleoside triphosphate, or an extended fragment (or "extension intermediate") in which a 3'-protected (or blocked)-nucleoside triphosphate has been incorporated, the prevented chemical change is a further, or subsequent, extension of the extended fragment (or "extension intermediate") by an enzymatic coupling reaction.

As used herein, an "initiator" (or equivalent terms, such as, "initiating fragment," "initiator nucleic acid," "initiator oligonucleotide," or the like) usually refers to a short oligonucleotide sequence with a free 3'-end, which can be further elongated by a template-free polymerase, such as TdT. In one embodiment, the initiating fragment is a DNA initiating fragment. In an alternative embodiment, the initiating fragment is an RNA initiating fragment. In some embodiments, an initiating fragment possesses between 3 and 100 nucleotides, in particular between 3 and 20 nucleotides. In some embodiments, the initiating fragment is single-stranded. In alternative embodiments, the initiating fragment is double-stranded. In some embodiments, an initiator may comprise a non-nucleic acid compound having a free hydroxyl to which a TdT may couple a 3'-O-protected dNTP, e.g. Baiga, U.S. patent publications US2019/0078065 and US2019/0078126.

In some embodiments, an initiator may comprise a non-nucleic acid compound having a free hydroxyl to which a TdT may couple a 3'-O-protected dNTP, e.g. Baiga, U.S. patent publications US2019/0078065 and US2019/0078126.

After synthesis is completed polynucleotides with the desired nucleotide sequence may be released from initiators and the solid supports by cleavage. A wide variety of cleavable linkages or cleavable nucleotides may be used for this purpose. In some embodiments, cleaving the desired polynucleotide leaves a natural free 5'-hydroxyl on a cleaved strand; however, in alternative embodiments, a cleaving step may leave a moiety, e.g. a 5'-phosphate, that may be removed in a subsequent step, e.g. by phosphatase treatment. Cleaving steps may be carried out chemically, thermally, enzymatically or by photochemical methods. In some embodiments, cleavable nucleotides may be nucleotide analogs such as deoxyuridine or 8-oxo-deoxyguanosine that are recognized by specific glycosylases (e.g. uracil deoxyglycosylase followed by endonuclease VIII, and 8-oxoguanine DNA glycosylase, respectively). In some embodiments, cleavage may be accomplished by providing initiators with a deoxyinosine as the penultimate 3' nucleotide, which may be cleaved by endonuclease V at the 3' end of the initiator leaving a 5'-phosphate on the released polynucleotide. Further methods for cleaving single stranded polynucleotides are disclosed in the following references, which are incorporated by reference: U.S. Pat. Nos. 5,739,386, 5,700,642 and 5,830,655; and U.S. Patent Publication Nos. 2003/0186226 and 2004/0106728; and in Urdea and Horn, U.S. Pat. No. 5,367,066.

In some embodiments, cleavage by glycosylases and/or endonucleases may require a double stranded DNA substrate.

Returning to FIG. 1A, in some embodiments, an ordered sequence of nucleotides are coupled to an initiator nucleic acid using a template-free polymerase, such as TdT, in the presence of 3'-O-protected dNTPs in each synthesis step. In some embodiments, the method of synthesizing an oligonucleotide comprises the steps of (a) providing an initiator having a free 3'-hydroxyl (100); (b) reacting under extension conditions (104) the initiator or an extension intermediate having a free 3'-hydroxyl with a template-free polymerase in the presence of a 3'-O-protected nucleoside triphosphate to produce a 3'-O-protected extension intermediate (106); (c) deprotecting the extension intermediate to produce an extension intermediate with a free 3'-hydroxyl (108); and (d) repeating steps (b) and (c) (110) until the polynucleotide is synthesized. (Sometimes the terms "extension intermediate" and "elongation fragment" are used interchangeably). In some embodiments, an initiator is provided as an oligonucleotide attached to a solid support, e.g. by its 5' end. The above method may also include washing steps after the reaction, or extension, step, as well as after the de-protecting step. For example, the step of reacting may include a sub-step of removing unincorporated nucleoside triphosphates, e.g. by washing, after a predetermined incubation period, or reaction time. Such predetermined incubation periods or reaction times may be a few seconds, e.g. 30 sec, to several minutes, e.g. 30 min.

When the sequence of polynucleotides on a synthesis support includes reverse complementary subsequences, secondary intra-molecular or cross-molecular structures may be created by the formation of hydrogen bonds between the reverse complementary regions. In some embodiments, base protecting moieties for exocyclic amines are selected so that hydrogens of the protected nitrogen cannot participate in hydrogen bonding, thereby preventing the formation of such secondary structures. That is, base protecting moieties may be employed to prevent the formation of hydrogen bonds, such as are formed in normal base pairing, for example, between nucleosides A and T and between G and C. At the end of a synthesis, the base protecting moieties may be removed and the polynucleotide product may be cleaved from the solid support, for example, by cleaving it from its initiator.

In addition to providing 3'-O-blocked dNTP monomers with base protection groups, elongation reactions may be performed at higher temperatures using thermal stable template-free polymerases. For example, a thermal stable template-free polymerase having activity above 40° C. may be employed; or, in some embodiments, a thermal stable template-free polymerase having activity in the range of from 40-85° C. may be employed; or, in some embodiments, a thermal stable template-free polymerase having activity in the range of from 40-65° C. may be employed.

In some embodiments, elongation conditions may include adding solvents to an elongation reaction mixture that inhibit hydrogen bonding or base stacking. Such solvents include water miscible solvents with low dielectric constants, such as dimethyl sulfoxide (DMSO), methanol, and the like. Likewise, in some embodiments, elongation conditions may include the provision of chaotropic agents that include, but are not limited to, n-butanol, ethanol, guanidinium chloride, lithium perchlorate, lithium acetate, magnesium chloride, phenol, 2-propanol, sodium dodecyl sulfate, thiourea, urea, and the like. In some embodiments, elongation conditions include the presence of a secondary-structure-suppressing amount of DMSO. In some embodiments, elongation conditions may include the provision of DNA binding proteins that inhibit the formation of secondary structures, wherein such proteins include, but are not limited to, single-stranded binding proteins, helicases, DNA glycolases, and the like.

3'-O-blocked dNTPs without base protection may be purchased from commercial vendors or synthesized using published techniques, e.g. U.S. Pat. No. 7,057,026; Guo et al, Proc. Natl. Acad. Sci., 105(27): 9145-9150 (2008); Benner, U.S. Pat. Nos. 7,544,794 and 8,212,020; International patent publications WO2004/005667, WO91/06678; Canard et al, Gene (cited herein); Metzker et al, Nucleic Acids Research, 22: 4259-4267 (1994); Meng et al, J. Org. Chem., 14: 3248-3252 (3006); U.S. patent publication 2005/037991. 3'-O-blocked dNTPs with base protection may be synthesized as described below.

When base-protected dNTPs are employed the above method of FIG. 1A may further include a step (e) removing base protecting moieties, which in the case of acyl or amidine protection groups may (for example) include treating with concentrated ammonia.

The above method may also include one or more capping steps in addition to washing steps after the reacting, or extending, step A first capping step may cap, or render inert to further extensions, unreacted 3'-OH groups on partially synthesized polynucleotides. Such capping step is usually implemented after a coupling steps, and whenever a capping compound is used, it is selected to be unreactive with protection groups of the monomer just coupled to the growing strands. In some embodiments, such capping steps may be implemented by coupling (for example, by a second enzymatic coupling step) a capping compound that renders the partially synthesized polynucleotide incapable of further couplings, e.g. with TdT. Such capping compounds may be a dideoxynucleoside triphosphate. In other embodiments, non-extended strands with free 3'-hydroxyls may be degraded by treating them with a 3'-exonuclease activity, e.g. Exo I. For example, see Hyman, U.S. Pat. No. 5,436,143. Likewise, in some embodiments, strands that fail to be deblocked may be treated to either remove the strand or render it inert to further extensions. A second capping step may be implemented after a deprotection step, to render the affected strands inert from any subsequent coupling or deprotection any 3'-O protection, or blocking groups. Capping compounds of such second capping step are selected so that they do not react with free 3'-hydroxyls that may be present. In some embodiments, such second capping compound may be a conjugate of an aldehyde group and a hydrophobic group. The latter group permits separation based on hydrophobicity, e.g. Andrus, U.S. Pat. No. 5,047,524.

In some embodiments, reaction conditions for an extension or elongation step may comprising the following: 2.0 μM purified TdT; 125-600 μM 3'-O-blocked dNTP (e.g. 3'-O—NH$_2$-blocked dNTP); about 10 to about 500 mM potassium cacodylate buffer (pH between 6.5 and 7.5) and from about 0.01 to about 10 mM of a divalent cation (e.g. CoCl$_2$ or MnCl$_2$), where the elongation reaction may be carried out in a 50 μL reaction volume, at a temperature within the range RT to 45° C., for 3 minutes. In embodiments, in which the 3'-O-blocked dNTPs are 3'-O—NH$_2$-blocked dNTPs, reaction conditions for a deblocking step may comprise the following: 700 mM NaNO$_2$; 1 M sodium acetate (adjusted with acetic acid to pH in the range of 4.8-6.5), where the deblocking reaction may be carried out in a 50 μL volume, at a temperature within the range of RT to 45° C. for 30 seconds to several minutes.

Depending on particular applications, the steps of deblocking and/or cleaving may include a variety of chemical or physical conditions, e.g. light, heat, pH, presence of specific reagents, such as enzymes, which are able to cleave a specified chemical bond. Guidance in selecting 3'-O-blocking groups and corresponding de-blocking conditions may be found in the following references, which are incorporated by reference: Benner, U.S. Pat. Nos. 7,544,794 and 8,212,020; 5,808,045; 8,808,988; International patent publication WO91/06678; and references cited below. In some embodiments, the cleaving agent (also sometimes referred to as a de-blocking reagent or agent) is a chemical cleaving agent, such as, for example, dithiothreitol (DTT). In alternative embodiments, a cleaving agent may be an enzymatic cleaving agent, such as, for example, a phosphatase, which may cleave a 3'-phosphate blocking group. It will be understood by the person skilled in the art that the selection of deblocking agent depends on the type of 3'-nucleotide blocking group used, whether one or multiple blocking groups are being used, whether initiators are attached to living cells or organisms or to solid supports, and the like, that necessitate mild treatment. For example, a phosphine, such as tris(2-carboxyethyl)phosphine (TCEP) can be used to cleave a 3'O-azidomethyl groups, palladium complexes can be used to cleave a 3'O-allyl groups, or sodium nitrite can be used to cleave a 3'O-amino group. In particular embodiments, the cleaving reaction involves TCEP, a palladium complex or sodium nitrite, e.g. see U.S. Pat. No. 8,212,020, which is incorporated herein by reference.

As noted above, in some embodiments it is desirable to employ two or more blocking groups that may be removed using orthogonal de-blocking conditions. The following exemplary pairs of blocking groups may be used in parallel synthesis embodiments. It is understood that other blocking group pairs, or groups containing more than two, may be available for use in these embodiments of the invention.

| | |
|---|---|
| 3'-O-NH2 | 3'-O-azidomethyl |
| 3'-O-NH2 | 3'-O-allyl, 3'-O-propargyl |
| 3'-O-NH2 | 3'-O-phosphate |
| 3'-O-azidomethyl | 3'-O-allyl, 3'-O-propargyl |
| 3'-O-azidomethyl | 3'-O-phosphate |
| 3'-O-allyl, 3'-O-propargyl | 3'-O-phosphate |

Synthesizing oligonucleotides on living cells requires mild deblocking, or deprotection, conditions, that is, conditions that do not disrupt cellular membranes, denature proteins, interfere with key cellular functions, or the like. In some embodiments, deprotection conditions are within a range of physiological conditions compatible with cell survival. In such embodiments, enzymatic deprotection is desirable because it may be carried out under physiological conditions. In some embodiments specific enzymatically removable blocking groups are associated with specific enzymes for their removal. For example, ester- or acyl-based blocking groups may be removed with an esterase, such as acetylesterase, or like enzyme, and a phosphate blocking group may be removed with a 3' phosphatase, such as T4 polynucleotide kinase. By way of example, 3'-O-phosphates may be removed by treatment with as solution of 100 mM Tris-HCl (pH 6.5) 10 mM MgCl$_2$, 5 mM 2-mercaptoethanol, and one Unit T4 polynucleotide kinase. The reaction proceeds for one minute at a temperature of 37° C.

A "3'-phosphate-blocked" or "3'-phosphate-protected" nucleotide refers to nucleotides in which the hydroxyl group at the 3-position is blocked by the presence of a phosphate containing moiety. Examples of 3-phosphate-blocked nucleotides in accordance with the invention are nucleotidyl-3'-phosphate monoester/nucleotidyl-2',3'-cyclic phosphate, nuclcotidyl-2'-phosphate monoester and nucleotidyl-2' or 3'-alkylphosphate diester, and nucleotidyl-2' or 3-pyrophosphate. Thiophosphate or other analogs of such compounds can also be used, provided that the substitution does not prevent dephosphorylation resulting in a free 3'-OH by a phosphatase.

Further examples of synthesis and enzymatic deprotection of 3'-O-ester-protected dNTPs or 3'-O-phosphate-protected dNTPs are described in the following references: Canard et al, Proc. Natl. Acad. Sci., 92:10859-10863 (1995); Canard et al, Gene, 148: 1-6 (1994); Cameron et al, Biochemistry, 16(23): 5120-5126 (1977); Rasolonjatovo et al, Nucleosides & Nucleotides, 18(4&5): 1021-1022 (1999); Ferrero et al, Monatshefte für Chemie, 131: 585-616 (2000); Taunton-Rigby et al, J. Org. Chem., 38(5): 977-985 (1973); Uemura et al, Tetrahedron Lett., 30(29): 3819-3820 (1989); Becker et al, J. Biol. Chem., 242(5): 936-950 (1967); Tsien, International patent publication WO1991/006678.

In some embodiments, the modified nucleotides comprise a modified nucleotide or nucleoside molecule comprising a purine or pyrimidine base and a ribose or deoxyribose sugar moiety having a removable 3'-OH blocking group covalently attached thereto, such that the 3' carbon atom has attached a group of the structure:

—O—Z wherein —Z is any of —C(R')$_2$—O—R", —C(R')$_2$—N(R")$_2$, —C(R')$_2$—N(H)R", —C(R')$_2$—S—R" and —C(R')$_2$—F, wherein each R" is or is part of a removable protecting group; each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group; with the proviso that in some embodiments such substituents have up to 10 carbon atoms and/or up to 5 oxygen or nitrogen heteroatoms; or (R')$_2$ represents a group of formula =C(R''')$_2$ wherein each R''' may be the same or different and is selected from the group comprising hydrogen and halogen atoms and alkyl groups, with the proviso that in some embodiments the alkyl of each R''' has from 1 to 3 carbon atoms; and wherein the molecule may be reacted to yield an intermediate in which each R" is exchanged for H or, where Z is —(R')$_2$—F, the F is exchanged for OH, SH or NH$_2$, preferably OH, which intermediate dissociates under aqueous conditions to afford a molecule with a free 3'-OH; with the proviso that where Z is —C(R')$_2$—S—R", both R' groups are not H. In certain embodiments, R' of the modified nucleotide or nucleoside is an alkyl or substituted alkyl, with the proviso that such alkyl or substituted alkyl has from 1 to 10 carbon atoms and from 0 to 4 oxygen or nitrogen heteroatoms. In certain embodiments, —Z of the modified nucleotide or nucleoside is of formula —C(R')$_2$—N3. In certain embodiments, Z is an azidomethyl group.

In some embodiments, Z is a cleavable organic moiety with or without heteroatoms having a molecular weight of 200 or less. In other embodiments, Z is a cleavable organic moiety with or without heteroatoms having a molecular weight of 100 or less. In other embodiments, Z is a cleavable organic moiety with or without heteroatoms having a molecular weight of 50 or less. In some embodiments, Z is an enzymatically cleavable organic moiety with or without heteroatoms having a molecular weight of 200 or less. In other embodiments, Z is an enzymatically cleavable organic moiety with or without heteroatoms having a molecular weight of 100 or less. In other embodiments, Z is an enzymatically cleavable organic moiety with or without heteroatoms having a molecular weight of 50 or less. In other embodiments, Z is an enzymatically cleavable ester group having a molecular weight of 200 or less. In other embodiments, Z is a phosphate group removable by a 3'-phosphatase. In some embodiments, one or more of the following 3'-phosphatases may be used with the manufacturer's recommended protocols: T4 polynucleotide kinase, calf intestinal alkaline phosphatase, recombinant shrimp alkaline phosphatase (e.g. available from New England Biolabs, Beverly, MA).

In a further embodiment, the 3'-blocked nucleotide triphosphate is blocked by either a 3'-O-azidomethyl, 3'-O—NH$_2$ or 3'-O-allyl group. In other embodiments, 3'-O-blocking groups of the invention include 3'-O-methyl, 3'-O-(2-nitrobenzyl), 3'-O-allyl, 3'-O-amine, 3'-O-azidomethyl, 3'-O-tert-butoxy ethoxy, 3'-O-(2-cyanoethyl), 3'-O-nitro, and 3'-O-propargyl. In other embodiments, the 3'-blocked nucleotide triphosphate is blocked by either a 3'-O-azidomethyl or a 3'-O—NH$_2$. Synthesis and use of such 3'-blocked nucleoside triphosphates are disclosed in the following references: U.S. Pat. Nos. 9,410,197; 8,808,988; 6,664,097; 5,744,595; 7,544,794; 8,034,923; 8,212,020; 10472383; Guo et al, Proc. Natl. Acad. Sci., 105(27): 9145-9150 (2008); and like references.

In some embodiments, 3'-O-protection groups are electrochemically labile groups. That is, deprotection or cleavage of the protection group is accomplished by changing the electrochemical conditions in the vicinity of the protection group which result in cleavage. Such changes in electrochemical conditions may be brought about by changing or applying a physical quantity, such as a voltage difference or light to activate auxiliary species which, in turn, cause changes in the electrochemical conditions at the site of the protection group, such as an increase or decrease in pH. In some embodiments, electrochemically labile groups include, for example, pH-sensitive protection groups that are cleaved whenever the pH is changed to a predetermined value. In other embodiments, electrochemically labile groups include protecting groups which are cleaved directly whenever reducing or oxidizing conditions are changed, for example, by increasing or decreasing a voltage difference at the site of the protection group.

TdT Variants

A variety of different template-free polymerases are available for use in methods of synthesis implement by systems and apparatus of the invention. Template-free polymerases include, but are not limited to, polX family polymerases (including DNA polymerases β, λ and μ), poly(A) polymerases (PAPs), poly(U) polymerases (PUPs), DNA polymerase θ, and the like, for example, described in the following references: Ybert et al, International patent publication WO2017/216472; Champion et al, U.S. patent Ser. No. 10/435,676; Champion et al, International patent publication WO2020/099451; Yang et al, J. Biol. Chem., 269 (16): 11859-11868 (1994); Motea et al, Biochim. Biophys. Acta, 1804(5): 1151-1166 (2010). In particular, terminal deoxynucleotidyltransferases (TdTs) and its variants are useful in template-free DNA synthesis, especially in inkjet assisted synthesis of polynucleotides.

In some embodiments, enzymatic synthesis methods employ TdT variants that display increased incorporation activity with respect to 3'-O-modified nucleoside triphosphates. For example, such TdT variants may be produced using techniques described in Champion et al, U.S. patent Ser. No. 10/435,676, which is incorporated herein by reference. In some embodiments, a TdT variant is employed having an amino acid sequence at least 60 percent identical to a TdT having an amino acid sequence of any of SEQ ID NOs 2-31 and one or more of the substitutions listed in Table 1, wherein the TdT variant (i) is capable of synthesizing a nucleic acid fragment without a template and (ii) is capable of incorporating a 3'-O-modified nucleotide onto a free 3'-hydroxyl of a nucleic acid fragment. In some embodiments, the above TdT variants include a substitution at every position listed in Table 1. In some embodiments, the above percent identity value is at least 80 percent identity with the indicated SEQ ID NOs; in some embodiments, the above percent identity value is at least 90 percent identity with the indicated SEQ ID NOs; in some embodiments, the above percent identity value is at least 95 percent identity with the indicated SEQ ID NOs; in some embodiments, the above percent identity value is at least 97 percent identity; in some embodiments, the above percent identity value is at least 98 percent identity; in some embodiments, the above percent identity value is at least 99 percent identity. As used herein, the percent identity values used to compare a reference sequence to a variant sequence do not include the expressly specified amino acid positions containing substitutions of the variant sequence; that is, the percent identity relationship is between sequences of a reference protein and sequences of a variant protein outside of the expressly specified positions containing substitutions in the variant. Thus, for example, if the reference sequence and the variant sequence each comprised 100 amino acids and the variant sequence had mutations at positions 25 and 81, then the percent homology would be in regard to sequences 1-24, 26-80 and 82-100.

In regard to (ii), such 3'-O-modified nucleotide may comprise a 3'-O—NH$_2$-nucleoside triphosphate, a 3'-O-azidomethyl-nucleoside triphosphate, a 3'-O-allyl-nucleoside triphosphate, a 3'O-(2-nitrobenzyl)-nucleoside triphosphate, or a 3'-O-propargyl-nucleoside triphosphate.

TABLE 1

| SEQ ID NO | Animal | Substitutions | | | | |
|---|---|---|---|---|---|---|
| 1 | Mouse | M192R/Q | C302G/R | R336L/N | R454P/N/A/V | E457N/L/T/S/K |
| 2 | Mouse | M63R/Q | C173G/R | R207L/N | R325P/N/A/V | E328N/L/T/S/K |
| 3 | Bovine | M63R/Q | C173G/R | R207L/N | R324P/N/A/V | E327N/L/T/S/K |
| 4 | Human | M63R/Q | C173G/R | R207L/N | R324P/N/A/V | E327N/L/T/S/K |
| 5 | Chicken | — | C172G/R | R206L/N | R320P/N/A/V | — |
| 6 | Possum | M63R/Q | C173G/R | R207L/N | R331P/N/A/V | E334N/L/T/S/K |
| 7 | Shrew | M63R/Q | C173G/R | R207L/N | — | E328N/L/T/S/K |
| 8 | Python | — | C174G/R | R208L/N | R331P/N/A/V | E334N/L/T/S/K |
| 9 | Canine | M73R/Q | C173G/R | R207L/N | R325P/N/A/V | E328N/L/T/S/K |
| 10 | Mole | M64R/Q | C174G/R | R208L/N | — | E329N/L/T/S/K |
| 11 | Pika | M61R/Q | C171G/R. | R205L/N | R323P/N/A/V | E326N/L/T/S/K |
| 12 | Hedgehog | M63R/Q | C173G/R | R207L/N | R328P/N/A/V | E331N/L/T/S/K |
| 13 | Tree shrew | — | C173G/R | R207L/N | R325P/N/A/V | E328N/L/T/S/K |
| 14 | Platypus | M63R/Q | C182G/R | R216L/N | R338P/N/A/V | E341N/L/T/S/K |
| 15 | Jerboa | M66R/Q | C176G/R | R210L/N | R328P/N/A/V | E331N/L/T/S/K |
| 16 | Canary | — | C17OG/R | R204L/N | R326P/N/A/V | E329N/L/T/S/K |
| 17 | Neopelma | — | C158G/R | R192L/N | R314P/N/A/V | E317N/L/T/S/K |
| 18 | Alligator | — | — | R205L/N | R327P/N/A/V | E330N/L/T/S/K |
| 19 | Xenopus | — | — | R205L/N | R324P/N/A/V | E327N/L/T/S/K |
| 20 | Tiger snake | — | — | R205L/N | R327P/N/A/V | E330N/L/T/S/K |
| 21 | Brown trout | — | — | R192L/N | R311P/N/A/V | E314N/L/T/S/K |
| 22 | Electric eel | — | — | R205L/N | R321P/N/A/V | E325N/L/T/S/K |
| 23 | Walking fish | — | — | R205L/N | R322P/N/A/V | E325N/L/T/S/K |
| 24 | Guppy | — | — | R205L/N | R322P/N/A/V | E325N/L/T/S/K |
| 25 | Rat | M48R/Q | C158G/R | R192L/N | R310P/N/A/V | E313N/L/T/S/K |
| 26 | Rat | M61R/Q | C171G/R | R205L/N | R323P/N/A/V | E326N/L/T/S/K |
| 27 | Colobus monkey | M61R/Q | C171G/R | R205L/N | R323P/N/A/V | E326N/L/T/S/K |
| 28 | Pig | M61R/Q | C171G/R | R205L/N | R323P/N/A/V | E326N/L/T/S/K |
| 29 | Tiger | M61R/Q | C171G/R | R205L/N | R323P/N/A/V | E326N/L/T/S/K |
| 30 | Water buffalo | M48R/Q | C158G/R | R192L/N | R310P/N/A/V | E313N/L/T/S/K |
| 31 | Marmot | M61R/Q | C171G/R | R205L/N | R323P/N/A/V | E326N/L/T/S/K |

In some embodiments, further TdT variants for use with methods of the invention include one or more of the substitutions of methionine, cysteine or glutamic acid, as shown in Table 1.

In some embodiments, further TdT variants for use with methods of the invention include one or more of the further substitutions of methionine, cysteine or glutamic acid, as shown in Table 1.

Further specific TdT variants that may be used in methods of the invention are set forth in Table 2. Each of the TdT variants DSI1001 through DSI1018 of Table 2 comprises an amino acid sequence at least 60 percent identical to SEQ ID NO 2 and comprises the substitutions at the indicated positions. In some embodiments, TdT variants DSI001 through DSI018 comprises an amino acid sequence at least 80 percent identical to SEQ ID NO 2 and comprises the substitutions at the indicated positions; in some embodiments, TdT variants DSI001 through DSI018 comprises an amino acid sequence at least 90 percent identical to SEQ ID NO 2 and comprises the substitutions at the indicated positions; in some embodiments, TdT variants DSI001 through DSI018 comprises an amino acid sequence at least 95 percent identical to SEQ ID NO 2 and comprises the substitutions at the indicated positions; in some embodiments, TdT variants DSI001 through DSI018 comprises an amino acid sequence at least 97 percent identical to SEQ ID NO 2 and comprises the substitutions at the indicated positions; in some embodiments, TdT variants DSI001 through DSI018 comprises an amino acid sequence at least 98 percent identical to SEQ ID NO 2 and comprises the substitutions at the indicated positions; in some embodiments, TdT variants DSI001 through DSI018 comprises an amino acid sequence at least 99 percent identical to SEQ ID NO 2 and comprises the substitutions at the indicated positions.

TABLE 2

| Specific TdT Variants for Use with Methods of the Invention | |
|---|---|
| DS1001 (TH M27) | A17V + L52F + M63R + A108V + C173G + R207L + K265T + G284P + E289V + R325P + E328N + R351K |
| DS 1002 (M44) | A17V + Q37E + D41R + L52F + G57E + M63R + S94R + G98E + A108V + S119A + L131R + S146E + Q149R + C173G + R207L + K265T + G284P + E289V + R325P + Q326F + E328N + H337D + R351K +W377R |
| DS1003 | A17V + Q37E + D41R + L52F + G57E + M63R + S94R + G98E + A108V + S146E + Q149R + C173G + F193Y + V199M + M201V + R207L + K265T + G284P + E289V + Q326F + E328N + R351K |

TABLE 2-continued

| Specific TdT Variants for Use with Methods of the Invention | |
| --- | --- |
| DS1004 (M45) | A17V + Q37E + D41R + L52F + G57E + M63R + S94R + G98E + A108V + S146E + Q149R + C173G + F193Y + V199M + M201V + R207L + K265T + G284P + E289V + R325A + Q326F + E328N + R351K |
| DS1005 | A17V + Q37E + D41R + L52F + G57E + M63R + S94R + G98E + A108V + S146E + Q149R + C173G + F193Y + V199M + M201V + R207L + K265T + G284P + E289V + Q326F + E328N + R351K |
| DS1006 (M46) | L52F + A108V + R351K + A17V + Q37E + D41R + G57E + C59R + L60D + M63R + S94R + G98E + S119A + L131R + S146E + Q149R + C173G + R207L + K265T + G284P + E289V + R325A + Q326F + E328N |
| DS1007 (M47) | L52F + A108V + R351K + A17V + Q37E + D41R + G57E + C59R + L60D + M63R + S94R + G98E + K118Q + S119A + L131R + S146E + Q149R + C173G + R207L + K265T + G284P + E289V + R325A + Q326F + E328N + W377R |
| DS1008 | A17V + Q37E + D41R + L52F + G57E + C59R + L60D + M63R + S94R + G98E + A108V + S119A + L131R + S146E + Q149R + C173G + R207L + F259S + Q261L + G284P + E289V + R325A + Q326F + E328N + R351K + W377R |
| DS1009 (MS 13-34) | A17V + D41R + L53F + G57E + C59R + L60D + M63R + S94R + G98E + K118Q + S119A + L131R + S146E + Q149R + C173G + R207L + K265T + G284P + E289V + R325A + Q326F + R351K + W377R |
| DS1010 (MS 34-1) | A17V + D41R + L52F + G57E + C59R + L60D + M63R + S94R + G98E + A108V + S119A + L131R + S146E + Q149R + R207L + K265T + G284P + E289V + R325A + Q326F + R351K |
| DS1011 | A17V + D41R + L53F + G57E + C59R + L60D + M63R + S94R + G98E + K118Q + S119A + L131R + S146E + Q149R + C173G + R207L + K265T + G284P + E289V + Q326F + R351K + W377R |
| DS1012 (M48) | A17V + Q37E + D41R + L52F + G57E + C59R + L60D + M63R + S94R + G98E + A108V + S119A + L131R + S146E + Q149R + C173G + R207L + F259S + Q261L, G284P + E289V + R325A + Q326F + E328N + R351K + W377R |
| DS1013 | A17V + Q37E + D41R + L52F + G57E + M63R + S94R + G98E + A108V + S146E + Q149R + C173G + R207L + K265T + G284P + E289V + R325A + Q326F + E328N + R351K |
| DS1014 (M49) | A17V + Q37E + D41R + L52F + G57E + C59R + L60D + M63R + S94R + G98E + A108V + S119A + L131R + S146E + Q149R + C173G + R207L + E257D + F259S + K260R + Q261L + G284P + E289V + R325A + Q326F + E328N + R351K + W377R |
| DS1015 | A17V + Q37E + D41R + L52F + G57E + C59R + L60D + M63R + S94R + G98E + A108V + S119A + L131R + S146E + Q149R + C173G + F193Y + V199M + M201V + R207L + E257D + F259S + K260R + Q261L + G284P + E289V + R325A + Q326F + E328N + R351K + W377R |
| DS1016 TH c2_5 | A17V + D41R + L52F + G57E + M63R + S94R + G98E + A108V + S146E + Q149R + C173G + M184T + R207L + K209H + G284L + E289A + R325V + E328K + R351K |
| DS1017 (M27) | A17V + L52F + G57E + M63R + A108V + C173G + R207L + K265T + G284P + E289V + R325P + E328N + R351K |
| DS1018 (M60) | A17V + L32T + Q37R + D41R + L52F + G57E + C59R + L60D + M63R + S67A + S94R + G98E + A108V + S119A +L131R + S146E + Q149R + V171A + S172E + C173R + V182I + S183E + R207L + K209H + M210K + T211I + E223G + A224P + E228D + Q261L + G284P + E289V + R325A + Q326F + E328N + R351K + D372E |

TdT variants of the invention as described above each comprise an amino acid sequence having a percent sequence identity with a specified SEQ ID NO, subject to the presence of indicated substitutions. In some embodiments, the number and type of sequence differences between a TdT variant of the invention described in this manner and the specified SEQ ID NO may be due to substitutions, deletion and/or insertions, and the amino acids substituted, deleted and/or inserted may comprise any amino acid. In some embodiments, such deletions, substitutions and/or insertions comprise only naturally occurring amino acids. In some embodiments, substitutions comprise only conservative, or synonymous, amino acid changes, as described in Grantham, Science, 185: 862-864 (1974). That is, a substitution of an amino acid can occur only among members of its set of synonymous amino acids. In some embodiments, sets of synonymous amino acids that may be employed are set forth in Table 3A.

TABLE 3A

| Synonymous Sets of Amino Acids I | |
| --- | --- |
| Amino Acid | Synonymous Set |
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Gly, Ala, Thr, Pro, Ser |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Cys, Ser, Thr |

21

TABLE 3A-continued

| Synonymous Sets of Amino Acids I | |
| --- | --- |
| Amino Acid | Synonymous Set |
| His | His, Glu, Lys, Gln, Thr, Arg |
| Gln | Gln, Glu, Lys, Asn, His, Thr, Arg |
| Asn | Asn, Gln, Asp, Ser |
| Lys | Lys, Glu, Gln, His, Arg |
| Asp | Asp, Glu, Asn |
| Glu | Glu, Asp, Lys, Asn, Gln, His, Arg |
| Met | Met, Phe, Ile, Val, Leu |
| Trp | Trp |

In some embodiments, sets of synonymous amino acids that may be employed are set forth in Table 3B.

TABLE 3B

| Synonymous Sets of Amino Acids II | |
| --- | --- |
| Amino Acid | Synonymous Set |
| Ser | Ser |
| Arg | Arg, Lys, His |
| Leu | Ile, Phe, Met, Leu |
| Pro | Ala, Pro |
| Thr | Thr |
| Ala | Pro, Ala |
| Val | Met, Ile Val |
| Gly | Gly |
| Ile | Met, Phe, Val, Leu, Ile |
| Phe | Met, Tyr, Ile, Leu, Phe |
| Tyr | Trp, Met |
| Cys | Cys, Ser |
| His | His, Gln, Arg |
| Gln | Gln, Glu, His |
| Asn | Asn, Asp |
| Lys | Lys, Arg |
| Asp | Asp, Asn |
| Glu | Glu, Gln |
| Met | Met, Phe, Ile, Val, Leu |
| Trp | Trp |

Production of TdT Variants

Variants of the invention may be produced by mutating known reference or wild type TdT-coding polynucleotides, then expressing it using conventional molecular biology techniques. For example, a desired gene or DNA fragment encoding a polypeptide of desired sequence may be assembled from synthetic fragments using conventional molecular biology techniques, e.g. using protocols described by Stemmer et al, Gene, 164: 49-53 (1995); Kodumal et al, Proc. Natl. Acad. Sci., 101: 15573-15578 (2004); or the like, or such gene or DNA fragment may be directly cloned from cells of a selected species using conventional protocols, e.g. described by Boule et al, Mol. Biotechnology, 10: 199-208 (1998), or Bentolila et al, EMBO J., 14: 4221-4229 (1995); or the like.

An isolated gene encoding a desired TdT variant may be inserted into an expression vector, such as pET32 (Novagen) to give an expression vector which then may be used to make and express variant TdT proteins using conventional protocols. Vectors with the correct sequence may be transformed in *E. coli* producer strains.

Transformed strains are cultured using conventional techniques to pellets from which TdT protein is extracted. For example, previously prepared pellets are thawed in 30 to 37° C. water bath. Once fully thawed, pellets are resuspended in lysis buffer composed of 50 mM tris-HCL (Sigma) pH 7.5, 150 mM NaCl (Sigma), 0.5 mM mercaptoethanol (Sigma), 5% glycerol (Sigma), 20 mM imidazole (Sigma) and 1 tab for 100 mL of protease cocktail inhibitor (Thermofisher). Careful resuspension is carried out in order to avoid premature lysis and remaining of aggregates. Resuspended cells are lysed through several cycles of French press, until full color homogeneity is obtained. Usual pressure used is 14,000 psi. Lysate is then centrifuged for 1 h to 1 h30 at 10,000 rpm. Centrifugate is pass through a 0.2 μm filter to remove any debris before column purification.

TdT protein may be purified from the centrifugate in a one-step affinity procedure. For example, Ni-NTA affinity column (GE Healthcare) may be used to bind the TdT polymerases. Initially the column is washed and equilibrated with 15 column volumes of 50 mM tris-HCL (Sigma) pH 7.5, 150 mM NaCl (Sigma) and 20 mM imidazole (Sigma). TdT polymerases are bound to the column after equilibration; then, a washing buffer, for example, composed of 50 mM tris-HCL (Sigma) pH 7.5, 500 mM NaCl (Sigma) and 20 mM imidazole (Sigma), may be applied to the column for 15 column volumes. After such washing, the TdT polymerases are eluted with 50 mM tris-HCL (Sigma) pH 7.5, 500 mM NaCl (Sigma) and 0.5M imidazole (Sigma). Fractions corresponding to the highest concentration of TdT polymerases of interest are collected and pooled in a single sample. The pooled fractions are dialyzed against the dialysis buffer (20 mM Tris-HCl, pH 6.8, 200 mM Na Cl, 50 mM MgOAc, 100 mM [NH4]2SO4). The dialysate is subsequently concentrated with the help of concentration filters (Amicon Ultra-30, Merk Millipore). Concentrated enzyme is distributed in small aliquots, 50% glycerol final is added, and those aliquots are then frozen at −20° C. and stored for long term. 5 μL of various fraction of the purified enzymes are analyzed in SDSPAGE gels.

In some embodiments, a TdT variant may be operably linked to a linker moiety including a covalent or non-covalent bond; amino acid tag (e.g., poly-amino acid tag, poly-His tag, 6His-tag, or the like); chemical compound (e.g., polyethylene glycol); protein-protein binding pair (e.g., biotin-avidin): affinity coupling; capture probes; or any combination of these. The linker moiety can be separate from or part of a TdT variant. An exemplary His-tag for use with TdT variants of the invention is MASSHHHHHHSSGSENLYFQTGSSG- (SEQ ID NO: 54)). The tag-linker moiety does not interfere with the nucleotide binding activity, or catalytic activity of the TdT variant.

The above processes, or equivalent processes, result in an isolated TdT variant that may be mixed with a variety of reagents, such as, salts, pH buffers, carrier compounds, and the like, that are necessary or useful for activity and/or preservation.

Template-Dependent Enzymatic Synthesis

Many polymerases and 3'-reversibly protected dNTPs are available for template-dependent enzymatic synthesis which have been developed in the DNA sequencing field, e.g. the following references (which are incorporated herein by reference) disclose exemplary polymerases and 3'-reversibly protected dNTPs: Ju et al, U.S. Pat. Nos. 6,664,079, 7,345, 159, 7,635,578, 7,713,698; Balasubramanian et al, U.S. Pat. Nos. 7,566,537, 7,790,869, 8,394,586, 9,121,062; Smith et al, U.S. Pat. No. 8,852,910; Wu, Thesis, Columbia University, 2008; Guo et al, Proc. Natl. Acad. Sci., 105(27): 9145-9150 (2008); Chen et al, U.S. Pat. Nos. 9,765,309, 10,150,954; Ost et al, U.S. Pat. No. 8,623,628; and the like. Steps of template-dependent enzymatic synthesis are similar to those for implementing template-free enzymatic synthesis, except of course, that the former employs a different type of polymerase and requires the presence of a template. Namely, after annealing a primer to a synthesized strand (serving as a template), the reverse complement of the synthesized strand is synthesized by repeated cycles of (i) reacting under extension conditions the primer or an extension intermediate having a free 3'-hydroxyl with a template-dependent polymerase in the presence of a 3'-O-protected nucleoside triphosphate to produce a 3'-O-protected extension intermediate; (ii) deprotecting the extension intermediate to produce an extension intermediate with a free 3'-hydroxyl; and (iii) repeating steps (i) and (ii) until the reverse complement is synthesized.

Base Protection Groups

A wide variety of protection groups (or equivalently, "base protecting moieties") may be employed to reduce or eliminate the formation of secondary structures in the course of polynucleotide chain extensions. Generally the conditions for removing base protection groups are orthogonal to conditions for removing 3'-O-blocking groups. In particular, where removal, or de-blocking, conditions for 3'-O-blocking groups are acidic, then base protection groups may be selected to be base labile. Under such circumstances, many base labile protection groups have been developed in phosphoramidite synthesis chemistry due to the use of acid labile 5'-O-trityl-protected monomers, e.g. Beaucage and Iyer, Tetrahedron Letters, 48(12): 2223-2311 (1992). In particular, acyl and amidine protecting groups for phosphoramidite chemistry are applicable in embodiments of the present invention (e.g. the protecting groups of Table 2 and Table 3 of Beaucage and Iyer (cited above)). In some embodiments, base protecting groups are amidines, such as described in Table 2 of Beaucage and Iyer (cited above). Generally, base-protected 3'-O-blocked nucleoside triphosphate monomers may be synthesized by routine modifications of methods described in the literature, such as described in the examples below.

In some embodiments, a base protecting group is attached to the 6-nitrogen of deoxyadenosine triphosphate, the 2-nitrogen of deoxyguanosine triphosphate, and/or the 4-nitrogen of deoxycytidine triphosphate. In some embodiments, a base protecting group is attached to all of the indicated nitrogens. In some embodiments, a base protecting group attached to a 6-nitrogen of deoxyadenosine triphosphate is selected from the group consisting of benzoyl, phthaloyl, phenoxyacetyl, and methoxyacetyl; a base protecting group attached to the 2-nitrogen of deoxyguanosine triphosphate is selected from the group consisting of isobutyryl, isobutyryloxyethylene, acetyl, 4-isopropyl-phenoxyacetyl, phenoxyacetyl, and methoxyacetyl; and a base protecting group attached to said 4-nitrogen of deoxycytidine triphosphate is selected from the group consisting of benzoyl, phthaloyl, acetyl, and isobutyryl.

In some embodiments, a protecting group attached to the 6-nitrogen of deoxyadenosine triphosphate is benzoyl; a base protecting group attached to the 2-nitrogen of deoxyguanosine triphosphate is isobutyryl or dimethylformamidine; and the base protecting group attached to the 4-nitrogen of deoxycytidine triphosphate is acetyl.

In some embodiments, a base protecting group attached to the 6-nitrogen of deoxyadenosine triphosphate is phenoxyacetyl; a base protecting group attached to the 2-nitrogen of deoxyguanosine triphosphate is 4-isopropyl-phenoxyacetyl or dimethylformamidine; and the base protecting group attached to the 4-nitrogen of deoxycytidine triphosphate is acetyl.

In some embodiments, base protecting moieties are removed (i.e. the product is deprotected) and product is cleaved from a solid support in the same reaction. For example, an initiator may comprise a ribo-uridine which may be cleaved to release the polynucleotide product by treatment with 1 M KOH, or like reagent (ammonia, ammonium hydroxide, NaOH, or the like), which simultaneously removes base-labile base protecting moieties.

Further Modifications of Elongation Conditions

In addition to providing 3'-O-blocked dNTP monomers with base protection groups, elongation reactions may be performed at higher temperatures using thermal stable template-free polymerases. For example, a thermal stable template-free polymerase having activity above 40° C. may be employed; or, in some embodiments, a thermal stable template-free polymerase having activity in the range of from 40-85° C. may be employed; or, in some embodiments, a thermal stable template-free polymerase having activity in the range of from 40-65° C. may be employed.

In some embodiments, elongation conditions may include adding solvents to an elongation reaction mixture that inhibit hydrogen bonding or base stacking. Such solvents include water miscible solvents with low dielectric constants, such as dimethyl sulfoxide (DMSO), methanol, and the like. Likewise, in some embodiments, elongation conditions may include the provision of chaotropic agents that include, but are not limited to, n-butanol, ethanol, guanidinium chloride, lithium perchlorate, lithium acetate, magnesium chloride, phenol, 2-propanol, sodium dodecyl sulfate, thiourea, urea, and the like. In some embodiments, elongation conditions include the presence of a secondary-structure-suppressing amount of DMSO. In some embodiments, elongation conditions may include the provision of DNA binding proteins that inhibit the formation of secondary structures, wherein such proteins include, but are not limited to, single-stranded binding proteins, helicases, DNA glycolases, and the like.

Parallel Polynucleotide Synthesis on Solid Supports Using Template-Free Polymerases In some embodiments, parallel synthesis is implemented by providing a support having discrete, non-overlapping, addressable sites where separate polynucleotides are synthesized and a means for controlling electrochemical conditions at each site independently of the other sites is provided. In some embodiments, such parallel synthesis support is a planar support having a regular pattern of addressable sites, such as, a rectilinear pattern of sites, or a hexagonal pattern of sites. In some embodiments, each site of a planar support is associated with one or more electrodes whose electrical characteristics may be controlled in an addressable manor independent of other electrodes of the planar support. In some embodiments, such planar supports have a plurality of sites comprising at least 256 sites, at least 512 sites, at least 1024 sites, at least 5000 sites, at least 10,000 sites, at least 25,000 sites, or at least 100,000 sites and as many as 10,000,000 sites. In some embodiments, such planar supports have a plurality of sites greater than 1000, or 10,000, or 25,000, or 50,000, or 100,000, or 500,000, and up to 1,000,000 sites or up to 10,000,000 sites. In some embodiments, the sites of such planar supports are disposed in a regular array and each site is associated with at least one electrode integrated with the planar support. In some embodiments, the discrete site at which synthesis and/or sequencing take place each has an area in the range of from 0.25 $\mu m^2$ to 1000 $\mu m^2$, or from 1 $\mu m^2$ to 1000 $\mu m^2$, or from 10 $\mu m^2$ to 1000 $\mu m^2$, or from 100 $\mu m^2$ to 1000 $\mu m^2$. In some embodiments, the amount of polynucleotides synthesized at each site is at least $10^{-6}$ fmol, or at least $10^{-3}$ fmol, or at least 1 fmol, or at least 1 µmol, or the amount of polynucleotide synthesized at each site is in the range of from $10^{-6}$ fmol to 1 fmol, or from $10^{-3}$ fmol to 1 fmol, or from 1 fmol to 1 µmol, or from $10^{-6}$ µmol to 10 µmol, or from $10^{-6}$ µmol to 1 µmol. In some embodiments, the number of polynucleotides synthesized at each site is in the range of from 1000 molecules to $10^6$ molecules, or from 1000 molecules to $10^9$ molecules, or from 1000 molecules to $10^{12}$ molecules. Addressable sites on the above arrays may be arranged into groups comprising zones, such as zone 1 and zone 2, as described above, to implement methods of the invention.

In some embodiments, enzymatically synthesized polynucleotides at each reaction site have lengths in the range of from 50 to 500 nucleotides; in other embodiments, such polynucleotides have lengths in the range of from 50 to 1000 nucleotides.

Figure 1B:
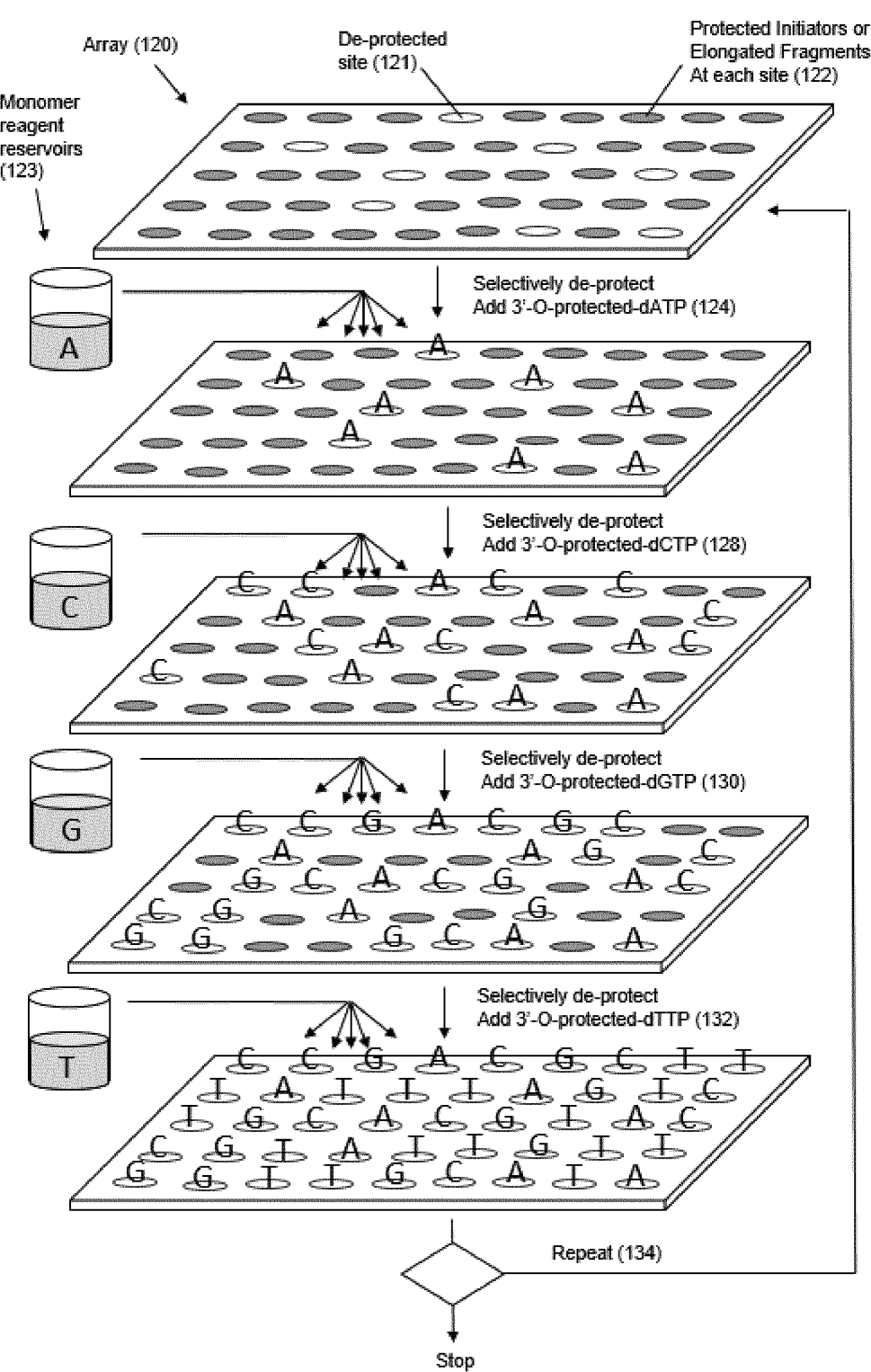

FIG. 1B illustrates the steps for one embodiment of parallel synthesis of a plurality of polynucleotides on discrete sites addressable either for specific photo-illumination or for electrode activation. In some embodiments, the array is an addressable electrode array in which individual electrodes may be controlled to generate a predetermined voltage difference between any given working electrode of the array and a counter electrode. Array (120) is provided such that each site (122) has an initiator or an elongated fragment with a protected 3'-hydroxyl (represented as the dark disks). To initiate a synthesis cycle, the 3'-hydroxyls of initiators or elongated fragments of selected sites (the ones corresponding to polynucleotides for which the next monomer is A) are deprotected (121) (represented as open disks) using a deprotection method that can be restricted to the location of the selected sites. As described more fully below, in some embodiments, such localized deprotection may be effected by localized photoreactions or by localized changes in voltage differences using site-specific electrodes. To the selectively deprotected sites is added a reagent comprising 3'-O-protected-dATPs (124) and a template-free polymerase, such as a TdT, is delivered to the deprotected sites. As described briefly below, the synthesis reagents may be delivered in a variety of ways, such as, by simple bulk flow over the entire array, droplets delivered by an inkjet device to individual sites, or the like. After a predetermined time for the coupling reaction to advance to completion or to a suitable extent, the array is washed and the next group of polynucleotides (those for which C is the next monomer) at selected sites have their 3'-hydroxyls deprotected. To the selectively deprotected sites is added a reagent comprising 3'-O-protected-dCTPs (128) and a template-free polymerase, such as a TdT, is delivered to the deprotected sites. Similar steps are performed for dGTPs (130) and dTTPs (132), until the cycle is completed. The cycles are repeated (134) until the polynucleotides are completed.

Photo-Induced Deprotection.

In some embodiments, parallel synthesis may employ photo induced deprotection with a photogenerated acid to locally deprotect, e.g. Gao et al, U.S. Pat. Nos. 6,426,184, 7,491,680 and 7,838,466. Advantageously, the oligonucleotides are synthesized in a flow cell, very similar to those used for Sequencing by Synthesis (SBS) today. SBS uses modified dNTPs containing a terminator which blocks further polymerization. So only a single base can be added by a polymerase enzyme to each growing DNA or RNA copy strand. The sequencing reaction is conducted simultaneously on a very large number of different template molecules spread out on a solid surface. Following the addition of the four dNTPs to the templates, the terminators are removed.

This chemistry is called "reversible terminators". Finally, another four cycles of dNTP additions are initiated. Since single bases are added to all templates in a uniform fashion, the sequencing process produces a set of DNA/RNA sequence reads of uniform length. Advantageously, the DNA/RNA sample is prepared into a "sequencing library" by the fragmentation into pieces each around 200 bases long. Custom adapters are added to each end and the library is flowed across a solid surface (the "flow cell") and the template fragments bind to this surface. Following this, a solid phase "bridge amplification" PCR process (cluster generation) creates approximately one million copies of each template in tight physical clusters on the flowcell surface.

Electrochemical Deprotection.

Figure 7A:
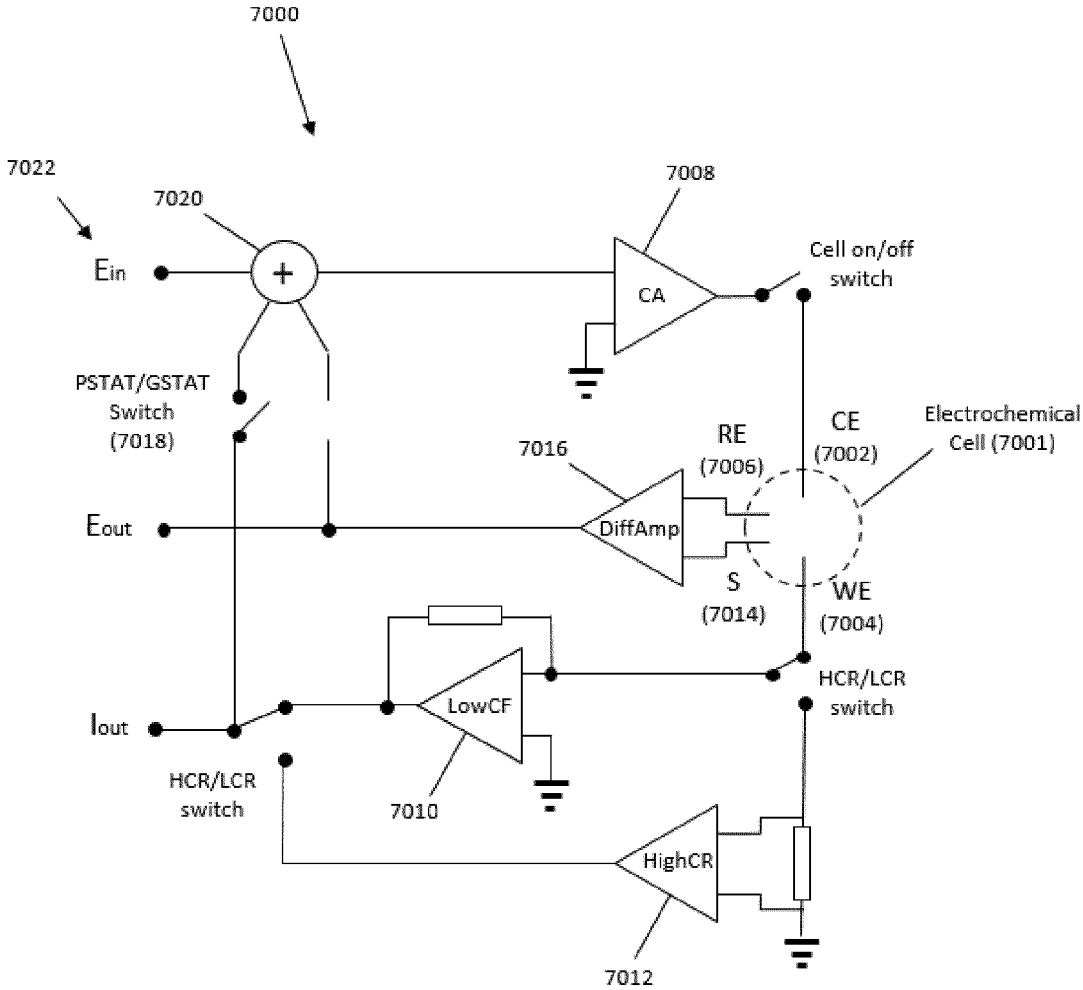
FIG. 7A illustrates a potentiostat/galvanostat (PGSTAT) circuit that can be used can be used to directly or indirectly cleave electrochemically labile groups.

Alternatively or in addition to local photochemical generation of pH changes, controlled changes in electrical potential at an electrode can be used to directly or indirectly cleave electrochemically labile groups. For example, pH-sensitive protection groups may be indirectly cleaved using voltage changes by employing an electroactive compound whose redox state may be changed by controlling local voltage differences, thereby liberating electrons which affect local pH, e.g. Southern, U.S. Pat. No. 5,667,667; Egeland and Southern, U.S. patent publication US2004/0238369; Egeland et al, Nucleic Acids Research, 33(14): e125 (2005); Maurer et al, U.S. Pat. No. 9,267,213; Fomina et al, LabChip, 16: 2236-2244 (2016), As illustrated in FIG. 7A, in some embodiments, each site on an electrode array may be configured as a potentiostat and/or galvanostat electrochemical cell (7001) as described by Levine et al (cited above) or Metrohm application note EC08. In potentiostatic mode, a potentiostat/galvanostat (PGSTAT) circuit (7000) as illustrated in FIG. 7A will accurately control the potential of Counter Electrode (CE) (7002) against the Working Electrode (WE) (7004) so that the potential difference between the working electrode (WE) (7004) and the Reference Electrode (RE) (7006) is well defined, and correspond to the value specified by the user. In galvanostatic mode, the current flow between the WE (7004) and the CE (7002) is controlled. The potential difference between the RE (7006) and WE (7004) and the current flowing between the CE (7002) and WE (7004) are continuously monitored. By using a PGSTAT, the value specified by the user (i.e. applied potential or current) is accurately controlled, anytime during the measurement by using a negative feedback mechanism.

As can be seen from the diagram, the CE (7002) is connected to the output of an electronic block referred to as a Control Amplifier (CA) (7008). The control amplifier forces current to flow through the cell. The value of the current is measured using a Current Follower (LowCF) (7010) or a Shunt (HighCR) (7012), for low and high currents, respectively. The potential difference is measured always between the RE (7006) and S (7014) with a Differential Amplifier (Diffamp) (7016). Depending on the mode the instrument is used (potentiostatic or galvanostatic) the PSTAT/GSTAT switch (7018) is set accordingly. The signal is then fed into the Summation Point (+) (7020) which, together with the waveform set by a digital-to-analog converter (Ein) (7022) will be used as an input for the control amplifier.

A counter electrode (also known as auxiliary electrode), is an electrode which is used to close the current circuit in the electrochemical cell. It is usually made of an inert material (e.g. Pt, Au, graphite, glassy carbon) and usually it does not participate in the electrochemical reaction. Because the current is flowing between the WE (7004) and the CE (7002), the total surface area of the CE (source/sink of electrons) is typically larger than the area of the WE so that it will not be a limiting factor in the kinetics of the electrochemical process.

A reference electrode is an electrode which has a stable and well-known electrode potential and it is used as a point of reference in the electrochemical cell for the potential control and measurement. The high stability of the reference electrode potential is usually reached by employing a redox system with constant (buffered or saturated) concentrations of each participants of the redox reaction. Moreover, the current flow through the reference electrode is kept close to zero (ideally, zero) which is achieved by using the CE to close the current circuit in the cell together with a very high input impedance on the electrometer (>100 GOhm).

The working electrode is the electrode in an electrochemical system on which the reaction of interest is occurring. Common working electrodes can be made of inert materials such as Au, Ag, Pt, glassy carbon (GC) and Hg drop and film electrodes etc. Working electrode (7004) may comprise a coating for attaching molecules, such as initiators for template-free enzymatic polynucleotide synthesis.

Two electrode setup. In a two-electrode cell setup, CE (7002) and RE (7006) are shorted on one of the electrodes while the WE (7004) and S (7014) are shorted on the opposite electrode. The potential across the complete cell is measured. This includes contributions from the CE/electrolyte interface and the electrolyte itself. The two-electrode configuration can therefore be used whenever precise control of the interfacial potential across the WE (7004) electrochemical interface is not critical and the behavior of the whole cell is under investigation.

Three electrode setup. The three-electrode cell setup is the most common electrochemical cell setup used in electrochemistry. In this case, the current flows between the CE (7002) and the WE (7004). The potential difference is controlled between the WE (7004) and the CE (7002) and measured between the RE (7006) (preferably kept at close proximity of the WE (7004)) and S (7014). Because the WE (7004) is connected with S (7014) and WE (7004) is kept at pseudo-ground (fixed, stable potential), by controlling the polarization of the CE (7002), the potential difference between RE (7006) and WE (7004) is controlled all the time. The potential between the WE (7004) and CE (7002) usually is not measured. This is the voltage applied by the control amplifier (7008) and it is limited by the compliance voltage of the instrument. It is adjusted so that the potential difference between the WE (7004) and RE (7006) will be equal to the potential difference specified by the user. This configuration allows the potential across the electrochemical interface at the WE (7004) to be controlled with respect to the RE (7006).

Large-scale electrode arrays comprising a plurality of individually addressable electrodes formed in a circuit-supporting substrate, especially CMOS, have been constructed for phosphoramidite-based synthesis and for sensor applications, e.g. Montgomery, U.S. Pat. Nos. 6,093,302, 6,444,111 and 6,280,595; Gindilis, U.S. Pat. No. 9,339,782; Maurer et al, U.S. Pat. No. 9,267,213; Maurer et al, PLoSOne, December 2006, issue 1, e34; Fomina et al, LabChip, 16: 2236-2244 (2016); Kavusi et al, U.S. Pat. No. 9,075,041; Johnson et al, U.S. Pat. Nos. 9,874,538 and 9,910,008; Gordon et al, U.S. Pat. No. 6,251,595; Levine et al, and the like. IEEE J. Solid State Circuits, 43: 1859-1871 (2008); and the like. These references provide guidance for the design of particular embodiments of the present invention with respect to such features as electrode numbers, size, composition and configurations at array sites; CMOS circuitry for voltage and current control and measurement; array fabrication and operation; methodologies for attaching or immobilizing chemical components (such as, for example, initiators) at array sites; and the like.

Of particular interest are the electrode configurations described in Morimoto et al, Anal. Chem. 80: 905-914 (2008); Levine et al (cited above); and Fomina et al (cited above) and their implementation with CMOS technology, particularly as described by Levine et al and Fomina et al. In some embodiments of the invention, an electrode array is provided comprising a plurality of individually addressable working electrodes in a CMOS substrate, which is operationally associated with a reference electrode and a counter electrode, the latter of which may be onboard or separate from the CMOS electrode array. CMOS circuitry is configured so that the voltage between the working electrodes and the counter electrode (s) may be adjusted to establish and maintain a desired voltage difference between selected working electrodes and the reference electrode. The desired voltage differences may be changed at selected working electrodes to cleave electrochemically labile protecting groups.

Combination of Enzymatic Synthesis and Electrochemical Deprotection.

In one aspect, the present invention also provides a solution for combining the different ways to induced specially controlled deprotection, through pH decrease, with enzymatic DNA synthesis technology. Enzymatic synthesis is fully compatible with aqueous media. Most of the chemistry, electrochemistry or photochemistry, enabling a pH change though physical actuation are working only in aqueous media. The invention is providing technical solution to make these two aspects compatible by developing the appropriate chemistry for pH change and the appropriate buffers, reagents and protection groups for the enzymatic synthesis. So, in one of the embodiment the controllable chemistry is compatible with DNA synthesis and with the flow-cell chip surface chemistry.

Electrochemical, or Induced, deprotection, that is, the use of voltage changes at an electrode adjacent to a reaction site, has been employed to remove DMT protection groups in phosphoramidite-based synthesis, e.g. Egeland et al, Nucleic Acids Research, 33(14): e125 (2005); Montgomery (cited above). The invention in part is a discovery and recognition that parallel template-free enzymatic polynucleotide synthesis could be accomplished using electrochemical deprotection of protecting groups specific for enzymatic synthesis. In particular, 3'-O-azidomethyl protecting groups may be cleaved by direct reduction and 3'-O-amino protecting groups may be cleaved indirectly by adjusting local pH by way of an electroactive intermediary compound. For example, in the case of the latter, in some embodiments, a typical deprotection solution is 700 mM sodium nitrite (NaNO2) and 1 M sodium acetate titrated to pH 5.0-5.5 with HCl. Local deprotection of 3'-O—NH2 groups at a reaction site of an array may be effected by lowering the local pH from pH 7 to pH 5.

Apparatus for implementing methods of the invention. Components of an apparatus for implementing a method of the invention are illustrated diagrammatically in FIG. 7B. Flow cell and electrode array (700) comprise an array of reaction sites each of which may include a microwell, coatings to enhance attachment of initiators or other components and each of which is operationally associated with one or more electrodes. In some embodiments, the electrode array is integrated with CMOS control and measurement circuitry as a single chip. A flow cell can have a variety of designs for controlling the path and flow rate of reagents over the electrode array. In some embodiments, a flow cell is a microfluidics device. That is, it may be fabricated with micromachining techniques or precision molding to include additional fluidic passages, chambers, and so on. In one aspect, a flow cell comprises an inlet (702), an outlet (703), and a flow chamber (705) for defining the flow path of reagents over electrode array (707). Reagents are discarded into a waste container (706) after exiting flow cell and sensor array (700). In accordance with this embodiment, a function of the apparatus is to deliver different reagents to flow cell and electrode array (700) in a predetermined sequence, for predetermined durations, at predetermined flow rates, and optionally to measure physical and/or chemical parameters at the electrode sites that provide information about the status of a reaction taking place therein. To this end, fluidics controller (718) controls by lines (720 and 722) the driving forces for a plurality of reagents (714) (for example, 3'-O-protected dNTPs and/or template-free polymerase in appropriate buffers and deprotection solution(s)) and the operation of valves (for example, 712 and 716) by conventional instrument control software, e.g. Lab View (National Instruments, Austin, Tex.).

The reagents may be driven through the fluid pathways, valves and flow cell by pumps, by gas pressure, or other conventional methods. In some embodiments, a single reference electrode (708) may be positioned upstream of flow cell and sensor array (700). In other embodiments, a reference electrode may be positioned within the flow chamber. In some embodiments, a single fluid or reagent is in contact with reference electrode (708) throughout an entire multi-step reaction. This may be achieved with the configuration illustrated in FIG. 7B where reagents (714) are directed through passage (709) to flow cell (705). When those reagents are flowing, valve (712) is shut, thereby preventing any wash solution from flowing into passage (709). Although the flow of wash solution is stopped, there is still uninterrupted fluid and electrical communication between reference electrode, passage (709), and electrode array (707). At most reagents (714) when flowing through passage (709) diffuse into passage (711), but the distance between reference electrode (708) and the junction between passages (709) and (711) is selected so that little or no amount of the reagents flowing in common passage (709) reach reference electrode (708). Although FIG. 7B and other figures illustrate an electrode (for example, reference electrode, 708) as a cylinder concentric with a fluid passage (for example, 711), reference electrodes, such as (708), may have a variety of different shapes. For example, it could be a wire inserted into the lumen of (711). In one aspect, reference electrode (708) constitutes a section of passage (712) that is made of a conductive material, such as stainless steel, gold, or the like. In some embodiments, the material is inert with respect to reagents in contact with it. Reference electrode (708) in one embodiment is a tube made of a conductive material which forms part of passage (712).

Figure 7B:
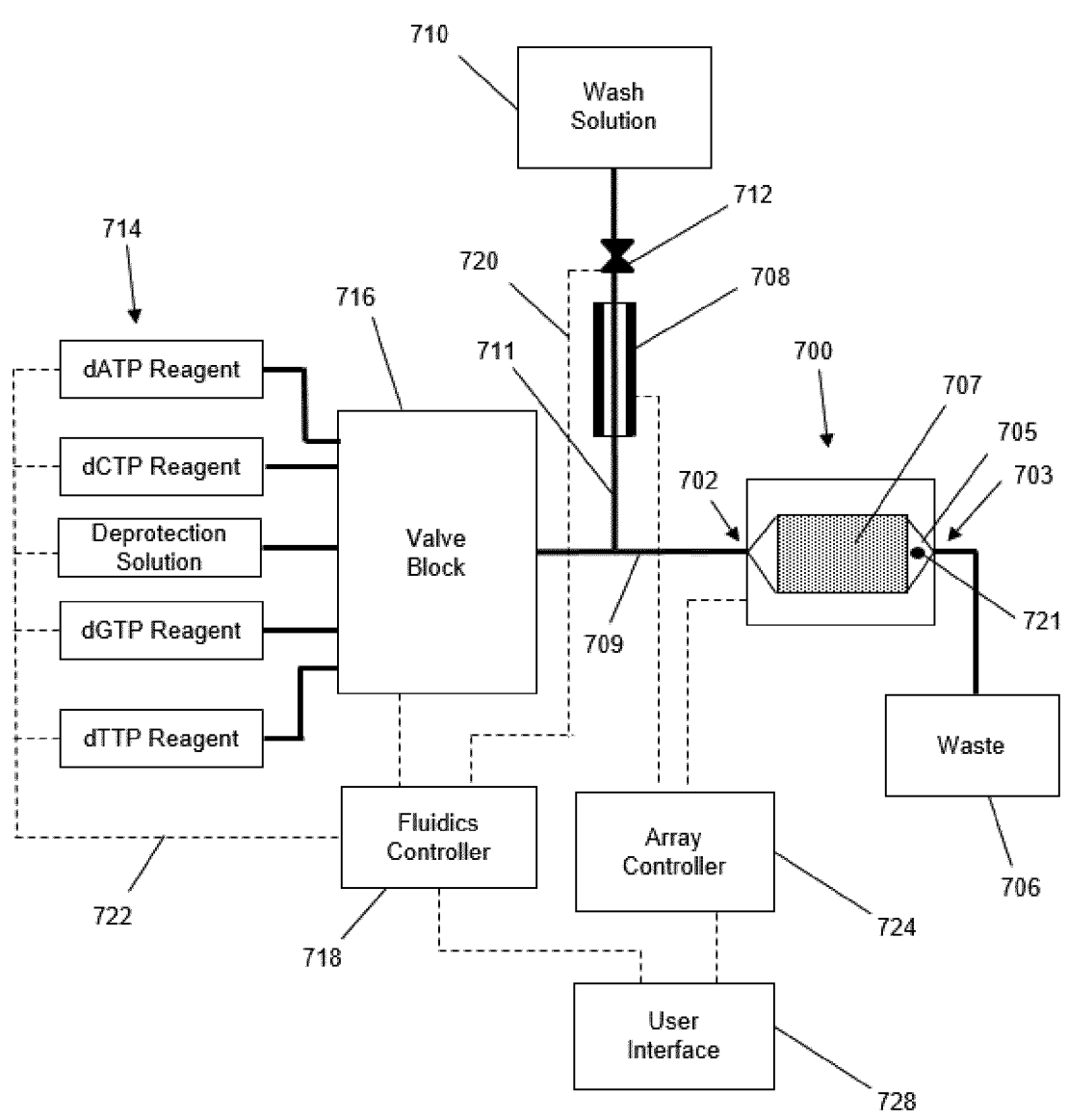
FIG. 7B diagrammatically illustrates components of an apparatus for implementing a method of the invention.

The potential of the reference voltage depends on the interface between the electrode and the solution in which the electrode is in contact. For example, solutions of different nucleoside triphosphates may cause the reference voltage to change, thereby causing undesirable changes at the working electrodes. For multi-step reactions using frequent wash steps, wash solution (710) may be selected as the reagent in continuous contact with reference electrode (708) as illustrated in FIG. 7B.

Further components of this embodiment include array controller (724) for providing bias voltages (such as to control the potential between working electrodes and counter electrodes (721), which may or may not be integral with array (707)) and timing and control signals to the electrode array (if such components are not integrated into the electrode array), and for collecting and/or processing output signals. Information from flow cell and electrode array (700), as well as instrument settings and controls may be displayed and entered through user interface (728). For some embodiments, for example, nucleic acid synthesis and/or sequencing, the temperature of flow cell and sensor array (700) is controlled so that reactions take place and measurements are made at a known, and preferably, predetermined temperatures. Such temperature may be controlled by conventional temperature control devices, such as, a Peltier device, or the like. In one aspect, temperature is conveniently controlled by controlling the temperatures of the reagents flowing through the flow cell. Flow cells and fluidic circuits of the apparatus may be fabricated by a variety of methods and materials. Factors to be considered in selecting materials include degree of chemical inertness required, operating conditions, e.g. temperature, and the like, volume of reagents to be delivered, whether or not a reference voltage is required, manufacturability, and the like. For small scale fluid deliveries, microfluidic fabrication techniques are well-suited for making fluidics circuits of the invention, and guidance for such techniques is readily available to one of ordinary skill in the art, e.g. Malloy, Plastic Part Design for Injection Molding: An Introduction (Hanser Gardner Publications, 1994); Herold et al, Editors, Lab-on-a-Chip Technology (Vol. 1): Fabrication and Microfluidics (Caister Academic Press, 2009); and the like. For meso-scale and larger scale fluid deliveries, conventional machining techniques may be used to fabricate parts that may be assembled into flow cells or fluidic circuits of the invention. In one aspect, plastics such as polycarbonate, polymethyl methacrylate, and the like, may be used to fabricate flow cells and fluidics circuits of the invention.

Figure 7C:
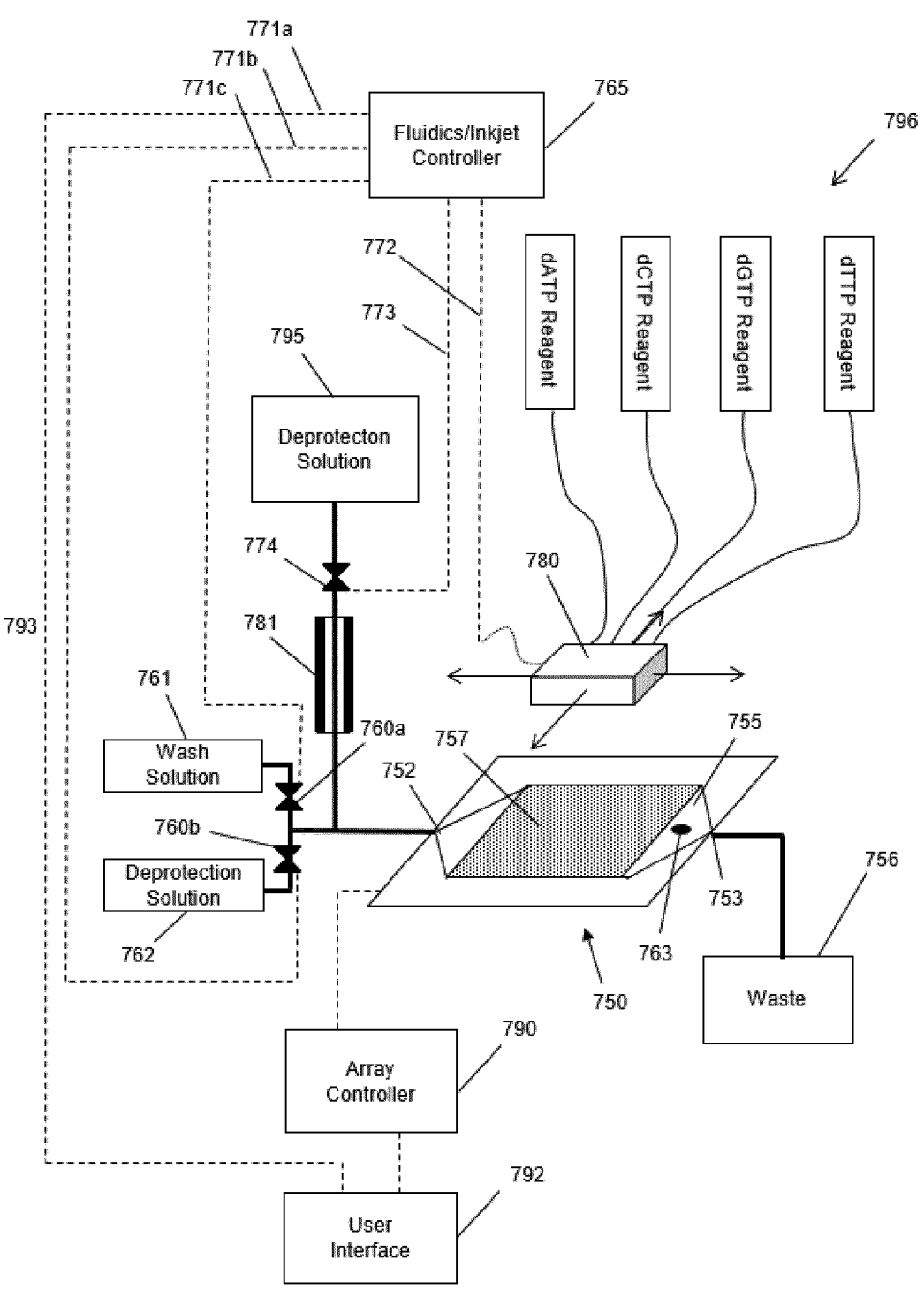
FIG. 7C illustrates diagrammatically an alternative apparatus for implementing methods of the invention wherein some reagents are delivered to reaction sites using an inkjet droplet generator.

FIG. 7C illustrates diagrammatically an alternative apparatus for implementing methods of the invention wherein some reagents are delivered to reaction sites using an inkjet droplet generator. Many of the design features described above are applicable to this embodiment. As above, flow cell and electrode array (750) comprise an array of reaction sites each of which may include a microwell, coatings to enhance attachment of initiators or other components and each of which is operationally associated with one or more electrodes. As above, in some embodiments, the electrode array may be integrated with CMOS control and measurement circuitry as a single chip. A flow cell can have a variety of designs for controlling the path and flow rate of reagents over the electrode array; however, unlike the apparatus of FIG. 7B, here reaction sites of the electrode array must be accessible for delivery of reagent-containing droplets by print head (780). In one aspect, a flow cell comprises an inlet (752), an outlet (753), and a flow chamber (755) for defining the flow path of reagents (not delivered by print head (780)) over electrode array (757). Reagents are discarded into a waste container (756) after exiting flow cell and sensor array (750). In accordance with this embodiment, a function of the apparatus is to deliver different reagents either via inlet (752) or print head (780) to flow cell and electrode array (750) in a predetermined sequence, for predetermined durations, at predetermined flow rates, and optionally to measure physical and/or chemical parameters at the electrode or reaction sites that provide information about the status of a reaction taking place therein. To this end, fluidics controller (758) controls by lines (771*a*, 7711*b* and 771*c*) valves (760*a* and 760*b*) and print head (780). Valves (760*a*) and (760*b*) control the delivery of wash solution (761) and deprotection solution (762) (if required) to flow cell (757). Guidance for design and control of inkjet delivery systems is well known by those with skill in the art and may be found in U.S. patent publication US2003/0170698 and U.S. Pat. Nos. 6,306,599; 6,323,043; 7,276,336; 7,534,561; and like references.

In some embodiments, a single reference electrode (708) may be positioned upstream of flow cell and sensor array (700). In other embodiments, a reference electrode may be positioned within the flow chamber. In some embodiments, a single counter electrode (763) may be employed, or in other embodiments, more than one counter electrodes may be employed, and as described, above such counter electrodes may or may not be integrated on the same electronic substrate as the working electrodes of array (757).

The apparatus is controlled through user interface (792) which, in turn, actuates and monitors synthesis steps through fluidics/inkjet controller (765) and array controller (790) as indicated by dashed lines (771, 772 and 773). In particular, physical parameters, such as temperature, and circuitry for electrode selection, voltage control, sensor readouts, and the like, are handled by array controller (790); selection of reagents (796), droplet rates, head movement, and the like, is controlled by fluidics/inkjet controller (765). In some embodiments, during droplet delivery of 3'-O-protected dNTP monomers and/or template-free polymerase, the electrolyte connect between reaction sites and reference electrode (781) is broken as flow cell (755) may be drained to prevent cross contamination between adjacent reaction sites that receive different monomers. In some embodiments, such cross contamination may be avoided by providing reaction sites surrounded by hydrophobic regions so that each site is encompassed by an isolated liquid droplet when an electrolyte, such as, a wash solution or a deprotection solution, recedes from the flow chamber, e.g. as described in Brennan, U.S. Pat. Nos. 5,474,796, 6,921,636, and the like. In particular, when the flow chamber is flooded with deprotection solution a continuous electrolyte path is restored to reference electrode (781) and counter electrode(s) which may be either on array (757) or off-array.

In some implementations, the value of the voltage difference between working electrodes and reference electrode is selected to avoid unwanted redox reactions, such as electrolysis of water, so that bubbles do not form in the fluidics of the device. In some embodiments, predetermined voltage differences to bring about electrochemical reactions in the invention are about 1.5 volts or less.

In some embodiments, methods of the invention, such as implemented by the apparatus of FIGS. 7B and 7C, may comprise the steps of (a) providing a spatially addressable array of reaction sites, wherein each reaction site is operationally associated with at least one working electrode and has disposed thereon initiators attached by their 5'-ends and having a 3'-O-electrochemically labile protecting group; (b) performing for each kind of nucleotide a cycle comprising steps of (i) deprotecting initiators or elongated fragments at electrodes at predetermined addresses by generating a voltage difference between each of the electrodes at the predetermined addresses and a reference electrode so that the electrochemically labile protecting group is cleaved, thereby generating free 3'-hydroxyls on the initiators or elongated fragments at the electrodes of the predetermined addresses, and (ii) contacting under elongation conditions the electrodes at the predetermined addresses with a 3'-O-electrochemically labile-protected nucleoside triphosphate and a template-independent DNA polymerase so that the initiators or elongated fragments at the predetermined addresses are elongated by the incorporation of a 3'-electrochemically labile-protected nucleoside triphosphate to form 3'-O-electrochemically labile-protected elongated fragments; and (c) repeating step (b) until the array of polynucleotides of predetermined sequences is completed. Reaction sites are generally discrete regions on a substrate within which a single kind of polynucleotide with a predetermined sequence is synthesized. Reaction sites are spatially addressable in the sense that they have well defined locations on a substrate or surface, which usually form a regular pattern, such as a rectilinear pattern, hexagonal pattern, or the like. Each reaction site is operationally associated with at least one working electrode in the sense that the electrical potential, or voltage, at the reaction site may be controlled or determined by its associated one or more working electrodes. Typically reaction sites and working electrodes are spatially aligned. That is, if an electrode is a disc or other planar structure embedded on a substrate surface, the area occupied by a reaction site corresponds to the area of the electrode surface. This is advantageous for ensuring a uniform electrical effect in reactions taking place at the reaction site. In some embodiments, a reaction site may comprise a substrate or film on a surface of a working electrode, for example, such substrate or film may be used to facilitate attachment and/or retention of components, such as, initiators. Such substrates and electrodes may be integrated in a semiconductor device, such as a CMOS device. In reference to step (b), performing the indicated cycle of steps for each kind of nucleotide is not intended to be limited to the four nucleotides A, C, G and T. In some embodiments, each kind of nucleotide means a subset of A, C, G and T. In other embodiments, each kind of nucleotide means an extended set that may include non-natural nucleotides or other nucleotide analogs that may be useful for encoding information in polynucleotides. A variety of template-independent DNA polymerases may be employed in methods of the invention; in particular, variants of terminal deoxynucleotidyl transferase are employed, e.g. as described in Ybert et al, International patent publication WO/2019/030149, or the like. The cycles of step (b) may include further steps, such as washing steps. Elongation conditions comprise buffers, salts, temperature, co-factors and the like, that are necessary or useful for incorporation activity of the template-free polymerase employed.

In some embodiments, an electrochemically labile protecting group may be pH sensitive and pH may be regulated by voltage difference between working electrodes and a reference electrode which voltage activates an electroactive agent which, in turn, changes the pH, e.g. Southern, U.S. Pat. No. 5,667,667; Mauer et al, U.S. Pat. No. 9,267,213; and the like, which are hereby incorporated by reference. Exemplary, electroactive agents include hydroquinone, benzoquinone, quinone, and derivatives thereof.

In some embodiments, electrochemically labile protecting groups may themselves be redox sensitive such that a voltage difference between a working electrode and a reference electrode converts the electrochemically labile protecting group into a reduced state thereby cleaving said electrochemically labile protecting group. In particular, in some embodiments, a redox sensitive 3'-O-protection group is azidomethyl.

Kits for Practicing Methods of the Invention

The invention includes a variety of kits for practicing methods of the invention. In one aspect, kits of the invention comprise a TdT variant in a formulation suitable for carrying out template-free enzymatic polynucleotide synthesis as described herein. Such kits may also include synthesis buffers that provide reaction conditions for optimizing the template-free addition or incorporation of a 3'-O-protected dNTP to a growing strand. In some embodiments, kits of the invention further include 3'-O-reversibly protected dNTPs. In such embodiments, the 3'-O-reversibly protected dNTPs may comprise 3'-O-amino-dNTPs or 3'-O-azidomethyl-dNTPs. In further embodiments, kits may include one or more of the following items, either separately or together with the above-mentioned items: (i) deprotection reagents for carrying out a deprotecting step as described herein, (ii) solid supports with initiators attached thereto, (iii) cleavage reagents for releasing completed polynucleotides from solid supports, (iv) wash reagents or buffers for removing unre-acted 3'-O-protected dNTPs at the end of an enzymatic addition or coupling step, (v) post-synthesis processing reagents, such as purification columns, desalting reagents, eluting reagents, and the like, (vi) primers for annealing to a common primer binding site synthesized on the 3'-ends of full length polynucleotide products, (vii) a template-dependent polymerase for extending primers annealed to a primer binding site of polynucleotide products, (viii) one or more single-stranded nucleases to digest fragments melted from polynucleotide products and/or failure sequences.

In regard to items (ii) and (iii) above, certain initiators and cleavage reagents go together. For example, an initiator comprising an inosine cleavable nucleotide may come with an endonuclease V cleavage reagent; an initiator comprising a nitrobenzyl photocleavable linker may come with a suit-able light source for cleaving the photocleavable linker; an initiator comprising a uracil may come with a uracil DNA glycosylase cleavage reagent; and the like.

Definitions

Unless otherwise specifically defined herein, terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999).

071 "Functionally equivalent" in reference to amino acid positions in two or more different TdTs means (i) the amino acids at the respective positions play the same functional role in an activity of the TdTs, and (ii) the amino acids occur at homologous amino acid positions in the amino acid sequences of the respective TdTs. It is possible to identify positionally equivalent or homologous amino acid residues in the amino acid sequences of two or more different TdTs on the basis of sequence alignment and/or molecular mod-elling. In some embodiments, functionally equivalent amino acid positions belong to inefficiency motifs that are con-served among the amino acid sequences of TdTs of evolu-tionarily related species, e.g. genus, families, or the like. Examples of such conserved inefficiency motifs are described in Motea et al, Biochim. Biophys. Acta. 1804(5): 1151-1166 (2010); Delarue et al, EMBO J., 21: 427-439 (2002); and like references.

"Kit" refers to any delivery system, such as a package, for delivering materials or reagents for carrying out a method implemented by a system or apparatus of the invention. In some embodiments, consumables materials or reagents are delivered to a user of a system or apparatus of the invention in a package referred to herein as a "kit." In the context of systems and apparatus of the invention, such delivery sys-tems include, usually packaging methods and materials that allow for the storage, transport, or delivery of materials, such as, synthesis plates that may have easily damaged or contaminated components, such as synthesis supports. For example, kits may include one or more enclosures (e.g., boxes) containing the synthesis plates and/or supporting materials. Such contents may be delivered to the intended recipient together or separately. For example, a first con-tainer may contain a synthesis plate with synthesis supports in each well vacuum wrapped in a protective plastic mate-rial, while a second or more containers contain 3'-O-revers-ibly blocked dNTPs and template-free polymerase and buf-fer.

"Mutant" or "variant," which are used interchangeably, refer to polypeptides derived from a natural or reference TdT polypeptide described herein, and comprising a modification or an alteration, i.e., a substitution, insertion, and/or dele-tion, at one or more positions. Variants may be obtained by various techniques well known in the art. In particular, examples of techniques for altering the DNA sequence encoding the wild-type protein, include, but are not limited to, site-directed mutagenesis, random mutagenesis, sequence shuffling and synthetic oligonucleotide construc-tion. Mutagenesis activities consist in deleting, inserting or substituting one or several amino-acids in the sequence of a protein or in the case of the invention of a polymerase. The following terminology is used to designate a substitution: L238A denotes that amino acid residue (Leucine, L) at position 238 of a reference, or wild type, sequence is changed to an Alanine (A). A132V/I/M denotes that amino acid residue (Alanine, A) at position 132 of the parent sequence is substituted by one of the following amino acids: Valine (V), Isoleucine (I), or Methionine (M). The substi-tution can be a conservative or non-conservative substitu-tion. Examples of conservative substitutions are within the groups of basic amino acids (arginine, lysine and histidine), acidic amino acids (glutamic acid and aspartic acid), polar amino acids (glutamine, asparagine and threonine), hydro-phobic amino acids (methionine, leucine, isoleucine, cyste-ine and valine), aromatic amino acids (phenylalanine, tryp-tophan and tyrosine), and small amino acids (glycine, alanine and serine).

"Polynucleotide" or "oligonucleotide" are used inter-changeably and each mean a linear polymer of nucleotide monomers or analogs thereof. Monomers making up poly-nucleotides and oligonucleotides are capable of specifically binding to a natural polynucleotide by way of a regular pattern of monomer-to-monomer interactions, such as Wat-son-Crick type of base pairing, base stacking, Hoogsteen or reverse Hoogsteen types of base pairing, or the like. Such monomers and their internucleosidic linkages may be natu-rally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucle-otide or polynucleotide requires enzymatic processing, such as extension by a polymerase, ligation by a ligase, or the like, one of ordinary skill would understand that oligonucle-otides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5-3' order from left to right and that "A" denotes deoxy-adenosine, "C" denotes deoxycytidine, "G" denotes deox-yguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually poly-nucleotides comprise the four natural nucleosides (e.g. deoxyadenosine, deoxycytidine, deoxyguanosine, deoxy-thymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate require-ments for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references. Likewise, the oligonucleotide and polynucleotide may refer to either a single stranded form or a double stranded form (i.e. duplexes of an oligonucleotide or polynucleotide and its respective complement). It will be clear to one of ordinary skill which form or whether both forms are intended from the context of the terms usage.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Prim-ers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, 2nd Edition (Cold Spring Harbor Press, New York, 2003).

"Sequence identity" refers to the number (or fraction, usually expressed as a percentage) of matches (e.g., identical amino acid residues) between two sequences, such as two polypeptide sequences or two polynucleotide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global align-ment algorithm (e.g. Needleman and Wunsch algorithm; Needleman and Wunsch, J. Mol. Biol., 48: 443-453 (1970))

which aligns the sequences optimally over the entire length, while sequences of substantially different lengths are pref-erably aligned using a local alignment algorithm (e.g. Smith and Waterman algorithm (Smith and Waterman, J. Mol. Biol., 147: 195-197 (1981)) or Altschul algorithm (Altschul et al., Nucleic Acids Research, 25(17): 3389-3402 (1997); Altschul et al., FEBS J., 272: 5101-5109 (2005)). Alignment for purposes of determining percent amino acid sequence identity can be achieved in various ways that are within the skill in the art, for instance, using publicly available com-puter software available on internet web sites such as http://blast.ncbi.nlm.nih.gov/or http://www.ebi.ac.uk/Tools/ emboss/. Those skilled in the art can determine appropriate parameters for measuring alignment, including any algo-rithm needed to achieve maximal alignment over the full length of the sequences being compared. For purposes herein, % amino acid sequence identity values refer to values generated using the pair wise sequence alignment program EMBOSS Needle, that creates an optimal global alignment of two sequences using the Needleman-Wunsch algorithm, wherein all search parameters are set to default values, i.e. Scoring matrix=BLOSUM62, Gap open=10, Gap extend=0.5, End gap penalty=false, End gap open=10 and End gap extend=0.5.

"Substitution" means that an amino acid residue is replaced by another amino acid residue. Preferably, the term "substitution" refers to the replacement of an amino acid residue by another selected from the naturally-occurring standard 20 amino acid residues, rare naturally occurring amino acid residues (e.g. hydroxyproline, hydroxylysine, allohydroxylysine, 6-N-methylysine, N-ethylglycine, N-methylglycine, N-ethylasparagine, allo-isoleucine, N-methylisoleucine, N-methylvaline, pyroglutamine, ami-nobutyric acid, ornithine, norleucine, norvaline), and non-naturally occurring amino acid residue, often made syntheti-cally, (e.g. cyclohexyl-alanine). Preferably, the term "substitution" refers to the replacement of an amino acid residue by another selected from the naturally-occurring standard 20 amino acid residues. The sign "+" indicates a combination of substitutions. The amino acids are herein represented by their one-letter or three-letters code accord-ing to the following nomenclature: A: alanine (Ala); C: cysteine (Cys); D: aspartic acid (Asp); E: glutamic acid (Glu); F: phenylalanine (Phe); G: glycine (Gly); H: histidine (His); I: isoleucine (Ile); K: lysine (Lys); L: leucine (Leu); M: methionine (Met): N: asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr). In the present document, the following ter-minology is used to designate a substitution: L238A denotes that amino acid residue (Leucine, L) at position 238 of the parent sequence is changed to an Alanine (A). A132V/I/M denotes that amino acid residue (Alanine, A) at position 132 of the parent sequence is substituted by one of the following amino acids: Valine (V), Isoleucine (I), or Methionine (M). The substitution can be a conservative or non-conservative substitution. Examples of conservative substitutions are within the groups of basic amino acids (arginine, lysine and histidine), acidic amino acids (glutamic acid and aspartic acid), polar amino acids (glutamine, asparagine and threo-nine), hydrophobic amino acids (methionine, leucine, iso-leucine, cysteine and valine), aromatic amino acids (phe-nylalanine, tryptophan and tyrosine), and small amino acids (glycine, alanine and serine).

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

The invention claimed is:

1. A method of synthesizing a polynucleotide having a predetermined sequence, the method comprising:
   (a) providing an initiator attached by a 5' end to a solid support and having a 3'-terminal nucleotide with a free 3'-hydroxyl;
   (b) repeating cycles of
      (i) contacting under elongation conditions the initiator or elongated fragments having free 3'-O-hydroxyls with a 3'-O-blocked nucleoside triphosphate and a template-independent DNA polymerase so that the initiator or elongated fragments are elongated by incorporation of a 3'-O-blocked nucleoside triphosphate to form 3'-O-blocked elongated fragments, and
      (ii) deblocking the 3'-O-blocked elongated fragments to form elongated fragments having free 3'-hydroxyls, until polynucleotides having the predetermined sequences are formed;
   (c) generating double stranded polynucleotides by annealing primers to the 3'-ends of the polynucleotides formed in (b) and extending the primers with a template-dependent polymerase to create reverse complements of the polynucleotides;
   (d) providing reaction conditions with a hybridization stringency that dissociate failure sequences among the double stranded polynucleotides; and (e) digesting strands of the dissociated double stranded polynucleotides.

2. The method of claim 1, wherein the primers are annealed to a common primer binding site of the polynucleotides in (c), and wherein the method further comprises cleaving said common primer binding site from undigested double stranded augmented polynucleotides to produce said polynucleotides of the predetermined sequence.

3. The method of claim 1, wherein said template-independent DNA polymerase is a terminal deoxynucleotidyl-transferase (TdT) variant having an amino acid sequence at least 90 percent identical to an amino acid sequence selected from SEQ ID NO: 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31, wherein such selected amino acid sequence is subject to two or more mutations listed in Table 1 for its SEQ ID NO; and wherein the TdT variant
   (i) is capable of synthesizing a nucleic acid fragment without a template and
   (ii) is capable of incorporating a 3'-O-blocked nucleotide onto a free 3'-hydroxyl of a polynucleotide.

4. The method of claim 1, wherein said 3'-O-blocked nucleotide comprises a 3'-O-blocking group selected from the group consisting of 3'-O-methyl, 3'-O-(2-nitrobenzyl), 3'-O-allyl, 3'-O-amine, 3'-O-azidomethyl, 3'-O-tert-butoxy ethoxy, 3'-O-(2-cyanoethyl), 3'-O-nitro, and 3'-O-propargyl.

5. The method of claim 1, wherein said initiator comprises a cleavable nucleotide or a cleavable linkage at its 3'-end and wherein said polynucleotides having said predetermined sequences are released from said solid support by cleaving the cleavable nucleotide or the cleavable linkage.

6. The method of claim 1, wherein said digesting comprises digesting the strands of the dissociated double-stranded augmented polynucleotides with an exonuclease or a nonspecific single-stranded endonuclease.

7. The method of claim 1, wherein reagents for synthesizing the polynucleotide are delivered to reaction sites on the solid support using an inkjet droplet generator or by bulk flow over the solid support.

8. The method of claim 7, wherein the reaction sites are organized in a spatially addressable array on the solid support.

9. The method of claim 8, wherein each of said reaction sites are distinct and non-overlapping with other said reaction sites.

10. The method of claim 9, wherein a different polynucleotide is synthesized at each reaction site.

11. The method of claim 1, wherein (b) further comprises capping said initiators or elongated fragments that fail to be elongated.

\* \* \* \* \*

```
                        SEQUENCE LISTING

<160> NUMBER OF SEQ ID NOS: 31

<210> SEQ ID NO 1
<211> LENGTH: 510
<212> TYPE: PRT
<213> ORGANISM: ARTIFICIAL SEQUENCE
<220> FEATURE:
<223> OTHER INFORMATION: TdT full length mouse

<400> SEQUENCE: 1

Met Asp Pro Leu Gln Ala Val His Leu Gly Pro Arg Lys Lys Arg Pro
1               5                   10                  15

Arg Gln Leu Gly Thr Pro Val Ala Ser Thr Pro Tyr Asp Ile Arg Phe
            20                  25                  30

Arg Asp Leu Val Leu Phe Ile Leu Glu Lys Lys Met Gly Thr Thr Arg
        35                  40                  45

Arg Ala Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Leu Gln Asn Ile Lys Ala Ser
            85                  90                  95

Ser Glu Leu Glu Leu Leu Asp Ile Ser Trp Leu Ile Glu Cys Met Gly
            100                 105                 110

Ala Gly Lys Pro Val Glu Met Met Gly Arg His Gln Leu Val Val Asn
            115                 120                 125

Arg Asn Ser Ser Pro Ser Pro Val Pro Gly Ser Gln Asn Val Pro Ala
        130                 135                 140

Pro Ala Val Lys Lys Ile Ser Gln Tyr Ala Cys Gln Arg Arg Thr Thr
145                 150                 155                 160

Leu Asn Asn Tyr Asn Gln Leu Phe Thr Asp Ala Leu Asp Ile Leu Ala
                165                 170                 175

Glu Asn Asp Glu Leu Arg Glu Asn Glu Gly Ser Cys Leu Ala Phe Met
            180                 185                 190

Arg Ala Ser Ser Val Leu Lys Ser Leu Pro Phe Pro Ile Thr Ser Met
            195                 200                 205

Lys Asp Thr Glu Gly Ile Pro Cys Leu Gly Asp Lys Val Lys Ser Ile
    210                 215                 220

Ile Glu Gly Ile Ile Glu Asp Gly Glu Ser Ser Glu Ala Lys Ala Val
225                 230                 235                 240

Leu Asn Asp Glu Arg Tyr Lys Ser Phe Lys Leu Phe Thr Ser Val Phe
                245                 250                 255

Gly Val Gly Leu Lys Thr Ala Glu Lys Trp Phe Arg Met Gly Phe Arg
            260                 265                 270

Thr Leu Ser Lys Ile Gln Ser Asp Lys Ser Leu Arg Phe Thr Gln Met
            275                 280                 285

Gln Lys Ala Gly Phe Leu Tyr Tyr Glu Asp Leu Val Ser Cys Val Asn
    290                 295                 300

Arg Pro Glu Ala Glu Ala Val Ser Met Leu Val Lys Glu Ala Val Val
305                 310                 315                 320
```

-continued

```
Thr Phe Leu Pro Asp Ala Leu Val Thr Met Thr Gly Gly Phe Arg Arg
            325                 330                 335

Gly Lys Met Thr Gly His Asp Val Asp Phe Leu Ile Thr Ser Pro Glu
            340                 345                 350

Ala Thr Glu Asp Glu Glu Gln Gln Leu Leu His Lys Val Thr Asp Phe
            355                 360                 365

Trp Lys Gln Gln Gly Leu Leu Leu Tyr Cys Asp Ile Leu Glu Ser Thr
    370                 375                 380

Phe Glu Lys Phe Lys Gln Pro Ser Arg Lys Val Asp Ala Leu Asp His
385                 390                 395                 400

Phe Gln Lys Cys Phe Leu Ile Leu Lys Leu Asp His Gly Arg Val His
            405                 410                 415

Ser Glu Lys Ser Gly Gln Gln Glu Gly Lys Gly Trp Lys Ala Ile Arg
            420                 425                 430

Val Asp Leu Val Met Cys Pro Tyr Asp Arg Arg Ala Phe Ala Leu Leu
            435                 440                 445

Gly Trp Thr Gly Ser Arg Gln Phe Glu Arg Asp Leu Arg Arg Tyr Ala
    450                 455                 460

Thr His Glu Arg Lys Met Met Leu Asp Asn His Ala Leu Tyr Asp Arg
465                 470                 475                 480

Thr Lys Arg Val Phe Leu Glu Ala Glu Ser Glu Glu Glu Ile Phe Ala
            485                 490                 495

His Leu Gly Leu Asp Tyr Ile Glu Pro Trp Glu Arg Asn Ala
            500                 505                 510
```

```
<210> SEQ ID NO 2
<211> LENGTH: 381
<212> TYPE: PRT
<213> ORGANISM: ARTIFICIAL SEQUENCE
<220> FEATURE:
<223> OTHER INFORMATION: TdT truncated mouse sequence

<400> SEQUENCE: 2
```

```
Asn Ser Ser Pro Ser Pro Val Pro Gly Ser Gln Asn Val Pro Ala Pro
1               5                   10                  15

Ala Val Lys Lys Ile Ser Gln Tyr Ala Cys Gln Arg Arg Thr Thr Leu
            20                  25                  30

Asn Asn Tyr Asn Gln Leu Phe Thr Asp Ala Leu Asp Ile Leu Ala Glu
            35                  40                  45

Asn Asp Glu Leu Arg Glu Asn Glu Gly Ser Cys Leu Ala Phe Met Arg
    50                  55                  60

Ala Ser Ser Val Leu Lys Ser Leu Pro Phe Pro Ile Thr Ser Met Lys
65                  70                  75                  80

Asp Thr Glu Gly Ile Pro Cys Leu Gly Asp Lys Val Lys Ser Ile Ile
            85                  90                  95

Glu Gly Ile Ile Glu Asp Gly Glu Ser Ser Glu Ala Lys Ala Val Leu
            100                 105                 110

Asn Asp Glu Arg Tyr Lys Ser Phe Lys Leu Phe Thr Ser Val Phe Gly
            115                 120                 125

Val Gly Leu Lys Thr Ala Glu Lys Trp Phe Arg Met Gly Phe Arg Thr
    130                 135                 140

Leu Ser Lys Ile Gln Ser Asp Lys Ser Leu Arg Phe Thr Gln Met Gln
145                 150                 155                 160

Lys Ala Gly Phe Leu Tyr Tyr Glu Asp Leu Val Ser Cys Val Asn Arg
            165                 170                 175
```

-continued

```
Pro Glu Ala Glu Ala Val Ser Met Leu Val Lys Glu Ala Val Val Thr
            180                 185                 190

Phe Leu Pro Asp Ala Leu Val Thr Met Thr Gly Gly Phe Arg Arg Gly
            195             200                 205

Lys Met Thr Gly His Asp Val Asp Phe Leu Ile Thr Ser Pro Glu Ala
            210             215                 220

Thr Glu Asp Glu Glu Gln Gln Leu Leu His Lys Val Thr Asp Phe Trp
225                 230                 235                 240

Lys Gln Gln Gly Leu Leu Leu Tyr Cys Asp Ile Leu Glu Ser Thr Phe
                245                 250                 255

Glu Lys Phe Lys Gln Pro Ser Arg Lys Val Asp Ala Leu Asp His Phe
            260                 265                 270

Gln Lys Cys Phe Leu Ile Leu Lys Leu Asp His Gly Arg Val His Ser
            275                 280                 285

Glu Lys Ser Gly Gln Gln Glu Gly Lys Gly Trp Lys Ala Ile Arg Val
            290                 295                 300

Asp Leu Val Met Cys Pro Tyr Asp Arg Arg Ala Phe Ala Leu Leu Gly
305                 310                 315                 320

Trp Thr Gly Ser Arg Gln Phe Glu Arg Asp Leu Arg Arg Tyr Ala Thr
                325                 330                 335

His Glu Arg Lys Met Met Leu Asp Asn His Ala Leu Tyr Asp Arg Thr
            340                 345                 350

Lys Arg Val Phe Leu Glu Ala Glu Ser Glu Glu Glu Ile Phe Ala His
            355                 360                 365

Leu Gly Leu Asp Tyr Ile Glu Pro Trp Glu Arg Asn Ala
    370                 375                 380

<210> SEQ ID NO 3
<211> LENGTH: 380
<212> TYPE: PRT
<213> ORGANISM: ARTIFICIAL SEQUENCE
<220> FEATURE:
<223> OTHER INFORMATION: Bovine truncated (catalytic domain):

<400> SEQUENCE: 3

Asp Tyr Ser Ala Thr Pro Asn Pro Gly Phe Gln Lys Thr Pro Pro Leu
1               5                   10                  15

Ala Val Lys Lys Ile Ser Gln Tyr Ala Cys Gln Arg Lys Thr Thr Leu
            20                  25                  30

Asn Asn Tyr Asn His Ile Phe Thr Asp Ala Phe Glu Ile Leu Ala Glu
            35                  40                  45

Asn Ser Glu Phe Lys Glu Asn Glu Val Ser Tyr Val Thr Phe Met Arg
            50                  55                  60

Ala Ala Ser Val Leu Lys Ser Leu Pro Phe Thr Ile Ile Ser Met Lys
65                  70                  75                  80

Asp Thr Glu Gly Ile Pro Cys Leu Gly Asp Lys Val Lys Cys Ile Ile
                85                  90                  95

Glu Glu Ile Ile Glu Asp Gly Glu Ser Ser Glu Val Lys Ala Val Leu
            100                 105                 110

Asn Asp Glu Arg Tyr Gln Ser Phe Lys Leu Phe Thr Ser Val Phe Gly
            115                 120                 125

Val Gly Leu Lys Thr Ser Glu Lys Trp Phe Arg Met Gly Phe Arg Ser
    130                 135                 140

Leu Ser Lys Ile Met Ser Asp Lys Thr Leu Lys Phe Thr Lys Met Gln
145                 150                 155                 160
```

```
Lys Ala Gly Phe Leu Tyr Tyr Glu Asp Leu Val Ser Cys Val Thr Arg
            165                 170                 175

Ala Glu Ala Glu Ala Val Gly Val Leu Val Lys Glu Ala Val Trp Ala
            180                 185                 190

Phe Leu Pro Asp Ala Phe Val Thr Met Thr Gly Gly Phe Arg Arg Gly
            195                 200                 205

Lys Lys Ile Gly His Asp Val Asp Phe Leu Ile Thr Ser Pro Gly Ser
    210                 215                 220

Ala Glu Asp Glu Glu Gln Leu Leu Pro Lys Val Ile Asn Leu Trp Glu
225                 230                 235                 240

Lys Lys Gly Leu Leu Leu Tyr Tyr Asp Leu Val Glu Ser Thr Phe Glu
            245                 250                 255

Lys Phe Lys Leu Pro Ser Arg Gln Val Asp Thr Leu Asp His Phe Gln
            260                 265                 270

Lys Cys Phe Leu Ile Leu Lys Leu His His Gln Arg Val Asp Ser Ser
            275                 280                 285

Lys Ser Asn Gln Gln Glu Gly Lys Thr Trp Lys Ala Ile Arg Val Asp
    290                 295                 300

Leu Val Met Cys Pro Tyr Glu Asn Arg Ala Phe Ala Leu Leu Gly Trp
305                 310                 315                 320

Thr Gly Ser Arg Gln Phe Glu Arg Asp Ile Arg Arg Tyr Ala Thr His
            325                 330                 335

Glu Arg Lys Met Met Leu Asp Asn His Ala Leu Tyr Asp Lys Thr Lys
            340                 345                 350

Arg Val Phe Leu Lys Ala Glu Ser Glu Glu Glu Ile Phe Ala His Leu
            355                 360                 365

Gly Leu Asp Tyr Ile Glu Pro Trp Glu Arg Asn Ala
    370                 375                 380
```

```
<210> SEQ ID NO 4
<211> LENGTH: 380
<212> TYPE: PRT
<213> ORGANISM: ARTIFICIAL SEQUENCE
<220> FEATURE:
<223> OTHER INFORMATION: TdT Human truncated

<400> SEQUENCE: 4
```

```
Asp Tyr Ser Asp Ser Thr Asn Pro Gly Pro Pro Lys Thr Pro Pro Ile
1               5                   10                  15

Ala Val Gln Lys Ile Ser Gln Tyr Ala Cys Gln Arg Arg Thr Thr Leu
            20                  25                  30

Asn Asn Cys Asn Gln Ile Phe Thr Asp Ala Phe Asp Ile Leu Ala Glu
            35                  40                  45

Asn Cys Glu Phe Arg Glu Asn Glu Asp Ser Cys Val Thr Phe Met Arg
    50                  55                  60

Ala Ala Ser Val Leu Lys Ser Leu Pro Phe Thr Ile Ile Ser Met Lys
65                  70                  75                  80

Asp Thr Glu Gly Ile Pro Cys Leu Gly Ser Lys Val Lys Gly Ile Ile
            85                  90                  95

Glu Glu Ile Ile Glu Asp Gly Glu Ser Ser Glu Val Lys Ala Val Leu
            100                 105                 110

Asn Asp Glu Arg Tyr Gln Ser Phe Lys Leu Phe Thr Ser Val Phe Gly
            115                 120                 125

Val Gly Leu Lys Thr Ser Glu Lys Trp Phe Arg Met Gly Phe Arg Thr
    130                 135                 140
```

-continued

```
Leu Ser Lys Val Arg Ser Asp Lys Ser Leu Lys Phe Thr Arg Met Gln
145             150             155             160

Lys Ala Gly Phe Leu Tyr Tyr Glu Asp Leu Val Ser Cys Val Thr Arg
            165             170             175

Ala Glu Ala Glu Ala Val Ser Val Leu Val Lys Glu Ala Val Trp Ala
            180             185             190

Phe Leu Pro Asp Ala Phe Val Thr Met Thr Gly Gly Phe Arg Arg Gly
            195             200             205

Lys Lys Met Gly His Asp Val Asp Phe Leu Ile Thr Ser Pro Gly Ser
        210             215             220

Thr Glu Asp Glu Glu Gln Leu Leu Gln Lys Val Met Asn Leu Trp Glu
225             230             235             240

Lys Lys Gly Leu Leu Leu Tyr Tyr Asp Leu Val Glu Ser Thr Phe Glu
            245             250             255

Lys Leu Arg Leu Pro Ser Arg Lys Val Asp Ala Leu Asp His Phe Gln
            260             265             270

Lys Cys Phe Leu Ile Phe Lys Leu Pro Arg Gln Arg Val Asp Ser Asp
            275             280             285

Gln Ser Ser Trp Gln Glu Gly Lys Thr Trp Lys Ala Ile Arg Val Asp
        290             295             300

Leu Val Leu Cys Pro Tyr Glu Arg Arg Ala Phe Ala Leu Leu Gly Trp
305             310             315             320

Thr Gly Ser Arg Gln Phe Glu Arg Asp Leu Arg Arg Tyr Ala Thr His
            325             330             335

Glu Arg Lys Met Ile Leu Asp Asn His Ala Leu Tyr Asp Lys Thr Lys
            340             345             350

Arg Ile Phe Leu Lys Ala Glu Ser Glu Glu Glu Ile Phe Ala His Leu
            355             360             365

Gly Leu Asp Tyr Ile Glu Pro Trp Glu Arg Asn Ala
    370             375             380
```

```
<210> SEQ ID NO 5
<211> LENGTH: 376
<212> TYPE: PRT
<213> ORGANISM: ARTIFICIAL SEQUENCE
<220> FEATURE:
<223> OTHER INFORMATION: TdT Chicken 1 truncated

<400> SEQUENCE: 5

Gln Tyr Pro Thr Leu Lys Thr Pro Glu Ser Glu Val Ser Ser Phe Thr
1               5               10              15

Ala Ser Lys Val Ser Gln Tyr Ser Cys Gln Arg Lys Thr Thr Leu Asn
            20              25              30

Asn Cys Asn Lys Lys Phe Thr Asp Ala Phe Glu Ile Met Ala Glu Asn
        35              40              45

Tyr Glu Phe Lys Glu Asn Glu Ile Phe Cys Leu Glu Phe Leu Arg Ala
    50              55              60

Ala Ser Val Leu Lys Ser Leu Pro Phe Pro Val Thr Arg Met Lys Asp
65              70              75              80

Ile Gln Gly Leu Pro Cys Met Gly Asp Arg Val Arg Asp Val Ile Glu
            85              90              95

Glu Ile Ile Glu Glu Gly Glu Ser Ser Arg Ala Lys Asp Val Leu Asn
            100             105             110

Asp Glu Arg Tyr Lys Ser Phe Lys Glu Phe Thr Ser Val Phe Gly Val
        115             120             125
```

-continued

```
Gly Val Lys Thr Ser Glu Lys Trp Phe Arg Met Gly Leu Arg Thr Val
    130             135             140

Glu Glu Val Lys Ala Asp Lys Thr Leu Lys Leu Ser Lys Met Gln Arg
145             150             155             160

Ala Gly Phe Leu Tyr Tyr Glu Asp Leu Val Ser Cys Val Ser Lys Ala
                165             170             175

Glu Ala Asp Ala Val Ser Ser Ile Val Lys Asn Thr Val Cys Thr Phe
                180             185             190

Leu Pro Asp Ala Leu Val Thr Ile Thr Gly Gly Phe Arg Arg Gly Lys
            195             200             205

Lys Ile Gly His Asp Ile Asp Phe Leu Ile Thr Ser Pro Gly Gln Arg
    210             215             220

Glu Asp Asp Glu Leu Leu His Lys Gly Leu Leu Leu Tyr Cys Asp Ile
225             230             235             240

Ile Glu Ser Thr Phe Val Lys Glu Gln Ile Pro Ser Arg His Val Asp
                245             250             255

Ala Met Asp His Phe Gln Lys Cys Phe Ala Ile Leu Lys Leu Tyr Gln
            260             265             270

Pro Arg Val Asp Asn Ser Ser Tyr Asn Met Ser Lys Lys Cys Asp Met
    275             280             285

Ala Glu Val Lys Asp Trp Lys Ala Ile Arg Val Asp Leu Val Ile Thr
    290             295             300

Pro Phe Glu Gln Tyr Ala Tyr Ala Leu Leu Gly Trp Thr Gly Ser Arg
305             310             315             320

Gln Phe Gly Arg Asp Leu Arg Arg Tyr Ala Thr His Glu Arg Lys Met
            325             330             335

Met Leu Asp Asn His Ala Leu Tyr Asp Lys Arg Lys Arg Val Phe Leu
            340             345             350

Lys Ala Gly Ser Glu Glu Glu Ile Phe Ala His Leu Gly Leu Asp Tyr
        355             360             365

Val Glu Pro Trp Glu Arg Asn Ala
    370             375
```

```
<210> SEQ ID NO 6
<211> LENGTH: 387
<212> TYPE: PRT
<213> ORGANISM: ARTIFICIAL SEQUENCE
<220> FEATURE:
<223> OTHER INFORMATION: Possum truncated

<400> SEQUENCE: 6
```

```
Ser Ala Asn Pro Asp Pro Thr Ala Gly Thr Leu Asn Ile Leu Pro Pro
1               5               10              15

Thr Thr Lys Thr Ile Ser Gln Tyr Ala Cys Gln Arg Arg Thr Thr Ile
            20              25              30

Asn Asn His Asn Gln Arg Phe Thr Asp Ala Phe Glu Ile Leu Ala Lys
        35              40              45

Asn Tyr Glu Phe Lys Glu Asn Asp Asp Thr Cys Leu Thr Phe Met Arg
    50              55              60

Ala Ile Ser Val Leu Lys Cys Leu Pro Phe Glu Val Val Ser Leu Lys
65              70              75              80

Asp Thr Glu Gly Leu Pro Trp Ile Gly Asp Glu Val Lys Gly Ile Met
                85              90              95

Glu Glu Ile Ile Glu Asp Gly Glu Ser Leu Glu Val Gln Ala Val Leu
            100             105             110
```

```
Asn Asp Glu Arg Tyr Gln Ser Phe Lys Leu Phe Thr Ser Val Phe Gly
        115                 120                 125

Val Gly Leu Lys Thr Ala Asp Lys Trp Tyr Arg Met Gly Phe Arg Thr
        130                 135                 140

Leu Asn Lys Ile Arg Ser Asp Lys Thr Leu Lys Leu Thr Lys Met Gln
145                 150                 155                 160

Lys Ala Gly Leu Cys Tyr Tyr Glu Asp Leu Ile Asp Cys Val Ser Lys
                165                 170                 175

Ala Glu Ala Asp Ala Val Ser Leu Leu Val Gln Asp Ala Val Trp Thr
            180                 185                 190

Phe Leu Pro Asp Ala Leu Val Thr Ile Thr Gly Gly Phe Arg Arg Gly
            195                 200                 205

Lys Glu Phe Gly His Asp Val Asp Phe Leu Ile Thr Ser Pro Gly Ala
        210                 215                 220

Glu Lys Glu Gln Glu Asp Gln Leu Leu Gln Lys Val Thr Asn Leu Trp
225                 230                 235                 240

Lys Lys Gln Gly Leu Leu Leu Tyr Cys Asp Leu Ile Glu Ser Thr Phe
                245                 250                 255

Glu Asp Leu Lys Leu Pro Ser Arg Lys Ile Asp Ala Leu Asp His Phe
            260                 265                 270

Gln Lys Cys Phe Leu Ile Leu Lys Leu Tyr His His Lys Glu Asp Lys
        275                 280                 285

Arg Lys Trp Glu Met Pro Thr Gly Ser Asn Glu Ser Glu Ala Lys Ser
        290                 295                 300

Trp Lys Ala Ile Arg Val Asp Leu Val Val Cys Pro Tyr Asp Arg Tyr
305                 310                 315                 320

Ala Phe Ala Leu Leu Gly Trp Ser Gly Ser Arg Gln Phe Glu Arg Asp
                325                 330                 335

Leu Arg Arg Tyr Ala Thr His Glu Lys Lys Met Met Leu Asp Asn His
            340                 345                 350

Ala Leu Tyr Asp Lys Thr Lys Lys Ile Phe Leu Lys Ala Lys Ser Glu
            355                 360                 365

Glu Glu Ile Phe Ala His Leu Gly Leu Glu Tyr Ile Gln Pro Ser Glu
        370                 375                 380

Arg Asn Ala
385
```

```
<210> SEQ ID NO 7
<211> LENGTH: 381
<212> TYPE: PRT
<213> ORGANISM: ARTIFICIAL SEQUENCE
<220> FEATURE:
<223> OTHER INFORMATION: truncated shrew

<400> SEQUENCE: 7
```

```
Asp Cys Pro Ala Ser His Asp Ser Ser Pro Gln Lys Thr Glu Ser Ala
1                 5                   10                  15

Ala Val Gln Lys Ile Ser Gln Tyr Ala Cys Gln Arg Arg Thr Thr Leu
                20                  25                  30

Asn Asn His Asn His Ile Phe Thr Asp Ala Phe Glu Ile Leu Ala Glu
            35                  40                  45

Asn Cys Glu Phe Arg Glu Asn Glu Gly Ser Tyr Val Thr Tyr Met Arg
        50                  55                  60

Ala Ala Ser Val Leu Lys Ser Leu Pro Phe Ser Ile Ile Ser Met Lys
65                  70                  75                  80
```

```
Asp Thr Glu Gly Ile Pro Cys Leu Ala Asp Lys Val Lys Cys Val Ile
                85              90                  95

Glu Glu Ile Ile Glu Asp Gly Glu Ser Ser Glu Val Lys Ala Val Leu
                100             105                 110

Asn Asp Glu Arg Tyr Lys Ser Phe Lys Leu Phe Thr Ser Val Phe Gly
            115             120             125

Val Gly Leu Lys Thr Ala Glu Lys Trp Phe Arg Leu Gly Phe Arg Thr
    130             135             140

Leu Ser Gly Ile Met Asn Asp Lys Thr Leu Lys Leu Thr His Met Gln
145             150             155                 160

Lys Ala Gly Phe Leu Tyr Tyr Glu Asp Leu Val Ser Cys Val Thr Arg
            165             170             175

Ala Glu Ala Glu Ala Val Gly Val Leu Val Lys Glu Ala Val Trp Ala
            180             185             190

Phe Leu Pro Asp Ala Ile Val Thr Met Thr Gly Gly Phe Arg Arg Gly
            195             200             205

Lys Lys Val Gly His Asp Val Asp Phe Leu Ile Thr Ser Pro Glu Ala
    210             215             220

Thr Glu Glu Gln Glu Gln Gln Leu Leu His Lys Val Ile Thr Phe Trp
225             230             235                 240

Glu Lys Glu Gly Leu Leu Leu Tyr Cys Asp Leu Tyr Glu Ser Thr Phe
            245             250             255

Glu Lys Leu Lys Met Pro Ser Arg Lys Val Asp Ala Leu Asp His Phe
            260             265             270

Gln Lys Cys Phe Leu Ile Leu Lys Leu His Arg Glu Cys Val Asp Asp
            275             280             285

Gly Thr Ser Ser Gln Leu Gln Gly Lys Thr Trp Lys Ala Ile Arg Val
    290             295             300

Asp Leu Val Val Cys Pro Tyr Glu Cys Arg Ala Phe Ala Leu Leu Gly
305             310             315                 320

Trp Thr Gly Ser Pro Gln Phe Glu Arg Asp Leu Arg Arg Tyr Ala Thr
            325             330             335

His Glu Arg Lys Met Met Leu Asp Asn His Ala Leu Tyr Asp Lys Thr
            340             345             350

Lys Arg Lys Phe Leu Ser Ala Asp Ser Glu Glu Asp Ile Phe Ala His
            355             360             365

Leu Gly Leu Asp Tyr Ile Glu Pro Trp Glu Arg Asn Ala
    370             375             380
```

<210> SEQ ID NO 8
<211> LENGTH: 387
<212> TYPE: PRT
<213> ORGANISM: ARTIFICIAL SEQUENCE
<220> FEATURE:
<223> OTHER INFORMATION: Python truncated

<400> SEQUENCE: 8

```
Glu Lys Tyr Gln Leu Pro Glu Asp Glu Asp Arg Ser Val Thr Ser Asp
1               5                   10                  15

Leu Asp Arg Asp Ser Ile Ser Glu Tyr Ala Cys Gln Arg Arg Thr Thr
            20              25              30

Leu Lys Asn Tyr Asn Gln Lys Phe Thr Asp Ala Phe Glu Ile Leu Ala
            35              40              45

Glu Asn Tyr Glu Phe Asn Glu Asn Lys Gly Phe Cys Thr Ala Phe Arg
    50              55              60
```

```
Arg Ala Ala Ser Val Leu Lys Cys Leu Pro Phe Thr Ile Val Gln Val
65              70                  75                  80

His Asp Ile Glu Gly Val Pro Trp Met Gly Lys Gln Val Lys Gly Ile
                85                  90                  95

Ile Glu Asp Ile Ile Glu Glu Gly Glu Ser Ser Lys Val Lys Ala Val
                100                 105                 110

Leu Asp Asn Glu Asn Tyr Arg Ser Val Lys Leu Phe Thr Ser Val Phe
                115                 120                 125

Gly Val Gly Leu Lys Thr Ser Asp Lys Trp Tyr Arg Met Gly Leu Arg
        130                 135                 140

Thr Leu Glu Glu Val Lys Arg Asp Lys Asn Leu Lys Leu Thr Arg Met
145                 150                 155                 160

Gln Lys Ala Gly Phe Leu His Tyr Asp Asp Leu Thr Ser Cys Val Ser
                165                 170                 175

Lys Ala Glu Ala Asp Ala Ala Ser Leu Ile Val Gln Asp Val Val Trp
                180                 185                 190

Lys Ile Val Pro Asn Ala Ile Val Thr Ile Ala Gly Gly Phe Arg Arg
                195                 200                 205

Gly Lys Gln Thr Gly His Asp Val Asp Phe Leu Ile Thr Val Pro Gly
        210                 215                 220

Ser Lys Gln Glu Glu Glu Leu Leu His Thr Val Ile Asp Ile Trp
225                 230                 235                 240

Lys Lys Gln Glu Leu Leu Leu Tyr Tyr Asp Leu Ile Glu Ser Thr Phe
                245                 250                 255

Glu Asp Thr Lys Leu Pro Ser Arg Lys Val Asp Ala Leu Asp His Phe
                260                 265                 270

Gln Lys Cys Phe Ala Ile Leu Lys Val His Lys Glu Arg Glu Asp Lys
                275                 280                 285

Gly Asn Ser Ile Arg Ser Lys Ala Phe Ser Glu Glu Glu Ile Lys Asp
        290                 295                 300

Trp Lys Ala Ile Arg Val Asp Leu Val Val Val Pro Phe Glu Gln Tyr
305                 310                 315                 320

Ala Phe Ala Leu Leu Gly Trp Thr Gly Ser Thr Gln Phe Glu Arg Asp
                325                 330                 335

Leu Arg Arg Tyr Ala Thr His Glu Lys Lys Met Met Leu Asp Asn His
                340                 345                 350

Ala Leu Tyr Asp Lys Thr Lys Lys Ile Phe Leu Asn Ala Ala Ser Glu
                355                 360                 365

Glu Glu Ile Phe Ala His Leu Gly Leu Asp Tyr Leu Glu Pro Trp Glu
        370                 375                 380

Arg Asn Ala
385
```

<210> SEQ ID NO 9
<211> LENGTH: 381
<212> TYPE: PRT
<213> ORGANISM: ARTIFICIAL SEQUENCE
<220> FEATURE:
<223> OTHER INFORMATION: truncated dog

<400> SEQUENCE: 9

```
Asp Tyr Thr Ala Ser Pro Asn Pro Glu Leu Gln Lys Thr Leu Pro Val
1               5                   10                  15

Ala Val Lys Lys Ile Ser Gln Tyr Ala Cys Gln Arg Arg Thr Thr Leu
                20                  25                  30
```

-continued

```
Asn Asn Tyr Asn Asn Val Phe Thr Asp Ala Phe Glu Val Leu Ala Glu
        35              40              45

Asn Tyr Glu Phe Arg Glu Asn Glu Val Phe Ser Leu Thr Phe Met Arg
    50              55              60

Ala Ala Ser Val Leu Lys Ser Leu Pro Phe Thr Ile Ile Ser Met Lys
65              70              75              80

Asp Thr Glu Gly Ile Pro Cys Leu Gly Asp Gln Val Lys Cys Ile Ile
            85              90              95

Glu Glu Ile Ile Glu Asp Gly Glu Ser Ser Glu Val Lys Ala Val Leu
            100             105             110

Asn Asp Glu Arg Tyr Gln Ser Phe Lys Leu Phe Thr Ser Val Phe Gly
        115             120             125

Val Gly Leu Lys Thr Ser Glu Lys Trp Phe Arg Met Gly Phe Arg Thr
    130             135             140

Leu Ser Lys Ile Lys Ser Asp Lys Ser Leu Lys Phe Thr Pro Met Gln
145             150             155             160

Lys Ala Gly Phe Leu Tyr Tyr Glu Asp Leu Val Ser Cys Val Thr Arg
            165             170             175

Ala Glu Ala Glu Ala Val Gly Val Leu Val Lys Glu Ala Val Gly Ala
            180             185             190

Phe Leu Pro Asp Ala Phe Val Thr Met Thr Gly Gly Phe Arg Arg Gly
        195             200             205

Lys Lys Met Gly His Asp Val Asp Phe Leu Ile Thr Ser Pro Gly Ser
    210             215             220

Thr Asp Glu Asp Glu Glu Gln Leu Leu Pro Lys Val Ile Asn Leu Trp
225             230             235             240

Glu Arg Lys Gly Leu Leu Leu Tyr Cys Asp Leu Val Glu Ser Thr Phe
            245             250             255

Glu Lys Leu Lys Leu Pro Ser Arg Lys Val Asp Ala Leu Asp His Phe
            260             265             270

Gln Lys Cys Phe Leu Ile Leu Lys Leu His His Gln Arg Val Asp Gly
        275             280             285

Gly Lys Cys Ser Gln Gln Glu Gly Lys Thr Trp Lys Ala Ile Arg Val
    290             295             300

Asp Leu Val Met Cys Pro Tyr Glu Arg Arg Ala Phe Ala Leu Leu Gly
305             310             315             320

Trp Thr Gly Ser Arg Gln Phe Glu Arg Asp Leu Arg Arg Tyr Ala Ser
            325             330             335

His Glu Arg Lys Met Ile Leu Asp Asn His Ala Leu Tyr Asp Lys Thr
            340             345             350

Lys Lys Ile Phe Leu Lys Ala Glu Ser Glu Glu Glu Ile Phe Ala His
        355             360             365

Leu Gly Leu Asp Tyr Ile Glu Pro Trp Glu Arg Asn Ala
    370             375             380

<210> SEQ ID NO 10
<211> LENGTH: 382
<212> TYPE: PRT
<213> ORGANISM: ARTIFICIAL SEQUENCE
<220> FEATURE:
<223> OTHER INFORMATION: TRUNC MOLE

<400> SEQUENCE: 10

Gly Asp Cys Pro Ala Ser His Asp Ser Ser Pro Gln Lys Thr Glu Ser
1               5               10              15
```

-continued

```
Ala Ala Val Gln Lys Ile Ser Gln Tyr Ala Cys Gln Arg Arg Thr Thr
            20                  25                  30

Leu Asn Asn His Asn His Ile Phe Thr Asp Ala Phe Glu Ile Leu Ala
            35                  40                  45

Glu Asn Cys Glu Phe Arg Glu Asn Glu Gly Ser Tyr Val Thr Tyr Met
        50                  55                  60

Arg Ala Ala Ser Val Leu Lys Ser Leu Pro Phe Ser Ile Ile Ser Met
65                  70                  75                  80

Lys Asp Thr Glu Gly Ile Pro Cys Leu Ala Asp Lys Val Lys Cys Val
                85                  90                  95

Ile Glu Glu Ile Ile Glu Asp Gly Glu Ser Ser Glu Val Lys Ala Val
            100                 105                 110

Leu Asn Asp Glu Arg Tyr Lys Ser Phe Lys Leu Phe Thr Ser Val Phe
            115                 120                 125

Gly Val Gly Leu Lys Thr Ala Glu Lys Trp Phe Arg Leu Gly Phe Arg
        130                 135                 140

Thr Leu Ser Gly Ile Met Asn Asp Lys Thr Leu Lys Leu Thr His Met
145                 150                 155                 160

Gln Lys Ala Gly Phe Leu Tyr Tyr Glu Asp Leu Val Ser Cys Val Thr
                165                 170                 175

Arg Ala Glu Ala Glu Ala Val Gly Val Leu Val Lys Glu Ala Val Trp
            180                 185                 190

Ala Phe Leu Pro Asp Ala Ile Val Thr Met Thr Gly Gly Phe Arg Arg
            195                 200                 205

Gly Lys Lys Val Gly His Asp Val Asp Phe Leu Ile Thr Ser Pro Glu
        210                 215                 220

Ala Thr Glu Glu Gln Glu Gln Gln Leu Leu His Lys Val Ile Thr Phe
225                 230                 235                 240

Trp Glu Lys Glu Gly Leu Leu Leu Tyr Cys Asp Leu Tyr Glu Ser Thr
                245                 250                 255

Phe Glu Lys Leu Lys Met Pro Ser Arg Lys Val Asp Ala Leu Asp His
            260                 265                 270

Phe Gln Lys Cys Phe Leu Ile Leu Lys Leu His Arg Glu Cys Val Asp
            275                 280                 285

Asp Gly Thr Ser Ser Gln Leu Gln Gly Lys Thr Trp Lys Ala Ile Arg
        290                 295                 300

Val Asp Leu Val Val Cys Pro Tyr Glu Cys Arg Ala Phe Ala Leu Leu
305                 310                 315                 320

Gly Trp Thr Gly Ser Pro Gln Phe Glu Arg Asp Leu Arg Arg Tyr Ala
                325                 330                 335

Thr His Glu Arg Lys Met Met Leu Asp Asn His Ala Leu Tyr Asp Lys
            340                 345                 350

Thr Lys Arg Lys Phe Leu Ser Ala Asp Ser Glu Glu Asp Ile Phe Ala
            355                 360                 365

His Leu Gly Leu Asp Tyr Ile Glu Pro Trp Glu Arg Asn Ala
    370                 375                 380
```

```
<210> SEQ ID NO 11
<211> LENGTH: 379
<212> TYPE: PRT
<213> ORGANISM: ARTIFICIAL SEQUENCE
<220> FEATURE:
<223> OTHER INFORMATION: Pika trunk

<400> SEQUENCE: 11
```

```
Glu Tyr Ser Ala Asn Pro Ser Pro Gly Pro Gln Ala Thr Pro Ala Val
1               5                   10                  15

Tyr Lys Ile Ser Gln Tyr Ala Cys Gln Arg Arg Thr Thr Leu Asn Asn
                20                  25                  30

His Asn His Ile Phe Thr Asp Ala Phe Glu Ile Leu Ala Glu Asn Tyr
            35                  40                  45

Glu Phe Lys Glu Asn Glu Gly Cys Tyr Val Thr Tyr Met Arg Ala Ala
        50                  55                  60

Ser Val Leu Lys Ser Leu Pro Phe Thr Ile Val Ser Met Lys Asp Thr
65                  70                  75                  80

Glu Gly Ile Pro Cys Leu Glu Asp Lys Val Lys Ser Ile Met Glu Glu
                85                  90                  95

Ile Ile Glu Glu Gly Glu Ser Ser Glu Val Lys Ala Val Leu Ser Asp
            100                 105                 110

Glu Arg Tyr Gln Cys Phe Lys Leu Phe Thr Ser Val Phe Gly Val Gly
        115                 120                 125

Leu Lys Thr Ser Glu Lys Trp Phe Arg Met Gly Phe Arg Ser Leu Ser
        130                 135                 140

Asn Ile Arg Leu Asp Lys Ser Leu Lys Phe Thr Gln Met Gln Lys Ala
145                 150                 155                 160

Gly Phe Arg Tyr Tyr Glu Asp Ile Val Ser Cys Val Thr Arg Ala Glu
                165                 170                 175

Ala Glu Ala Val Asp Val Leu Val Asn Glu Ala Val Arg Ala Phe Leu
            180                 185                 190

Pro Asp Ala Phe Ile Thr Met Thr Gly Gly Phe Arg Arg Gly Lys Lys
        195                 200                 205

Ile Gly His Asp Val Asp Phe Leu Ile Thr Ser Pro Glu Leu Thr Glu
        210                 215                 220

Glu Asp Glu Gln Gln Leu Leu His Lys Val Met Asn Leu Trp Glu Lys
225                 230                 235                 240

Lys Gly Leu Leu Leu Tyr His Asp Leu Val Glu Ser Thr Phe Glu Lys
                245                 250                 255

Leu Lys Gln Pro Ser Arg Lys Val Asp Ala Leu Asp His Phe Gln Lys
            260                 265                 270

Cys Phe Leu Ile Phe Lys Leu Tyr His Glu Arg Val Gly Gly Asp Arg
        275                 280                 285

Cys Arg Gln Pro Glu Gly Lys Asp Trp Lys Ala Ile Arg Val Asp Leu
        290                 295                 300

Val Met Cys Pro Tyr Glu Cys His Ala Phe Ala Leu Leu Gly Trp Thr
305                 310                 315                 320

Gly Ser Arg Gln Phe Glu Arg Asp Leu Arg Arg Tyr Ala Ser His Glu
                325                 330                 335

Arg Lys Met Ile Leu Asp Asn His Ala Leu Tyr Asp Lys Thr Lys Arg
            340                 345                 350

Val Phe Leu Gln Ala Glu Asn Glu Glu Glu Ile Phe Ala His Leu Gly
        355                 360                 365

Leu Asp Tyr Ile Glu Pro Trp Glu Arg Asn Ala
        370                 375
```

<210> SEQ ID NO 12
<211> LENGTH: 384
<212> TYPE: PRT
<213> ORGANISM: ARTIFICIAL SEQUENCE
<220> FEATURE:
<223> OTHER INFORMATION: TRUNC HEDGEHOG

-continued

<400> SEQUENCE: 12

```
Asp Ala Ser Phe Gly Ser Asn Pro Gly Ser Gln Asn Thr Pro Pro Leu
1               5                   10                  15

Ala Ile Lys Lys Ile Ser Gln Tyr Ala Cys Gln Arg Arg Thr Ser Leu
                20                  25                  30

Asn Asn Cys Asn His Ile Phe Thr Asp Ala Leu Asp Ile Leu Ala Glu
            35                  40                  45

Asn His Glu Phe Arg Glu Asn Glu Val Ser Cys Val Ala Phe Met Arg
        50                  55                  60

Ala Ala Ser Val Leu Lys Ser Leu Pro Phe Thr Ile Ile Ser Met Lys
65                  70                  75                  80

Asp Thr Lys Gly Ile Pro Cys Leu Gly Asp Lys Ala Lys Cys Val Ile
                85                  90                  95

Glu Glu Ile Ile Glu Asp Gly Glu Ser Ser Glu Val Lys Ala Ile Leu
            100                 105                 110

Asn Asp Glu Arg Tyr Gln Ser Phe Lys Leu Phe Thr Ser Val Phe Gly
        115                 120                 125

Val Gly Leu Lys Thr Ser Glu Lys Trp Phe Arg Met Gly Phe Arg Thr
    130                 135                 140

Leu Asn Lys Ile Met Ser Asp Lys Thr Leu Lys Leu Thr Arg Met Gln
145                 150                 155                 160

Lys Ala Gly Phe Leu Tyr Tyr Glu Asp Leu Val Ser Cys Val Ala Lys
                165                 170                 175

Ala Glu Ala Asp Ala Val Ser Val Leu Val Gln Glu Ala Val Trp Ala
            180                 185                 190

Phe Leu Pro Asp Ala Met Val Thr Met Thr Gly Gly Phe Arg Arg Gly
        195                 200                 205

Lys Lys Leu Gly His Asp Val Asp Phe Leu Ile Thr Ser Pro Gly Ala
    210                 215                 220

Thr Glu Glu Glu Glu Gln Gln Leu Leu Pro Lys Val Ile Asn Phe Trp
225                 230                 235                 240

Glu Arg Lys Gly Leu Leu Leu Tyr His Asp Leu Val Glu Ser Thr Phe
                245                 250                 255

Glu Lys Leu Lys Leu Pro Ser Arg Lys Val Asp Ala Leu Asp His Phe
            260                 265                 270

Gln Lys Cys Phe Leu Ile Leu Lys Leu His Leu Gln His Val Asn Gly
        275                 280                 285

Val Gly Asn Ser Lys Thr Gly Gln Gln Glu Gly Lys Asn Trp Lys Ala
    290                 295                 300

Ile Arg Val Asp Leu Val Met Cys Pro Tyr Glu Arg Arg Ala Phe Ala
305                 310                 315                 320

Leu Leu Gly Trp Thr Gly Ser Arg Gln Phe Glu Arg Asp Leu Arg Arg
                325                 330                 335

Phe Ala Thr His Glu Arg Lys Met Met Leu Asp Asn His Ala Leu Tyr
            340                 345                 350

Asp Lys Thr Lys Arg Ile Phe Leu Lys Ala Glu Ser Glu Glu Glu Ile
        355                 360                 365

Phe Ala His Leu Gly Leu Asp Tyr Ile Asp Pro Trp Glu Arg Asn Ala
    370                 375                 380
```

<210> SEQ ID NO 13
<211> LENGTH: 381
<212> TYPE: PRT

<213> ORGANISM: ARTIFICIAL SEQUENCE
<220> FEATURE:
<223> OTHER INFORMATION: truncated tree shrew

<400> SEQUENCE: 13

```
Asp His Ser Thr Ser Pro Ser Pro Gly Pro Gln Lys Thr Pro Ala Leu
1               5                   10                  15

Ala Val Gln Lys Ile Ser Gln Tyr Ala Cys Gln Arg Arg Thr Thr Leu
                20                  25                  30

Asn Asn Cys Asn Arg Val Phe Thr Asp Ala Phe Glu Thr Leu Ala Glu
            35                  40                  45

Asn Tyr Glu Phe Arg Glu Asn Glu Asp Ser Ser Val Ile Phe Leu Arg
        50                  55                  60

Ala Ala Ser Val Leu Arg Ser Leu Pro Phe Thr Ile Thr Ser Met Arg
65                  70                  75                  80

Asp Thr Glu Gly Leu Pro Cys Leu Gly Asp Lys Val Lys Cys Val Ile
                85                  90                  95

Glu Glu Ile Ile Glu Asp Gly Glu Ser Ser Glu Val Asn Ala Val Leu
            100                 105                 110

Asn Asp Glu Arg Tyr Lys Ser Phe Lys Leu Phe Thr Ser Val Phe Gly
        115                 120                 125

Val Gly Leu Lys Thr Ser Glu Lys Trp Phe Arg Met Gly Phe Arg Thr
    130                 135                 140

Leu Ser Arg Val Arg Ser Asp Lys Ser Leu His Leu Thr Arg Met Gln
145                 150                 155                 160

Gln Ala Gly Phe Leu Tyr Tyr Glu Asp Leu Ala Ser Cys Val Thr Arg
                165                 170                 175

Ala Glu Ala Glu Ala Val Gly Val Leu Val Lys Glu Ala Val Gly Ala
            180                 185                 190

Phe Leu Pro Asp Ala Leu Val Thr Ile Thr Gly Gly Phe Arg Arg Gly
        195                 200                 205

Lys Lys Thr Gly His Asp Val Asp Phe Leu Ile Thr Ser Pro Gly Ser
    210                 215                 220

Thr Glu Glu Lys Glu Glu Glu Leu Leu Gln Lys Val Leu Asn Leu Trp
225                 230                 235                 240

Glu Lys Lys Gly Leu Leu Leu Tyr Tyr Asp Leu Val Glu Ser Thr Phe
                245                 250                 255

Glu Lys Leu Lys Thr Pro Ser Arg Lys Val Asp Ala Leu Asp His Phe
            260                 265                 270

Pro Lys Cys Phe Leu Ile Leu Lys Leu His His Gln Arg Val Asp Gly
        275                 280                 285

Asp Lys Pro Ser Gln Gln Glu Gly Lys Ser Trp Lys Ala Ile Arg Val
    290                 295                 300

Asp Leu Val Met Cys Pro Tyr Glu Arg His Ala Phe Ala Leu Leu Gly
305                 310                 315                 320

Trp Thr Gly Ser Arg Gln Phe Glu Arg Asp Leu Arg Arg Tyr Ala Thr
                325                 330                 335

His Glu Arg Lys Met Met Leu Asp Asn His Ala Leu Tyr Asp Lys Thr
            340                 345                 350

Lys Arg Val Phe Leu Lys Ala Glu Ser Glu Glu Asp Ile Phe Ala His
        355                 360                 365

Leu Gly Leu Asp Tyr Ile Glu Pro Trp Glu Arg Asn Ala
    370                 375                 380
```

```
<210> SEQ ID NO 14
<211> LENGTH: 394
<212> TYPE: PRT
<213> ORGANISM: ARTIFICIAL SEQUENCE
<220> FEATURE:
<223> OTHER INFORMATION: TRUNCATED PLATYPUS

<400> SEQUENCE: 14

Leu Thr Asn Ser Ala Pro Ile Asn Cys Met Thr Glu Thr Pro Ser Leu
1               5                   10                  15

Ala Thr Lys Gln Val Ser Gln Tyr Ala Cys Glu Arg Arg Thr Thr Leu
            20                  25                  30

Asn Asn Cys Asn Gln Lys Phe Thr Asp Ala Phe Glu Ile Leu Ala Lys
        35                  40                  45

Asp Phe Glu Phe Arg Glu Asn Glu Gly Ile Cys Leu Ala Phe Met Arg
    50                  55                  60

Ala Ile Ser Val Leu Lys Cys Leu Pro Phe Thr Ile Val Arg Met Lys
65                  70                  75                  80

Asp Ile Glu Gly Val Pro Trp Leu Gly Asp Gln Val Lys Ser Ile Ile
                85                  90                  95

Glu Glu Ile Ile Glu Asp Gly Glu Ser Ser Ser Val Lys Ala Val Leu
            100                 105                 110

Asn Asp Glu Arg Tyr Arg Ser Phe Gln Leu Phe Asn Ser Val Phe Glu
        115                 120                 125

Val Gly Leu Thr Asp Asn Gly Glu Asn Gly Ile Ala Arg Gly Phe Gln
    130                 135                 140

Thr Leu Asn Glu Val Ile Thr Asp Glu Asn Ile Ser Leu Thr Lys Thr
145                 150                 155                 160

Thr Leu Ser Thr Ser Leu Trp Asn Tyr Leu Pro Gly Phe Leu Tyr Tyr
                165                 170                 175

Glu Asp Leu Val Ser Cys Val Ala Lys Glu Glu Ala Asp Ala Val Tyr
            180                 185                 190

Leu Ile Val Lys Glu Ala Val Arg Ala Phe Leu Pro Glu Ala Leu Val
            195                 200                 205

Thr Leu Thr Gly Gly Phe Arg Arg Gly Lys Lys Ile Gly His Asp Val
    210                 215                 220

Asp Phe Leu Ile Ser Asp Pro Glu Ser Gly Gln Asp Glu Gln Leu Leu
225                 230                 235                 240

Pro Asn Ile Ile Lys Leu Trp Glu Lys Gln Glu Leu Leu Leu Tyr Tyr
                245                 250                 255

Asp Leu Val Glu Ser Thr Phe Glu Lys Thr Lys Ile Pro Ser Arg Lys
            260                 265                 270

Val Asp Ala Met Asp His Phe Gln Lys Cys Phe Leu Ile Leu Lys Leu
            275                 280                 285

His His Gln Lys Val Asp Ser Gly Arg Tyr Lys Pro Pro Pro Glu Ser
        290                 295                 300

Lys Asn His Glu Ala Lys Asn Trp Lys Ala Ile Arg Val Asp Leu Val
305                 310                 315                 320

Met Cys Pro Phe Glu Gln Tyr Ala Tyr Ala Leu Leu Gly Trp Thr Gly
                325                 330                 335

Ser Arg Gln Phe Glu Arg Asp Leu Arg Arg Tyr Ala Thr His Glu Lys
            340                 345                 350

Lys Met Met Leu Asp Asn His Ala Leu Tyr Asp Lys Thr Lys Lys Ile
        355                 360                 365

Phe Leu Lys Ala Glu Ser Glu Glu Asp Ile Phe Thr His Leu Gly Leu
```

```
        370              375              380
Asp Tyr Ile Glu Pro Trp Glu Arg Asn Ala
385              390

<210> SEQ ID NO 15
<211> LENGTH: 384
<212> TYPE: PRT
<213> ORGANISM: ARTIFICIAL SEQUENCE
<220> FEATURE:
<223> OTHER INFORMATION: TRUNCATED JERBOA

<400> SEQUENCE: 15

Ser Ser Glu Leu Glu Leu Leu Asp Val Ser Trp Leu Ile Glu Cys Met
1               5                  10                  15

Gly Ala Gly Lys Pro Val Glu Met Thr Gly Arg His Gln Leu Val Lys
            20                  25                  30

Gln Thr Phe Cys Leu Pro Gly Phe Ile Leu Gln Asp Ala Phe Asp Ile
        35                  40                  45

Leu Ala Glu Asn Cys Glu Phe Arg Glu Asn Glu Ala Ser Cys Val Glu
    50                  55                  60

Phe Met Arg Ala Ala Ser Val Leu Lys Ser Leu Pro Phe Pro Ile Ile
65                  70                  75                  80

Ser Val Lys Asp Thr Glu Gly Ile Pro Trp Leu Gly Gly Lys Val Lys
            85                  90                  95

Cys Val Ile Glu Glu Ile Ile Glu Asp Gly Glu Ser Ser Glu Val Lys
            100                 105                 110

Ala Leu Leu Asn Asp Glu Arg Tyr Lys Ser Phe Lys Leu Phe Thr Ser
        115                 120                 125

Val Phe Gly Val Gly Leu Lys Thr Ala Glu Arg Trp Phe Arg Met Gly
    130                 135                 140

Phe Arg Thr Leu Ser Thr Val Lys Leu Asp Lys Ser Leu Thr Phe Thr
145                 150                 155                 160

Arg Met Gln Lys Ala Gly Phe Leu His Tyr Glu Asp Leu Val Ser Cys
                165                 170                 175

Val Thr Arg Ala Glu Ala Glu Ala Val Ser Val Leu Val Gln Gln Ala
            180                 185                 190

Val Val Ala Phe Leu Pro Asp Ala Leu Val Ser Met Thr Gly Gly Phe
        195                 200                 205

Arg Arg Gly Lys Lys Ile Gly His Asp Val Asp Phe Leu Ile Thr Ser
    210                 215                 220

Pro Glu Ala Thr Glu Glu Glu Glu Gln Gln Leu Leu His Lys Val Thr
225                 230                 235                 240

Asn Phe Trp Glu Gln Lys Gly Leu Leu Leu Tyr Cys Asp His Val Glu
                245                 250                 255

Ser Thr Phe Glu Lys Cys Lys Leu Pro Ser Arg Lys Val Asp Ala Leu
            260                 265                 270

Asp His Phe Gln Lys Cys Phe Leu Ile Leu Lys Leu Tyr Arg Glu Arg
        275                 280                 285

Val Asp Ser Val Lys Ser Ser Gln Gln Glu Gly Lys Gly Trp Lys Ala
    290                 295                 300

Ile Arg Val Asp Leu Val Met Cys Pro Tyr Glu Cys Arg Ala Phe Ala
305                 310                 315                 320

Leu Leu Gly Trp Thr Gly Ser Arg Gln Phe Glu Arg Asp Leu Arg Arg
                325                 330                 335

Tyr Ala Thr His Glu Arg Lys Met Arg Leu Asp Asn His Ala Leu Tyr
```

-continued

```
                 340              345              350
Asp Lys Thr Lys Arg Val Phe Leu Lys Ala Glu Ser Glu Glu Glu Ile
            355              360              365
Phe Ala His Leu Gly Leu Glu Tyr Ile Glu Pro Leu Glu Arg Asn Ala
        370              375              380

<210> SEQ ID NO 16
<211> LENGTH: 382
<212> TYPE: PRT
<213> ORGANISM: ARTIFICIAL SEQUENCE
<220> FEATURE:
<223> OTHER INFORMATION: trunc wt Serinus canaria (canary)

<400> SEQUENCE: 16

Ser Pro Pro Leu Asn Thr Pro Glu Leu Glu Met Pro Ser Phe Ile Ala
1               5              10              15
Thr Lys Val Ser Gln Tyr Ser Cys Gln Arg Lys Thr Thr Leu Asn Asn
            20              25              30
Tyr Asn Lys Lys Phe Thr Asp Ala Phe Glu Val Met Ala Glu Asn Tyr
        35              40              45
Glu Phe Lys Glu Asn Glu Ile Phe Cys Leu Glu Phe Leu Arg Ala Ala
    50              55              60
Ser Leu Leu Lys Ser Leu Pro Phe Ser Val Thr Arg Met Lys Asp Ile
65              70              75              80
Gln Gly Leu Pro Cys Met Gly Asp Gln Val Arg Asp Val Ile Glu Ile
            85              90              95
Ile Glu Glu Gly Glu Ser Ser Arg Val Lys Glu Val Leu Asn Asp Glu
            100             105             110
Arg Tyr Lys Ala Phe Lys Gln Phe Thr Ser Val Phe Gly Val Gly Val
        115             120             125
Lys Thr Ser Glu Lys Trp Tyr Arg Met Gly Leu Arg Thr Val Gly Glu
    130             135             140
Val Lys Ala Asp Lys Thr Leu Lys Leu Ser Lys Met Gln Lys Ala Gly
145             150             155             160
Phe Leu Tyr Tyr Glu Asp Leu Val Ser Cys Val Ser Lys Ala Glu Ala
            165             170             175
Asp Ala Val Ser Leu Ile Val Lys Asn Thr Val Cys Thr Phe Leu Pro
        180             185             190
Asp Ala Leu Val Thr Ile Thr Gly Gly Phe Arg Arg Gly Lys Asn Ile
        195             200             205
Gly His Asp Ile Asp Phe Leu Ile Thr Asn Pro Gly Pro Arg Glu Asp
    210             215             220
Asp Glu Leu Leu His Lys Val Ile Asp Leu Trp Lys Lys Gln Gly Leu
225             230             235             240
Leu Leu Tyr Cys Asp Ile Ile Glu Ser Thr Phe Val Lys Glu Gln Leu
            245             250             255
Pro Ser Arg Lys Ile Asp Ala Met Asp His Phe Gln Lys Cys Phe Ala
        260             265             270
Ile Leu Lys Leu Tyr Gln Pro Arg Val Asp Asn Ser Thr Cys Asn Thr
        275             280             285
Ser Lys Lys Leu Glu Met Ala Glu Val Lys Asp Trp Lys Ala Ile Arg
    290             295             300
Val Asp Leu Val Ile Thr Pro Phe Glu Gln Tyr Ser Tyr Ala Leu Leu
305             310             315             320
Gly Trp Thr Gly Ser Arg Gln Phe Gly Arg Asp Leu Arg Arg Tyr Ala
```

-continued

```
                325                   330                   335
Ala His Glu Arg Arg Met Ile Leu Asp Asn His Gly Leu Tyr Asp Arg
            340                   345                   350

Thr Lys Arg Ile Phe Leu Lys Ala Gly Ser Glu Glu Glu Ile Phe Ala
            355                   360                   365

His Leu Gly Leu Asp Tyr Val Glu Pro Trp Glu Arg Asn Ala
            370                   375                   380

<210> SEQ ID NO 17
<211> LENGTH: 370
<212> TYPE: PRT
<213> ORGANISM: ARTIFICIAL SEQUENCE
<220> FEATURE:
<223> OTHER INFORMATION: trunc wt Neopelma chrysocephalum (saffron-
      crested neopelma)

<400> SEQUENCE: 17

Phe Ile Ala Arg Lys Val Ser Gln Tyr Ser Cys Gln Arg Lys Thr Thr
1               5                   10                  15

Leu Asn Asn Tyr Asn Lys Lys Phe Thr Asp Ala Phe Glu Ile Met Ala
                20                  25                  30

Glu Asn Tyr Glu Phe Lys Glu Asn Glu Ile Phe Cys Leu Glu Phe Leu
            35                  40                  45

Arg Ala Ala Ser Leu Leu Lys Tyr Leu Pro Phe Pro Val Thr Arg Met
        50                  55                  60

Lys Asp Ile Gln Gly Leu Pro Cys Ile Gly Asp Gln Val Arg Asp Val
65                  70                  75                  80

Ile Glu Gly Ile Ile Glu Glu Gly Glu Ser Ser Arg Val Lys Glu Val
                    85                  90                  95

Leu Asn Asp Glu Arg Tyr Lys Ala Phe Lys Gln Phe Thr Ser Val Phe
                100                 105                 110

Gly Val Gly Val Lys Thr Ser Glu Lys Trp Tyr Arg Met Gly Leu Arg
            115                 120                 125

Thr Val Glu Glu Leu Lys Ala Asp Lys Thr Leu Lys Leu Ser Lys Met
        130                 135                 140

Gln Lys Ala Gly Phe Leu Tyr Tyr Glu Asp Leu Val Ser Cys Val Ser
145                 150                 155                 160

Lys Ala Glu Ala Asp Ala Val Thr Leu Ile Val Lys Asn Thr Val Ser
                165                 170                 175

Thr Phe Leu Pro Asp Ala Leu Val Thr Ile Thr Gly Gly Phe Arg Arg
                180                 185                 190

Gly Lys Lys Met Gly His Asp Ile Asp Phe Leu Ile Thr Asn Pro Gly
            195                 200                 205

Pro Arg Glu Asp Asp Glu Leu Leu His Lys Val Val Asp Leu Trp Lys
        210                 215                 220

Lys Gln Gly Leu Leu Leu Tyr Cys Asp Ile Ile Glu Ser Thr Phe Val
225                 230                 235                 240

Glu Glu Gln Leu Pro Ser Arg Lys Val Asp Ala Met Asp Asn Phe Gln
                245                 250                 255

Lys Cys Phe Thr Ile Leu Lys Leu Tyr Gln Pro Gly Val Asp Asn Ser
            260                 265                 270

Ser Tyr Asn Met Ser Lys Lys Ser Asp Met Ala Glu Val Lys Asp Trp
            275                 280                 285

Lys Ala Ile Arg Val Asp Leu Val Ile Thr Pro Phe Glu Gln Tyr Ala
        290                 295                 300
```

-continued

```
Tyr Ala Leu Leu Gly Trp Thr Gly Ser Arg Glu Phe Gly Arg Asp Leu
305             310             315             320

Arg Arg Tyr Ala Ser His Glu Arg Lys Met Ile Leu Asp Asn His Gly
                325             330             335

Leu Tyr Asp Arg Arg Lys Arg Ile Phe Leu Lys Ala Gly Ser Glu Glu
            340             345             350

Glu Ile Phe Ala His Leu Gly Leu Asp Tyr Val Glu Pro Trp Glu Arg
        355             360             365

Asn Ala
    370

<210> SEQ ID NO 18
<211> LENGTH: 383
<212> TYPE: PRT
<213> ORGANISM: ARTIFICIAL SEQUENCE
<220> FEATURE:
<223> OTHER INFORMATION: trunc wt  Alligator sinensis

<400> SEQUENCE: 18

Ser Pro Ser Pro Val Pro Gly Ser Gln Asn Val Pro Ala Pro Ser Val
1               5               10              15

Asp Lys Val Ser Gln Tyr Ala Cys Gln Arg Arg Thr Thr Leu Asn Asn
                20              25              30

Tyr Asn Lys Lys Phe Thr Asp Ala Phe Glu Ile Leu Ala Glu Asn Cys
            35              40              45

Glu Phe Arg Glu Asn Arg Leu Gly Cys Leu Glu Phe Leu Arg Ala Ala
        50              55              60

Ser Val Leu Lys Phe Leu Pro Phe Pro Ile Val Lys Met Lys Asn Ile
65              70              75              80

Glu Gly Leu Pro Cys Met Gly Asp Lys Val Lys Cys Val Ile Glu Glu
                85              90              95

Ile Leu Glu Glu Gly Glu Ser Cys Gln Ala Lys Glu Ile Leu Asn Asp
            100             105             110

Glu Arg Tyr Lys Ser Phe Lys Leu Phe Thr Ser Val Phe Gly Val Gly
        115             120             125

Leu Lys Thr Thr Glu Lys Trp Tyr Arg Met Gly Phe Arg Thr Leu Glu
    130             135             140

Glu Val Lys Ala Glu Lys Thr Leu Lys Leu Ser Arg Met Gln Ile Ala
145             150             155             160

Gly Phe Leu His Tyr Glu Asp Ile Ile Ser Tyr Val Ser Lys Ala Glu
            165             170             175

Ala Asp Ala Val Ser Leu Leu Ile Lys Asp Thr Val Cys Met Phe Leu
            180             185             190

Pro Asp Ala Leu Val Thr Ile Thr Gly Gly Phe Arg Arg Gly Lys Lys
        195             200             205

Thr Gly His Asp Val Asp Phe Leu Ile Thr Asn Pro Gly Pro Glu Glu
    210             215             220

Glu Lys Glu Leu Leu His Lys Val Val Asp Leu Trp Glu Lys Gln Gly
225             230             235             240

Leu Leu Leu Tyr Tyr Asp Val Ile Glu Ser Thr Phe Glu Lys Glu Lys
            245             250             255

Arg Pro Ser Arg Lys Val Asp Ala Leu Asp His Phe Gln Lys Cys Phe
            260             265             270

Ala Ile Leu Lys Leu His Gln Gln Arg Arg Gly Asn Ser Asn Ser Asn
        275             280             285
```

-continued

```
Ile Ser Lys Glu Ser Asp Lys Ala Glu Val Lys Asp Trp Lys Ala Ile
    290             295             300

Arg Val Asp Leu Val Ile Ser Pro Phe Glu Gln Tyr Ala Tyr Ala Leu
305             310             315             320

Leu Gly Trp Thr Gly Ser Arg Gln Phe Glu Arg Asp Leu Arg Arg Tyr
            325             330             335

Ala Ser Arg Glu Arg Lys Met Met Leu Asp Asn His Ala Leu Tyr Asp
            340             345             350

Lys Thr Lys Arg Thr Phe Leu Lys Ala Glu Ser Glu Glu Glu Ile Phe
            355             360             365

Ala His Leu Gly Leu Asp Tyr Ile Glu Pro Trp Glu Arg Asn Ala
    370             375             380

<210> SEQ ID NO 19
<211> LENGTH: 380
<212> TYPE: PRT
<213> ORGANISM: ARTIFICIAL SEQUENCE
<220> FEATURE:
<223> OTHER INFORMATION: trunc wt  Xenopus laevis

<400> SEQUENCE: 19

Ser Pro Ser Pro Val Pro Gly Ser Gln Asn Val Pro Ala Pro Ser Glu
1               5               10              15

Val Lys Val Ser Gln Tyr Ala Cys Gln Arg Cys Thr Thr Leu Gln Asp
            20              25              30

Thr Asn Arg Ile Phe Thr Asp Ala Phe Asp Ile Leu Ala Glu His Phe
            35              40              45

Glu Phe Cys Glu Asn Lys Gly Arg Thr Val Ala Phe Leu Arg Ala Ser
    50              55              60

Ser Leu Ile Lys Ser Leu Pro Phe Pro Ile Thr Ala Met Lys Glu Leu
65              70              75              80

Glu Gly Leu Pro Trp Leu Gly Asp Gln Met Lys Gly Ile Ile Glu Glu
            85              90              95

Ile Leu Glu Glu Gly Lys Ser Tyr Lys Val Leu Glu Val Met Asn Glu
            100             105             110

Glu Arg Tyr Lys Ser Phe Lys Gln Phe Thr Ser Val Phe Gly Val Gly
            115             120             125

Leu Lys Thr Ser Asp Lys Trp Phe Arg Met Gly Phe Arg Thr Leu Glu
    130             135             140

Glu Ile Lys Asn Glu Lys Glu Leu Lys Leu Thr Lys Met Gln Lys Cys
145             150             155             160

Gly Leu Leu Tyr Tyr Glu Asp Ile Thr Ser Tyr Val Ser Arg Ala Glu
            165             170             175

Ala Glu Thr Thr Glu Gln Leu Ile Lys Ser Ile Val Trp Lys Phe Val
            180             185             190

Pro Asp Ala Ile Val Thr Leu Thr Gly Gly Phe Arg Arg Gly Lys Lys
            195             200             205

Lys Gly His Asp Val Asp Ile Leu Ile Thr Cys Ala Arg Lys Gly Lys
    210             215             220

Glu Lys Asn Ile Leu His Asn Thr Met Ser Val Leu Lys Asn Arg Gly
225             230             235             240

Leu Leu Leu Phe Tyr Asn Ile Ile Glu Ser Thr Phe Asp Glu Thr Lys
            245             250             255

Leu Pro Ser Arg His Val Asp Ala Leu Asp His Phe Gln Lys Cys Phe
            260             265             270
```

-continued

```
Thr Ile Leu Lys Leu Pro Lys Arg Gln Met Asp Ile Gly Asn Ile Ile
        275             280             285

Asp Pro His Glu Cys Glu Arg Lys Asn Trp Lys Ala Val Arg Leu Asp
    290             295             300

Leu Val Ile Thr Pro Tyr Glu Gln Tyr Pro Tyr Ala Leu Leu Gly Trp
305             310             315             320

Thr Gly Ser Arg Gln Phe Glu Arg Asp Leu Arg Arg Tyr Ala Thr His
            325             330             335

Glu Lys Arg Met Met Leu Asp Asn His Gly Leu Tyr Asp Lys Thr Lys
            340             345             350

Asn Asn Phe Leu Lys Ala Asn Asn Glu Glu Asp Ile Phe Lys Gln Leu
        355             360             365

Gly Leu Asp Tyr Leu Glu Pro Trp Glu Arg Asn Ala
        370             375             380

<210> SEQ ID NO 20
<211> LENGTH: 383
<212> TYPE: PRT
<213> ORGANISM: ARTIFICIAL SEQUENCE
<220> FEATURE:
<223> OTHER INFORMATION: trunc wt (Notechis scutatus) tiger snake

<400> SEQUENCE: 20

Ser Pro Ser Pro Val Pro Gly Ser Gln Asn Val Pro Ala Pro Ser Val
1               5               10              15

Asp Ser Ile Ser Pro Tyr Ala Cys Gln Arg Arg Thr Thr Leu Lys Asn
            20              25              30

Tyr Asn Gln Lys Phe Thr Asp Ala Phe Glu Ile Leu Val Glu Asn Tyr
        35              40              45

Glu Phe Asn Glu Asn Lys Glu Phe Cys Leu Ala Phe Gly Arg Ala Ala
    50              55              60

Ser Leu Leu Lys Cys Leu Pro Phe Thr Val Val Arg Val Asn Asp Ile
65              70              75              80

Glu Gly Leu Pro Trp Met Gly Lys Gln Val Arg Glu Ile Ile Glu Asp
            85              90              95

Ile Leu Glu Glu Gly Glu Ser Ser Lys Val Lys Ala Val Leu Asn Asp
            100             105             110

Glu Asn Tyr Arg Ser Ile Lys Leu Phe Thr Ser Val Phe Gly Val Gly
            115             120             125

Leu Arg Thr Ser Glu Lys Trp Tyr Arg Met Gly Leu Arg Thr Leu Glu
        130             135             140

Glu Val Lys Cys Asn Lys Asn Leu Thr Leu Thr Arg Met Gln Lys Ala
145             150             155             160

Gly Phe Phe Tyr Tyr Asp Asp Leu Ile Ser Ser Val Ser Lys Ala Glu
            165             170             175

Ala Asp Ala Ala Thr Gln Ile Val Gln Asp Thr Val Trp Lys Ile Leu
            180             185             190

Pro Asn Ala Val Val Thr Leu Thr Gly Gly Phe Arg Arg Gly Lys Gln
        195             200             205

Thr Gly His Asp Val Asp Phe Leu Ile Thr Val Pro Gly Ser Arg Gln
    210             215             220

Glu Glu Glu Leu Leu His Pro Val Ile Asp Ile Trp Lys Lys Gln Glu
225             230             235             240

Leu Leu Leu Tyr Tyr Asp Leu Ile Glu Ser Thr Phe Glu Asn Thr Lys
            245             250             255
```

-continued

```
Leu Pro Ser Arg Lys Val Asp Ala Leu Asp His Phe Gln Lys Cys Phe
            260             265             270

Ala Ile Leu Lys Val His Lys Glu Arg Val Asn Lys Gly Ser Ala Val
            275             280             285

Gln Ser Asn Val Phe Ala Glu Glu Gly Thr Lys Asp Trp Lys Ala Ile
            290             295             300

Arg Val Asp Leu Val Val Thr Pro Phe Gln His Tyr Ala Phe Ala Leu
305             310             315             320

Leu Gly Trp Thr Gly Ser Arg Gln Phe Glu Arg Asp Leu Arg Arg Tyr
            325             330             335

Ala Thr Gln Glu Lys Lys Met Met Leu Asp Asn His Ala Leu Tyr Asp
            340             345             350

Lys Thr Lys Lys Ile Phe Leu Ser Ala Ala Asn Glu Glu Glu Ile Phe
            355             360             365

Ser His Leu Gly Leu Asp Tyr Leu Glu Pro Trp Glu Arg Asn Ala
            370             375             380
```

```
<210> SEQ ID NO 21
<211> LENGTH: 367
<212> TYPE: PRT
<213> ORGANISM: ARTIFICIAL SEQUENCE
<220> FEATURE:
<223> OTHER INFORMATION: trunc wt (Salmo trutta) brown trout

<400> SEQUENCE: 21
```

```
Thr Ala Ala Ala Asn Val Ser Gln Tyr Ala Cys Leu Arg Arg Thr Thr
1               5               10              15

Thr Glu Asn His Asn Lys Ile Phe Thr Asp Val Leu Glu Glu Leu Ala
            20              25              30

Glu Asn Ser Glu Phe Asn Glu Ser Lys Gly Pro Cys Leu Ala Phe Arg
            35              40              45

Arg Ala Ala Ser Val Leu Lys Ser Leu Pro Ser Ala Val His Cys Leu
            50              55              60

Gly Ala Ile Gln Gly Leu Pro Cys Leu Gly Glu His Thr Lys Ala Val
65              70              75              80

Met Glu Glu Ile Leu Ile Phe Gly Arg Ser Phe Lys Val Glu Glu Val
            85              90              95

Gln Ser Asp Glu Arg Tyr Gln Ala Leu Lys Leu Phe Thr Ser Val Phe
            100             105             110

Gly Val Gly Pro Lys Thr Ala Glu Lys Trp Tyr Arg Arg Gly Leu Arg
            115             120             125

Ser Leu Lys Glu Ile Leu Ala Glu Pro Asn Ile Gln Leu Asn Arg Met
            130             135             140

Gln Arg Ala Gly Phe Leu Tyr Tyr Arg Asp Ile Ser Lys Ala Val Ser
145             150             155             160

Lys Ala Glu Ala Lys Ala Leu Ser Ser Ile Ile Glu Glu Thr Ala His
            165             170             175

Trp Ile Ala Pro Asp Ser Ile Leu Ala Leu Thr Gly Gly Phe Arg Arg
            180             185             190

Gly Lys Glu Tyr Gly His Asp Val Asp Phe Leu Leu Thr Met Pro Glu
            195             200             205

Met Gly Lys Glu Glu Gly Leu Leu Leu Arg Val Ile Asp Arg Leu Arg
            210             215             220

Asp Gln Gly Ile Leu Leu Tyr Cys Glu His Gln Asp Ser Thr Phe Asp
225             230             235             240
```

```
Met Ser Lys Leu Pro Ser His Arg Phe Glu Ala Met Asp His Phe Glu
            245             250             255

Lys Cys Phe Leu Ile Leu Arg Leu Glu Glu Gly Gln Val Glu Gly Asp
            260             265             270

Gly Gly Leu Gln Lys Asp Pro Gly Glu Ser Arg Gly Trp Arg Ala Val
            275             280             285

Arg Val Asp Leu Val Ala Pro Pro Val Asp Arg Tyr Ala Phe Val Leu
            290             295             300

Leu Gly Trp Thr Gly Ser Arg Gln Phe Glu Arg Asp Leu Arg Arg Phe
305             310             315             320

Ala Ser Lys Glu Arg Gly Met Cys Leu Asp Asn His Ala Leu Tyr Asp
            325             330             335

Lys Thr Lys Lys Leu Phe Leu Pro Ala Thr Ser Glu Glu Asp Ile Phe
            340             345             350

Ala His Leu Gly Leu Glu Tyr Val Glu Pro Trp Gln Arg Asn Ala
            355             360             365
```

<210> SEQ ID NO 22
<211> LENGTH: 377
<212> TYPE: PRT
<213> ORGANISM: ARTIFICIAL SEQUENCE
<220> FEATURE:
<223> OTHER INFORMATION: trunc wt (Electrophorus electricus) electric
      eel

<400> SEQUENCE: 22

```
Ser Pro Ser Pro Val Pro Gly Ser Gln Asn Val Pro Ala Pro Ser Leu
1               5               10              15

Pro Thr Val Ser Gln Tyr Ala Cys Gln Arg Arg Thr Thr Leu Asp Asn
            20              25              30

His Asn Lys Val Phe Thr Asp Ala Leu Glu Val Leu Ile Glu Asn Tyr
            35              40              45

Glu Phe Ser Asp Asn Lys Gly Ala Cys Val Gly Phe Arg Arg Ala Ala
            50              55              60

Ser Val Leu Lys Ser Leu Pro Lys Pro Leu Arg Cys Leu Lys Asp Met
65              70              75              80

Glu Gly Leu Pro Cys Leu Gly Asp Asp Thr Lys Ala Ile Ile Glu Glu
            85              90              95

Ile Tyr Glu Cys Gly Ser Ser Ser Arg Val Glu Asn Ile Leu Ser Asp
            100             105             110

Glu Lys Tyr Gln Thr Leu Lys Leu Phe Thr Ser Val Phe Gly Val Gly
            115             120             125

Pro Lys Thr Gly Glu Lys Trp Tyr Arg Arg Gly Leu Arg Ala Leu Glu
            130             135             140

Gln Val His Ser Glu Pro Ser Ile Gln Leu Asn Lys Met Gln Ala Ala
145             150             155             160

Gly Phe Leu Tyr Tyr Glu Asp Ile Ser Lys Pro Val Ser Arg Ala Glu
            165             170             175

Ala Lys Ala Val Gly Cys Ile Ile Glu Glu Val Ala Ser Cys Phe Ser
            180             185             190

Ser Ser Val Thr Ile Thr Leu Thr Gly Gly Phe Arg Arg Gly Lys Glu
            195             200             205

Phe Gly His Asp Val Asp Phe Leu Leu Ser Ile Pro Glu Pro Gly Lys
            210             215             220

Glu Asp Gly Leu Leu Pro Ala Val Ile Asp Arg Leu Arg Lys Gln Gly
225             230             235             240
```

```
Ile Leu Leu Tyr Ser Asp Leu Gln Glu Ser Thr Leu Gln Gln Trp Lys
                245                 250                 255

Arg Pro Ser Arg Cys Phe Asp Ser Met Asp His Phe Gln Lys Cys Phe
                260                 265                 270

Leu Ile Val Lys Leu Trp Thr Arg Leu Val Glu Gly His Arg Glu Asp
                275                 280                 285

Pro Ser Ser Gln Arg Asp Trp Lys Ala Val Arg Val Asp Leu Val Val
                290                 295                 300

Pro Pro Val Asp Cys Tyr Ala Phe Ala Leu Leu Gly Trp Ser Gly Ser
305                 310                 315                 320

Thr Gln Phe Glu Arg Asp Leu Arg Arg Phe Ala Arg Leu Glu Arg Arg
                325                 330                 335

Met Leu Leu Asp Asn His Ala Leu Tyr Asp Lys Thr Thr Asn Thr Phe
                340                 345                 350

Leu Gln Ala Lys Thr Glu Glu Asp Ile Phe Ala His Leu Gly Leu Asp
                355                 360                 365

Tyr Ile Glu Pro Trp Gln Arg Asn Ala
        370                 375
```

```
<210> SEQ ID NO 23
<211> LENGTH: 378
<212> TYPE: PRT
<213> ORGANISM: Anabas testudineus

<400> SEQUENCE: 23
```

```
Ser Pro Ser Pro Val Pro Gly Ser Gln Asn Val Pro Ala Pro Ser Val
1               5                   10                  15

Ala Thr Val Ser Gln Tyr Ala Cys Gln Arg Arg Thr Thr Thr Glu Asn
                20                  25                  30

Asn Asn Lys Ile Leu Thr Asp Ala Phe Glu Val Leu Ala Glu Ser Tyr
            35                  40                  45

Glu Leu Asn Gln Leu Glu Gly Pro Cys Leu Ala Phe Arg Arg Ala Ala
    50                  55                  60

Ser Val Leu Lys Ser Leu Pro Trp Ala Val Gln Cys Leu Gly Ala Thr
65                  70                  75                  80

Gln Gly Leu Pro Cys Leu Gly Glu His Thr Lys Ala Leu Ile Glu Glu
                85                  90                  95

Ile Leu Gln Tyr Gly His Ser Phe Glu Val Glu Lys Ile Leu Ser Asp
                100                 105                 110

Glu Arg Tyr Gln Thr Leu Lys Leu Phe Thr Ser Val Phe Gly Val Gly
                115                 120                 125

Pro Lys Thr Ala Glu Lys Trp Tyr Arg Arg Gly Leu Arg Ser Phe Ser
                130                 135                 140

Asp Ile Leu Ala Glu Pro Ser Ile Gln Leu Asn Arg Met Gln Gln Ser
145                 150                 155                 160

Gly Phe Leu His Tyr Gly Asp Ile Ser Arg Ala Val Ser Lys Ala Glu
                165                 170                 175

Ala Arg Ala Leu Gly Asn Ile Ile Asp Glu Ala Val His Ala Ile Thr
                180                 185                 190

Pro Asp Gly Ile Leu Ala Leu Thr Gly Gly Phe Arg Arg Gly Lys Glu
                195                 200                 205

Phe Gly His Asp Val Asp Phe Ile Val Thr Thr Pro Glu Gln Gly Lys
        210                 215                 220

Glu Glu Thr Leu Leu Pro Asn Ile Ile Asp Arg Leu Lys Glu Gln Gly
```

-continued

```
225                 230                 235                 240
Ile Leu Leu Tyr Ser Asp Tyr Gln Thr Ser Thr Phe Asp Ile Ser Lys
            245                 250                 255

Leu Pro Ser His Lys Phe Glu Ala Met Asp His Phe Ala Lys Cys Phe
            260                 265                 270

Leu Ile Leu Arg Leu Glu Gly Ser Leu Val Asp Arg Gly Leu Asn Ser
            275                 280                 285

Thr Glu Gly Asp Ser Arg Gly Trp Arg Ala Val Arg Val Asp Leu Val
    290                 295                 300

Ser Pro Pro Met Glu Arg Tyr Ala Tyr Ala Leu Leu Gly Trp Thr Gly
305                 310                 315                 320

Ser Arg Gln Phe Glu Arg Asp Leu Arg Arg Phe Ala Arg Leu Glu Gln
            325                 330                 335

His Met Leu Leu Asp Asn His Ala Leu Tyr Asp Lys Thr Lys Lys Glu
            340                 345                 350

Phe Leu Ala Ala Thr Thr Glu Arg Asp Ile Phe Ala His Leu Gly Leu
            355                 360                 365

Glu Tyr Ile Glu Pro Trp Gln Arg Asn Ala
    370                 375
```

```
<210> SEQ ID NO 24
<211> LENGTH: 378
<212> TYPE: PRT
<213> ORGANISM: ARTIFICIAL SEQUENCE
<220> FEATURE:
<223> OTHER INFORMATION: trunc wt (Poecilia reticulate) guppy

<400> SEQUENCE: 24

Ser Pro Ser Pro Val Pro Gly Ser Gln Asn Val Pro Ala Pro Ser Val
1               5                   10                  15

Asp Lys Val Ser Gln Tyr Ala Cys Gln Arg Arg Thr Thr Val Glu Asn
            20                  25                  30

Asn Asn Arg Ile Phe Thr Asp Ala Phe Glu Val Leu Ala Glu Asn Tyr
        35                  40                  45

Glu Phe Asn Glu Ile Glu Gly Arg Cys Leu Ala Phe Arg Arg Ala Ala
    50                  55                  60

Ser Val Leu Lys Ser Leu Pro Trp Ala Val Arg Ser Val Gly Ala Thr
65                  70                  75                  80

Leu Asp Leu Pro Cys Leu Gly Glu His Thr Thr Ala Val Met Lys Glu
                85                  90                  95

Ile Leu Gln Tyr Gly Arg Ser Phe Glu Val Glu Lys Ile Leu Ser Asp
            100                 105                 110

Glu Arg Cys Gln Thr Leu Lys Leu Phe Thr Ser Val Phe Gly Val Gly
        115                 120                 125

Pro Lys Thr Ala Glu Lys Trp Tyr Arg Arg Gly Leu Arg Ser Phe Ser
    130                 135                 140

Asp Val Leu Ala Gln Pro Gly Ile His Leu Asn Arg Met Gln Gln Ser
145                 150                 155                 160

Gly Phe Leu His Tyr Gly Asp Ile Ser Arg Ala Val Ser Lys Ala Glu
                165                 170                 175

Ala Arg Ala Val Gly Asn Ile Ile Asp Glu Ala Val His Val Ile Thr
            180                 185                 190

Pro Asn Ala Ile Leu Ala Leu Thr Gly Gly Phe Arg Arg Gly Lys Asp
        195                 200                 205

Phe Gly His Asp Val Asp Phe Ile Val Thr Thr Thr Glu Leu Gly Lys
```

-continued

```
        210                 215                 220
Glu Lys Asn Leu Leu Ile Ser Val Ile Glu Ser Leu Lys Lys Gln Gly
225                 230                 235                 240

Leu Leu Leu Phe Ser Asp Tyr Gln Ala Ser Thr Phe Asp Ile Ser Lys
                245                 250                 255

Leu Pro Ser His Arg Phe Glu Ala Met Asp His Phe Ala Lys Cys Phe
                260                 265                 270

Leu Ile Leu Arg Leu Glu Gly Ser Arg Val Glu Gly Gly Leu Gln Arg
                275                 280                 285

Ala Gln Ala Asp Gly Arg Gly Trp Arg Ala Val Arg Val Asp Leu Val
        290                 295                 300

Ser Pro Pro Ala Asp Arg Phe Ala Phe Thr Met Leu Gly Trp Thr Gly
305                 310                 315                 320

Ser Arg Met Phe Glu Arg Asp Leu Arg Arg Phe Ala Arg Leu Glu Arg
                325                 330                 335

Gln Met Leu Leu Asp Asn His Ala Leu Tyr Asp Lys Thr Lys Lys Glu
                340                 345                 350

Phe Leu Thr Ala Ala Thr Glu Lys Asp Ile Phe Asp His Leu Gly Leu
                355                 360                 365

Glu Tyr Ile Glu Pro Trp Gln Arg Asn Ala
        370                 375

<210> SEQ ID NO 25
<211> LENGTH: 366
<212> TYPE: PRT
<213> ORGANISM: ARTIFICIAL SEQUENCE
<220> FEATURE:
<223> OTHER INFORMATION: trunc wt  short Rattus norvegicus

<400> SEQUENCE: 25

Pro Leu Met Gln Lys Ile Ser Gln Tyr Ala Cys Gln Arg Arg Thr Thr
1               5                   10                  15

Leu Asn Asn His Asn Gln Leu Phe Thr Asp Ala Phe Asp Ile Leu Ala
                20                  25                  30

Glu Asn Tyr Glu Phe Arg Glu Asn Glu Val Ser Cys Leu Pro Phe Met
                35                  40                  45

Arg Ala Ala Ser Val Leu Lys Ser Leu Ser Phe Pro Ile Val Ser Met
        50                  55                  60

Lys Asp Ile Glu Gly Ile Pro Cys Leu Gly Asp Lys Val Lys Cys Val
65                  70                  75                  80

Ile Glu Gly Ile Ile Glu Asp Gly Glu Ser Ser Glu Val Lys Ala Val
                85                  90                  95

Leu Asn Asp Glu Arg Tyr Lys Ser Phe Lys Leu Phe Thr Ser Val Phe
                100                 105                 110

Gly Val Gly Leu Lys Thr Ala Glu Lys Trp Phe Arg Met Gly Phe Arg
                115                 120                 125

Thr Leu Ser Lys Ile Lys Ser Asp Lys Ser Leu Arg Phe Thr His Met
        130                 135                 140

Gln Lys Ala Gly Phe Leu Tyr Tyr Glu Asp Leu Val Ser Cys Val Asn
145                 150                 155                 160

Arg Ala Glu Ala Glu Ala Val Ser Met Leu Val Lys Glu Ala Val Val
                165                 170                 175

Ala Phe Leu Pro Asp Ala Leu Val Thr Met Thr Gly Gly Phe Arg Arg
                180                 185                 190

Gly Lys Met Thr Gly His Asp Val Asp Phe Leu Ile Thr Ser Pro Glu
```

-continued

```
                195                  200                  205
Ala Thr Glu Glu Glu Glu Gln Gln Leu Leu His Lys Val Thr Asn Phe
    210                  215                  220

Trp Arg Gln Gln Gly Leu Leu Leu Tyr Cys Asp Ile Ile Glu Ser Thr
225                  230                  235                  240

Phe Glu Lys Phe Lys Leu Pro Ser Arg Lys Val Asp Ala Leu Asp His
                245                  250                  255

Phe Gln Lys Cys Phe Leu Ile Leu Lys Leu His Arg Gly Leu Val Arg
            260                  265                  270

Ser Glu Glu Ser Gly Gln Gln Glu Gly Lys Asp Trp Lys Ala Ile Arg
            275                  280                  285

Val Asp Leu Val Met Cys Pro Tyr Glu Arg Arg Ala Phe Ala Leu Leu
    290                  295                  300

Gly Trp Thr Gly Ser Arg Gln Phe Glu Arg Asp Leu Arg Arg Tyr Ala
305                  310                  315                  320

Thr His Glu Arg Lys Met Met Leu Asp Asn His Ala Leu Tyr Asp Lys
                325                  330                  335

Thr Lys Arg Val Phe Leu Glu Ala Glu Ser Glu Glu Glu Ile Phe Ala
            340                  345                  350

His Leu Gly Leu Asp Tyr Ile Glu Pro Trp Glu Arg Asn Ala
            355                  360                  365
```

<210> SEQ ID NO 26
<211> LENGTH: 379
<212> TYPE: PRT
<213> ORGANISM: ARTIFICIAL SEQUENCE
<220> FEATURE:
<223> OTHER INFORMATION: trunk wt  Long Rattus norvegicus

<400> SEQUENCE: 26

```
Ser Leu Ser Pro Val Pro Gly Ser Gln Thr Val Pro Pro Pro Leu Met
1                5                  10                  15

Gln Lys Ile Ser Gln Tyr Ala Cys Gln Arg Arg Thr Thr Leu Asn Asn
            20                  25                  30

His Asn Gln Leu Phe Thr Asp Ala Phe Asp Ile Leu Ala Glu Asn Tyr
        35                  40                  45

Glu Phe Arg Glu Asn Glu Val Ser Cys Leu Pro Phe Met Arg Ala Ala
    50                  55                  60

Ser Val Leu Lys Ser Leu Ser Phe Pro Ile Val Ser Met Lys Asp Ile
65                  70                  75                  80

Glu Gly Ile Pro Cys Leu Gly Asp Lys Val Lys Cys Val Ile Glu Gly
                85                  90                  95

Ile Ile Glu Asp Gly Glu Ser Ser Glu Val Lys Ala Val Leu Asn Asp
            100                  105                  110

Glu Arg Tyr Lys Ser Phe Lys Leu Phe Thr Ser Val Phe Gly Val Gly
        115                  120                  125

Leu Lys Thr Ala Glu Lys Trp Phe Arg Met Gly Phe Arg Thr Leu Ser
    130                  135                  140

Lys Ile Lys Ser Asp Lys Ser Leu Arg Phe Thr His Met Gln Lys Ala
145                  150                  155                  160

Gly Phe Leu Tyr Tyr Glu Asp Leu Val Ser Cys Val Asn Arg Ala Glu
                165                  170                  175

Ala Glu Ala Val Ser Met Leu Val Lys Glu Ala Val Val Ala Phe Leu
            180                  185                  190

Pro Asp Ala Leu Val Thr Met Thr Gly Gly Phe Arg Arg Gly Lys Met
```

-continued

```
              195                 200                 205

Thr Gly His Asp Val Asp Phe Leu Ile Thr Ser Pro Glu Ala Thr Glu
    210                 215                 220

Glu Glu Glu Gln Gln Leu Leu His Lys Val Thr Asn Phe Trp Arg Gln
225                 230                 235                 240

Gln Gly Leu Leu Leu Tyr Cys Asp Ile Ile Glu Ser Thr Phe Glu Lys
                245                 250                 255

Phe Lys Leu Pro Ser Arg Lys Val Asp Ala Leu Asp His Phe Gln Lys
                260                 265                 270

Cys Phe Leu Ile Leu Lys Leu His Arg Gly Leu Val Arg Ser Glu Glu
                275                 280                 285

Ser Gly Gln Gln Glu Gly Lys Asp Trp Lys Ala Ile Arg Val Asp Leu
    290                 295                 300

Val Met Cys Pro Tyr Glu Arg Arg Ala Phe Ala Leu Leu Gly Trp Thr
305                 310                 315                 320

Gly Ser Arg Gln Phe Glu Arg Asp Leu Arg Arg Tyr Ala Thr His Glu
                325                 330                 335

Arg Lys Met Met Leu Asp Asn His Ala Leu Tyr Asp Lys Thr Lys Arg
                340                 345                 350

Val Phe Leu Glu Ala Glu Ser Glu Glu Glu Ile Phe Ala His Leu Gly
                355                 360                 365

Leu Asp Tyr Ile Glu Pro Trp Glu Arg Asn Ala
    370                 375

<210> SEQ ID NO 27
<211> LENGTH: 379
<212> TYPE: PRT
<213> ORGANISM: ARTIFICIAL SEQUENCE
<220> FEATURE:
<223> OTHER INFORMATION: trunc wt (Piliocolobus tephrosceles) monkey

<400> SEQUENCE: 27

Ser Asp Ser Thr Asn Pro Gly Leu Pro Lys Thr Pro Pro Thr Ala Ile
1               5                   10                  15

Gln Lys Ile Ser Gln Tyr Ala Cys Gln Arg Arg Thr Thr Leu Asn Asn
                20                  25                  30

Cys Asn Gln Ile Phe Thr Asp Ala Phe Asp Ile Leu Ala Glu Asn Cys
            35                  40                  45

Glu Phe Arg Glu Asn Glu Asp Ser Cys Val Thr Phe Met Arg Ala Ala
    50                  55                  60

Ser Val Leu Lys Ser Leu Pro Phe Thr Ile Ile Ser Met Lys Asp Thr
65                  70                  75                  80

Glu Gly Ile Pro Cys Leu Gly Ser Lys Val Lys Cys Ile Ile Glu Glu
                85                  90                  95

Ile Ile Glu Asp Gly Glu Ser Ser Glu Val Lys Ala Val Leu Asn Asp
                100                 105                 110

Glu Arg Tyr Gln Ser Phe Lys Leu Phe Thr Ser Val Phe Gly Val Gly
            115                 120                 125

Leu Lys Thr Ser Glu Lys Trp Phe Arg Met Gly Phe Arg Thr Leu Ser
    130                 135                 140

Lys Val Arg Ser Asp Glu Ser Leu Lys Phe Thr Arg Met Gln Arg Ala
145                 150                 155                 160

Gly Phe Leu Tyr Tyr Glu Asp Leu Val Ser Cys Val Thr Arg Ala Glu
                165                 170                 175

Ala Glu Ala Val Ser Ala Leu Val Lys Glu Ala Val Trp Ala Phe Leu
```

-continued

```
            180                 185                 190

Pro Asp Ala Phe Val Thr Met Thr Gly Gly Phe Arg Arg Gly Lys Lys
            195                 200                 205

Met Gly His Asp Val Asp Phe Leu Ile Thr Ser Pro Gly Ser Thr Glu
            210                 215                 220

Asp Glu Glu Gln Gln Leu Leu Gln Lys Val Met Asn Leu Trp Glu Lys
225                 230                 235                 240

Lys Gly Leu Leu Leu Tyr Tyr Asp Leu Val Glu Ser Thr Phe Glu Lys
                    245                 250                 255

Leu Arg Leu Pro Ser Arg Lys Val Asp Ala Leu Asp His Phe Gln Lys
                    260                 265                 270

Cys Phe Leu Ile Phe Lys Leu Pro Leu Gln Arg Val Asp Ser Asp Gln
                    275                 280                 285

Ser Ser Trp Gln Gly Gly Lys Thr Trp Lys Ala Ile Arg Val Asp Leu
            290                 295                 300

Val Met Cys Pro Tyr Glu Arg Arg Ala Phe Ala Leu Leu Gly Trp Thr
305                 310                 315                 320

Gly Ser Arg Gln Phe Glu Arg Asp Leu Arg Arg Tyr Ala Thr His Glu
                    325                 330                 335

Arg Lys Met Ile Leu Asp Asn His Ala Leu Tyr Asp Lys Thr Lys Arg
                    340                 345                 350

Ile Phe Leu Lys Ala Glu Ser Glu Glu Glu Ile Phe Ala His Leu Gly
            355                 360                 365

Leu Asp Tyr Ile Glu Pro Trp Glu Arg Asn Ala
            370                 375
```

```
<210> SEQ ID NO 28
<211> LENGTH: 379
<212> TYPE: PRT
<213> ORGANISM: ARTIFICIAL SEQUENCE
<220> FEATURE:
<223> OTHER INFORMATION: N27 trunc wt (Sus scrofa) pig

<400> SEQUENCE: 28

Ser Ala Ser Pro Ser Pro Gly Ser Gln Asn Thr Leu Pro Pro Ala Val
1               5                   10                  15

Lys Lys Ile Ser Gln Tyr Ala Cys Gln Arg Arg Thr Thr Leu Asn Asn
            20                  25                  30

Cys Asn His Ile Phe Thr Asp Ala Phe Glu Val Leu Ala Glu Asn Tyr
            35                  40                  45

Glu Phe Arg Glu Asn Glu Thr Phe Cys Leu Ala Phe Met Arg Ala Ala
            50                  55                  60

Ser Val Leu Lys Ser Leu Pro Phe Thr Ile Ile Ser Met Lys Asp Thr
65                  70                  75                  80

Glu Gly Ile Pro Cys Leu Gly Asp Lys Val Lys Cys Val Ile Glu Glu
                    85                  90                  95

Ile Ile Glu Asp Gly Glu Ser Ser Glu Val Lys Ala Val Leu Asn Asp
            100                 105                 110

Glu Arg Tyr Gln Ser Phe Lys Leu Phe Thr Ser Val Phe Gly Val Gly
            115                 120                 125

Leu Lys Thr Ser Glu Arg Trp Phe Arg Met Gly Phe Arg Ser Leu Ser
            130                 135                 140

Lys Ile Arg Ser Asp Lys Thr Leu Lys Phe Thr Arg Met Gln Lys Ala
145                 150                 155                 160

Gly Phe Leu Tyr Tyr Glu Asp Leu Val Ser Cys Val Thr Arg Ala Glu
```

-continued

```
                165                 170                 175
Ala Glu Ala Val Gly Val Leu Val Lys Glu Ala Val Gln Ala Phe Leu
                180                 185                 190

Pro Asp Ala Phe Val Thr Met Thr Gly Gly Phe Arg Arg Gly Lys Lys
                195                 200                 205

Met Gly His Asp Val Asp Phe Leu Ile Thr Ser Pro Gly Ser Thr Asp
        210                 215                 220

Asp Glu Glu Gln Gln Leu Leu Pro Lys Val Val Asn Leu Trp Glu Arg
225                 230                 235                 240

Glu Gly Leu Leu Leu Tyr Cys Asp Leu Val Glu Ser Thr Leu Glu Lys
                245                 250                 255

Ser Lys Leu Pro Ser Arg Asn Val Asp Ala Leu Asp His Phe Gln Lys
                260                 265                 270

Cys Phe Leu Ile Leu Lys Leu His His Gln Arg Val Asp Ser Gly Met
                275                 280                 285

Ser Ser Gln Gln Glu Gly Lys Thr Trp Lys Ala Ile Arg Val Asp Leu
        290                 295                 300

Val Met Cys Pro Tyr Glu Leu Arg Ala Phe Ala Leu Leu Gly Trp Thr
305                 310                 315                 320

Gly Ser Arg Gln Phe Glu Arg Asp Leu Arg Arg Tyr Ala Thr His Glu
                325                 330                 335

Arg Lys Met Ile Leu Asp Asn His Ala Leu Tyr Asp Lys Thr Lys Arg
                340                 345                 350

Ile Phe Leu Lys Ala Glu Ser Glu Glu Glu Ile Phe Ala His Leu Gly
                355                 360                 365

Leu Asp Tyr Leu Glu Pro Trp Glu Arg Asn Ala
        370                 375
```

```
<210> SEQ ID NO 29
<211> LENGTH: 379
<212> TYPE: PRT
<213> ORGANISM: ARTIFICIAL SEQUENCE
<220> FEATURE:
<223> OTHER INFORMATION: trunc wt (Panthera tigris altaica) Siberian
      tiger

<400> SEQUENCE: 29

Tyr Ser Ala Ser Pro Asn Pro Glu Leu Gln Lys Thr Pro Pro Leu Val
1               5                   10                  15

Lys Lys Ile Pro Leu Tyr Ala Cys Gln Arg Arg Thr Thr Leu Asn Asn
                20                  25                  30

Phe Asn His Val Phe Thr Asp Ala Phe Glu Val Leu Ala Glu Asn Tyr
                35                  40                  45

Glu Phe Lys Glu Asn Glu Val Ser Ser Ala Thr Phe Met Arg Ala Ala
        50                  55                  60

Ser Val Leu Lys Ser Leu Pro Phe Thr Ile Ile Ser Met Lys Asp Thr
65                  70                  75                  80

Glu Gly Ile Pro Cys Leu Gly Asp Lys Val Lys Cys Val Ile Glu Glu
                85                  90                  95

Ile Ile Glu Asp Gly Glu Ser Ser Glu Val Lys Ala Val Leu Asn Asp
                100                 105                 110

Glu Arg Tyr Gln Ser Phe Lys Leu Phe Thr Ser Val Phe Gly Val Gly
                115                 120                 125

Leu Lys Thr Ser Glu Lys Trp Phe Arg Met Gly Phe Arg Thr Leu Ser
        130                 135                 140
```

-continued

```
Lys Ile Lys Ser Asp Lys Thr Leu Lys Phe Thr Gln Met Gln Lys Ala
145                 150                 155                 160

Gly Phe Leu Tyr Tyr Glu Asp Leu Val Ser Cys Val Thr Arg Ala Glu
                165                 170                 175

Ala Glu Ala Val Gly Val Leu Val Lys Glu Ala Val Trp Ala Phe Leu
            180                 185                 190

Pro Asp Ala Phe Val Thr Met Thr Gly Gly Phe Arg Arg Gly Lys Lys
            195                 200                 205

Ile Gly His Asp Val Asp Phe Leu Ile Thr Ser Pro Gly Ser Thr Asp
        210                 215                 220

Glu Glu Glu Glu Glu Leu Leu Pro Lys Val Ile Asn Leu Trp Gln Arg
225                 230                 235                 240

Lys Glu Leu Leu Leu Tyr Tyr Asp Leu Val Glu Ser Thr Phe Glu Lys
                245                 250                 255

Leu Lys Leu Pro Ser Arg Lys Val Asp Ala Leu Asp His Phe Gln Lys
                260                 265                 270

Cys Phe Leu Ile Leu Lys Leu His His Gln Arg Val Asp Ser Gly Lys
            275                 280                 285

Cys Ser Gln Gln Glu Gly Lys Thr Trp Lys Ala Ile Arg Val Asp Leu
        290                 295                 300

Val Met Cys Pro Tyr Glu Arg Arg Ala Phe Ala Leu Leu Gly Trp Thr
305                 310                 315                 320

Gly Ser Arg Gln Phe Glu Arg Asp Leu Arg Arg Tyr Ala Thr His Glu
                325                 330                 335

Arg Lys Met Ile Leu Asp Asn His Ala Leu Tyr Asp Lys Thr Lys Lys
                340                 345                 350

Ile Phe Leu Lys Ala Glu Ser Glu Glu Glu Ile Phe Ala His Leu Gly
                355                 360                 365

Leu Asp Tyr Ile Glu Pro Trp Glu Arg Asn Ala
            370                 375
```

```
<210> SEQ ID NO 30
<211> LENGTH: 365
<212> TYPE: PRT
<213> ORGANISM: ARTIFICIAL SEQUENCE
<220> FEATURE:
<223> OTHER INFORMATION: trunc wt (Bubalus bubalis) water buffalo

<400> SEQUENCE: 30
```

```
Leu Ala Val Lys Lys Ile Ser Gln Tyr Ala Cys Gln Arg Lys Thr Thr
1                   5                   10                  15

Leu Asn Asn Tyr Asn His Ile Phe Thr Asp Ala Phe Glu Ile Leu Ala
                20                  25                  30

Glu Asn Ser Glu Phe Lys Glu Asn Glu Val Ser Tyr Val Thr Phe Met
            35                  40                  45

Arg Ala Ala Ser Val Leu Lys Ser Leu Pro Phe Thr Ile Ile Ser Met
        50                  55                  60

Lys Asp Thr Gln Gly Ile Pro Cys Leu Gly Asp Lys Val Lys Cys Val
65                  70                  75                  80

Ile Glu Glu Ile Ile Glu Asp Gly Glu Ser Ser Glu Val Lys Ala Val
                85                  90                  95

Leu Asn Asp Glu Arg Tyr Gln Ser Phe Lys Leu Phe Thr Ser Val Phe
                100                 105                 110

Gly Val Gly Leu Lys Thr Ser Glu Lys Trp Phe Arg Met Gly Phe Arg
                115                 120                 125
```

-continued

```
Ser Leu Ser Lys Ile Thr Ser Asp Lys Thr Leu Lys Phe Thr Lys Met
    130                 135                 140

Gln Lys Ala Gly Phe Leu Tyr Tyr Glu Asp Leu Val Ser Cys Val Thr
145                 150                 155                 160

Arg Ala Glu Ala Glu Ala Val Gly Val Leu Val Lys Glu Ala Val Trp
                165                 170                 175

Ala Phe Leu Pro Asp Ala Phe Ile Thr Met Thr Gly Gly Phe Arg Arg
                180                 185                 190

Gly Lys Lys Ile Gly His Asp Val Asp Phe Leu Ile Thr Ser Pro Gly
                195                 200                 205

Ser Ala Glu Asp Glu Glu Gln Leu Leu Pro Lys Val Ile Asn Leu Trp
    210                 215                 220

Glu Lys Lys Gly Leu Leu Leu Tyr Tyr Asp Leu Val Glu Ser Thr Phe
225                 230                 235                 240

Glu Lys Phe Lys Leu Pro Ser Arg Gln Val Asp Thr Leu Asp His Phe
                245                 250                 255

Gln Lys Cys Phe Leu Ile Leu Lys Leu His His Gln Arg Val Asp Ser
                260                 265                 270

Gly Arg Ser Asn Gln Gln Glu Gly Lys Thr Trp Lys Ala Ile Arg Val
    275                 280                 285

Asp Leu Val Met Cys Pro Tyr Glu Asn Arg Ala Phe Ala Leu Leu Gly
    290                 295                 300

Trp Thr Gly Ser Arg Gln Phe Glu Arg Asp Ile Arg Arg Tyr Ala Thr
305                 310                 315                 320

His Glu Arg Lys Met Met Leu Asp Asn His Ala Leu Tyr Asp Lys Thr
                325                 330                 335

Lys Arg Val Phe Leu Lys Ala Glu Ser Glu Glu Glu Ile Phe Ala His
                340                 345                 350

Leu Gly Leu Asp Tyr Ile Glu Pro Trp Glu Arg Asn Ala
                355                 360                 365
```

```
<210> SEQ ID NO 31
<211> LENGTH: 379
<212> TYPE: PRT
<213> ORGANISM: ARTIFICIAL SEQUENCE
<220> FEATURE:
<223> OTHER INFORMATION: N93or trunc wt (Marmota flaviventris) marmot

<400> SEQUENCE: 31
```

```
Pro Asp His Ser Asn Ser Asp Pro Gln Arg Ile Pro Pro Pro Ala Val
1                   5                   10                  15

Gln Thr Ile Ser Gln Tyr Ala Cys Gln Arg Arg Thr Thr Leu Asn Asn
                20                  25                  30

Cys Asn Arg Val Phe Thr Asp Ala Phe Asp Val Leu Ala Glu Asn Tyr
                35                  40                  45

Glu Phe Arg Glu Asn Glu Ser Cys Ser Val Val Phe Met Arg Ala Ala
    50                  55                  60

Ser Val Leu Lys Ser Leu Pro Phe Thr Ile Ile Ser Met Arg Asp Leu
65                  70                  75                  80

Glu Gly Ile Pro Cys Leu Glu Gly Lys Ala Lys Ser Ile Ile Glu Glu
                85                  90                  95

Ile Ile Glu Asp Gly Glu Ser Ser Glu Val Lys Ala Val Leu Asn Asp
                100                 105                 110

Glu Arg Tyr Lys Ser Phe Lys Leu Phe Thr Ser Val Phe Gly Val Gly
    115                 120                 125
```

-continued

```
Leu Lys Thr Ser Glu Lys Trp Phe Arg Met Gly Phe Arg Thr Leu Ser
    130             135             140

Lys Ile Arg Ser Asp Lys Ser Leu Lys Phe Thr His Met Gln Lys Ala
145             150             155             160

Gly Phe Leu Tyr Tyr Glu Asp Leu Val Ser Cys Val Thr Arg Ala Glu
            165             170             175

Ala Glu Ala Val Ser Val Leu Val Lys Glu Ala Val Trp Ala Phe Leu
            180             185             190

Pro Asp Ala Phe Ile Thr Met Thr Gly Gly Phe Arg Arg Gly Lys Asn
        195             200             205

Ile Gly His Asp Val Asp Phe Leu Ile Thr Ser Ala Glu Ala Thr Glu
    210             215             220

Glu Glu Glu Gln Gln Leu Leu His Lys Val Thr Asn Leu Trp Glu Lys
225             230             235             240

Lys Gly Leu Leu Leu Tyr Cys Asp Leu Val Glu Ser Thr Phe Glu Lys
            245             250             255

Leu Lys Thr Pro Ser Arg Lys Val Asp Ala Leu Asp His Phe Gln Lys
            260             265             270

Cys Phe Leu Ile Leu Lys Leu His His Gln Arg Val Asp Ser Asp Lys
        275             280             285

Ala Ser Gln Gln Gly Gly Lys Asn Trp Lys Ala Ile Arg Val Asp Leu
    290             295             300

Val Met Cys Pro Tyr Glu Arg Arg Ala Phe Ala Leu Leu Gly Trp Thr
305             310             315             320

Gly Ser Arg Gln Phe Glu Arg Asp Leu Arg Arg Tyr Ala Thr His Glu
            325             330             335

Arg Lys Met Ile Leu Asp Asn His Ala Leu Tyr Asp Lys Thr Lys Arg
            340             345             350

Ile Phe Leu Lys Ala Glu Ser Glu Glu Glu Ile Phe Ala His Leu Gly
    355             360             365

Leu Asp Tyr Ile Glu Pro Trp Glu Arg Asn Ala
    370             375
```